(12) United States Patent
Newman et al.

(10) Patent No.: US 10,323,095 B2
(45) Date of Patent: Jun. 18, 2019

(54) ANTIBODY-FYNOMER CONJUGATES

(71) Applicant: MITSUBISHI TANABE PHARMA CORPORATION, Osaka-shi, Osaka (JP)

(72) Inventors: Roland Newman, San Diego, CA (US); Steve Granger, Encinitas, CA (US); Michael Lyman, San Diego, CA (US); Dragan Grabulovski, Zurich (CH); Richard Woods, Zurich (CH); Michela Silacci, Zurich (CH); Wenjuan Zha, Zurich (CH); Isabella Attinger-Toller, Vancouver (CA)

(73) Assignee: MITSUBISHI TANABE PHARMA CORPORATION, Osaka-shi, Osaka (JP)

( * ) Notice: Subject to any disclaimer, the term of this patent is extended or adjusted under 35 U.S.C. 154(b) by 0 days.

(21) Appl. No.: 15/126,551

(22) PCT Filed: Mar. 16, 2015

(86) PCT No.: PCT/JP2015/058645
§ 371 (c)(1),
(2) Date: Sep. 15, 2016

(87) PCT Pub. No.: WO2015/141862
PCT Pub. Date: Sep. 24, 2015

(65) Prior Publication Data
US 2017/0081412 A1 Mar. 23, 2017

Related U.S. Application Data

(60) Provisional application No. 61/954,437, filed on Mar. 17, 2014.

(51) Int. Cl.
| | |
|---|---|
| *C07K 16/28* | (2006.01) |
| *C12N 9/12* | (2006.01) |
| *C12N 15/62* | (2006.01) |
| *C12N 9/96* | (2006.01) |
| *C07K 16/24* | (2006.01) |
| *A61K 38/00* | (2006.01) |
| *A61K 39/00* | (2006.01) |

(52) U.S. Cl.
CPC ........ *C07K 16/2866* (2013.01); *C07K 16/244* (2013.01); *C12N 9/12* (2013.01); *C12N 9/1205* (2013.01); *C12N 9/96* (2013.01); *C12N 15/62* (2013.01); *C12Y 207/01112* (2013.01); *C12Y 207/10* (2013.01); *A61K 38/00* (2013.01); *A61K 2039/505* (2013.01); *C07K 2317/24* (2013.01); *C07K 2317/31* (2013.01); *C07K 2317/565* (2013.01); *C07K 2317/76* (2013.01); *C07K 2317/92* (2013.01); *C07K 2317/94* (2013.01); *C07K 2318/20* (2013.01); *C07K 2319/00* (2013.01); *C07K 2319/33* (2013.01); *C07K 2319/70* (2013.01)

(58) Field of Classification Search
CPC .................................................. C07K 16/2866
See application file for complete search history.

(56) References Cited

U.S. PATENT DOCUMENTS

| | | | | |
|---|---|---|---|---|
| 6,632,927 | B2 * | 10/2003 | Adair | C07K 16/18 424/133.1 |
| 8,562,991 | B2 | 10/2013 | Igawa et al. | |
| 2011/0076275 | A1 | 3/2011 | Igawa et al. | |
| 2011/0280873 | A1 | 11/2011 | Presta et al. | |
| 2013/0005659 | A1 | 1/2013 | Grabulovski et al. | |
| 2013/0022625 | A1 | 1/2013 | Igawa et al. | |
| 2015/0047065 | A1 | 2/2015 | Brack et al. | |

FOREIGN PATENT DOCUMENTS

| | | |
|---|---|---|
| CN | 102858366 A | 1/2013 |
| EP | 2 597 102 | 5/2013 |
| EP | 2597102 A1 | 5/2013 |
| EP | 2 638 916 | 9/2013 |
| EP | 2638916 A1 | 9/2013 |
| JP | 2011-523853 | 8/2011 |
| JP | 2011523853 A | 8/2011 |
| JP | 2013-502910 | 1/2013 |
| JP | 2013502910 A | 1/2013 |
| RU | 2430111 C1 | 9/2011 |
| WO | 2009/140348 A2 | 11/2009 |
| WO | 2009/140348 A3 | 11/2009 |
| WO | 2009/140348 A4 | 11/2009 |
| WO | 2009149189 A2 | 12/2009 |
| WO | WO 2009/149189 | 12/2009 |
| WO | 2013/087911 A1 | 6/2013 |

(Continued)

OTHER PUBLICATIONS

Lederman et al (1991), Molecular Immunology, vol. 28, No. 11, pp. 1171-1181.*
Li et al. (2004), International Immunology, vol. 4, pp. 693-708.*
Panka et al. Proc. Natl. Acad. Sci. USA vol. 85, pp. 3080-3084 (May 1988).*
Rudikoff et al. Proc. Natl. Acad. Sci. USA vol. 79, pp. 1979-1983 (Mar. 1982).*
Amit et al. Science, Vot. 233, pp. 747-753, (Aug. 1986).*

(Continued)

*Primary Examiner* — Prema M Mertz
(74) *Attorney, Agent, or Firm* — Pillsbury Winthrop Shaw Pittman, LLP

(57) ABSTRACT

Provided is a bi-specific fusion polypeptide comprising a fynomer sequence that binds to interleukin-17a (IL-17a) and is conjugated to an antibody or subsequence thereof that binds to interleukin-6 receptor (IL-6R). The fusion polypeptide can bind to both IL-17a and IL-6R thereby suppresses, reduces, decreases, inhibits or blocks both IL-17a and IL-6R activities.

20 Claims, 61 Drawing Sheets

Specification includes a Sequence Listing.

(56) References Cited

FOREIGN PATENT DOCUMENTS

| WO | 2013135588 A1 | 9/2013 |
| WO | WO 2013/135588 | 9/2013 |
| WO | 2014044758 A1 | 3/2014 |
| WO | WO 2014/044758 | 3/2014 |

OTHER PUBLICATIONS

Grabulovski, D., et al., COVA322 Overcoming Limitations of Current Biologics in Rheumatoid Arthritis by a Novel, Bispecific Tumor-Necrosis-Factor-Alpha/Interleukin-17A (TNF/IL-17A) Inhibitor Moving Towards The Clinic, Arthritis & Rheumatism, 2013, 65(S10):S544.

European Application No. 15765900.4, EPC Communication, Extended European Search Report and Supplementary European Search Report dated Jul. 25, 2017.

Lubberts, "IL-17/Th17 targeting: On the road to prevent chronic destructive arthritis?", (2008) Cytokine, 41, pp. 84-91.

Antonysamy et al., "Evidence for a Role of IL-17 in Organ Allograft Rejection: IL-17 Promotes the Functional Differentiation of Dendritic Cell Progenitors", (1999), J.Immunol., 162, pp. 577-584.

Molet et al., "IL-17 is increaded in asthmatic airways and induces human bronchial fibroblasts to produce cytokines", (2001), J. Allergy Clin. Immunol., vol. 108, No. 3, pp. 430-438.

Van Kooten et al.,"Interleukin-17 Activates Human Renal Epithelial Cells in Vitro and Is Expressed during Renal Allograft Rejection", (1998), J. Am. Soc. Nephrol 9, pp. 1526-1534.

Weaver et al., "IL-17 Family Cytokines and the Expanding Diversity of Effector T Cell Lineages", (2007), Annu. Rev. Immunol., 25, pp. 821-852.

International Search Report dated Jun. 16, 2015 for Appln. No. PCT/JP2015/058645.

International Preliminary Report on Patentability dated Sep. 20, 2016 for Appln. No. PCT/JP2015/058645.

Lubberts et al., "Treatment with a neutralizing anti-murine interleukin-17 antibody after the onset of collagen-inducted arthritis reduces joint inflammation, cartilage destruction and bone erosion", (2004) , Arthritis and Rheumatism, vol. 50, No. 2, pp. 650-659.

Lubberts et al., "Overexpression of IL-17 in the knee joint of collagen type II immunized mice promotes collagen arthritis and aggravates joint destruction", (2002) Inflamm. Res., 51, pp. 102-104.

Teunissen et al., "Interliukin-17 and interferon-γ Synergize in the enhancement of proinflammatory cytokine production by human keratinocytes" (1998) J. Invest. Dermatol, 111, pp. 645-649.

Leonardi et al., "Anti-Interleukin-17 monoclonal antibody ixekizumab in chronic plaque psoriasis", (2012), N. Engl .J. Med., 366; 13, pp. 1190-1199.

Kurasawa et al., "Increased interleukin-17 production in patients with systemic sclerosis", (2000), Arthritis Rheum., vol. 43, No. 11, pp. 2455-2463.

Hueber et al., Effects of AIN457, a fully human antibody to interleukin-17A, on psoriasis, rheumatoid arthritis, and uveitis, (2010), Sci. Transl. Med., vol. 2, Issue52 52ra72, pp. 1-10.

Lubberts et al., "IL-1-Independent Role of IL-17 in synovial inflammation and joint destruction during collagen-induced arthritis", (2001), J. Immunol., 167, pp. 1004-1013.

Antonysamy, A., et al., Evidence for a Role of IL-17 in Organ Allograft Rejection: IL-17 Promotes the Functional Differentiation of Dendritic Cell Progenitors, J. Immunol., 1999, 162:577-584.

Heuber, W., et al., Effects of AIN457, a Fully Human Antibody to Interleukin-17A, on Psoriasis, Rheumatoid Arthritis, and Uveitis, Science Translational Medicine, 2010, 2(52):52ra72.

Kurasawa, K., et al., Increased Interleukin-17 Production in Patients With Systemic Sclerosis, Arthritis & Rheumatism, 2000, 43(11):2455-2463.

Leonardi, C., et al., Anti-Interleukin-17 Monoclonal Antibody Ixekizumab in Chronic Plaque Psoriasis, The New England Journal of Medicine, 2012, 366(13)1190-1199.

Lubberts, E., et al., Overexpression of IL-17 in the Knee Joint of Collagen Type II Immunized Mice Promotes Collagen Arthritis and Aggravates Joint Destruction, Inflamm. Res., 2002, 51:102-104.

Lubberts, E., IL-17/Th17 Targeting: On the Road to Prevent Chronic Destructive Arthritis?, Cytokine, 2008, 41:84-91.

Lubberts, E, et al., IL-1-Independent Role of IL-17 in Synovial Inflammation and Joint Desriction During Collagen-Induced Arthritis, J. Immunol., 2001, 167:1004-1013.

Lubberts, E., et al., Treatment With Neutralizing Anti-Murine Interleukin-17 Antibody After the Onset of Collagen-Induced Arthritis Reduces Joint Inflammation, Cartilage Destruction, and Bone Erosion, Arthritis & Rheumatism, 2004, 50(2):650-659.

Molet, S., et al., IL-17 is Increased in Asthmatic Airways and Induces Human Bronchial Fibroblasts to Produce Cytokines, J. Allergy Clin. Immunol., 2001, 108:430-8.

Teunissen, M.B.M., et al., Interleukin-17 and Interferon-Lambda Synergize in the Enhancement of Proinflammatory Cytokine Production by Human Keratinocytes, J. Invest. Dermatol., 1998, 111:645-649.

Van Kooten, C., et al., Interleukin-17 Activates Human Renal Epithelial Cells in Vitro and Is Expressed during Renal Allograft Rejection, J. Am. Soc. Nephrol., 1998, 9:1526-1534.

Weaver, C. T., et al., IL-17 Family Cytokines and the Expanding Diversity of Effector T Cell Lineages, Annu. Rev. Immunol., 2007, 25:821-52.

Patent Cooperation Treaty International Application No. PCT/JP2015/058645, International Search Report dated Jun. 16, 2015.

Patent Cooperation Treaty International Application No. PCT/JP2015/058645, International Preliminary Report on Patentability dated Sep. 20, 2016 and Written Opinion dated Jun. 16, 2015.

Chinese Intellectual Property Office, Chinese Office Action for CN Patent Application No. 2015814271.5, dated May 17, 2018.

Kosobokova et al., Antibody-Cytokine Fusion Proteins: Production, Functionality and Application Prospects in Oncology, Modern Technologies in Medicine, Jun. 27, 2013, vol. 5, No. 4, pp. 102-111.

Russian Federation, Office Action in Russian Patent Application No. 611297, dated Nov. 12, 2018, pp. 1-7.

* cited by examiner

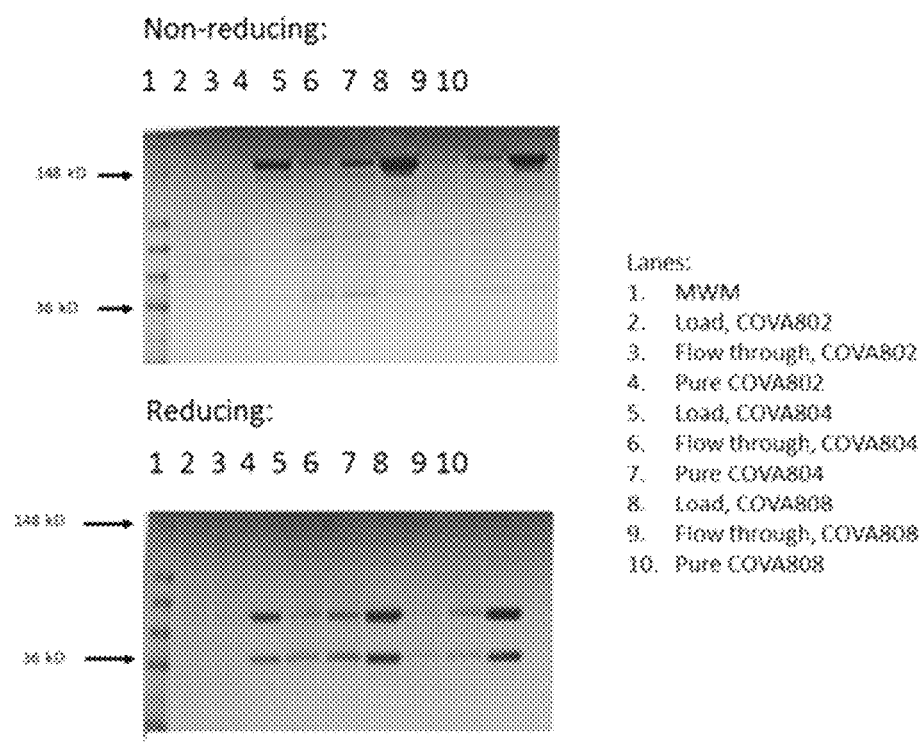

FIG. 3
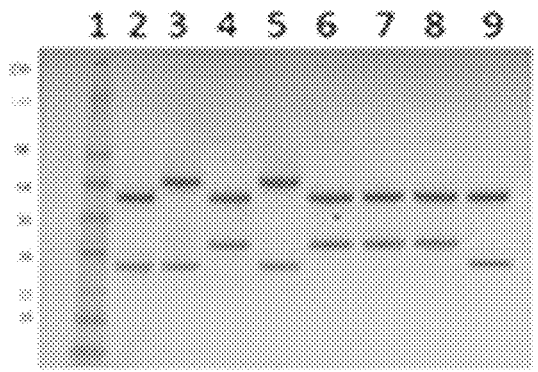
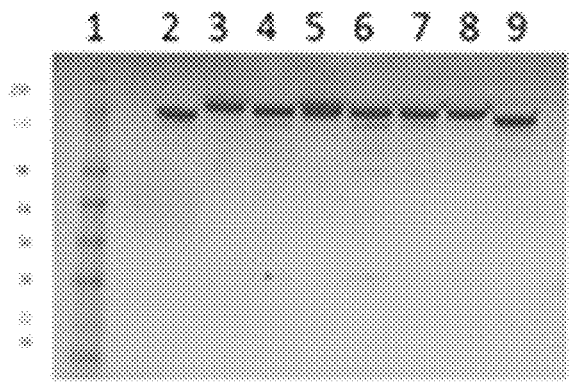
Lanes:
1. SeeBlue Plus 2
2. Actemra
3. COVA801
4. COVA802
5. COVA803
6. COVA804
7. COVA806
8. COVA808
9. Tocilizumab

COVA803

COVA804

COVA807

COVA808

Actemra (negative control)

tocilizumab (negative control, TRL lot)

tocilizumab (negative control)

COVA803

COVA804

COVA807

COVA808 secukinumab (negative control)

Actemra tocilizumab (TRL lot, positive control)

tocilizumab (positive control)

FIG. 8A    IL17A Inhibition HT29 cells
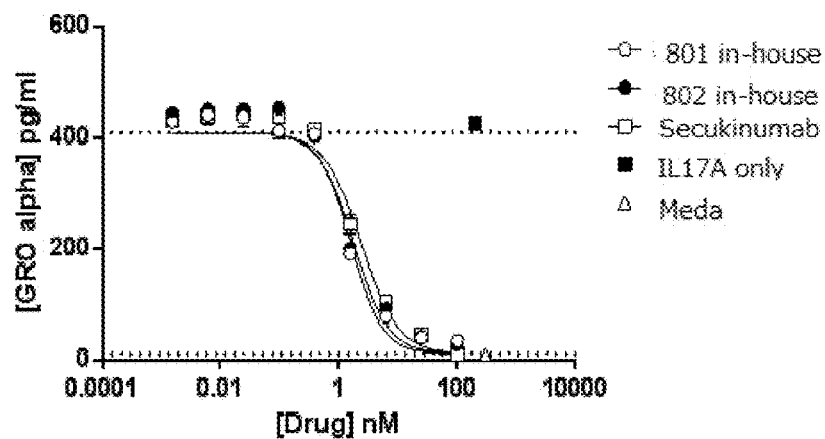
FIG. 8B    IL17A Inhibition HT29 cells
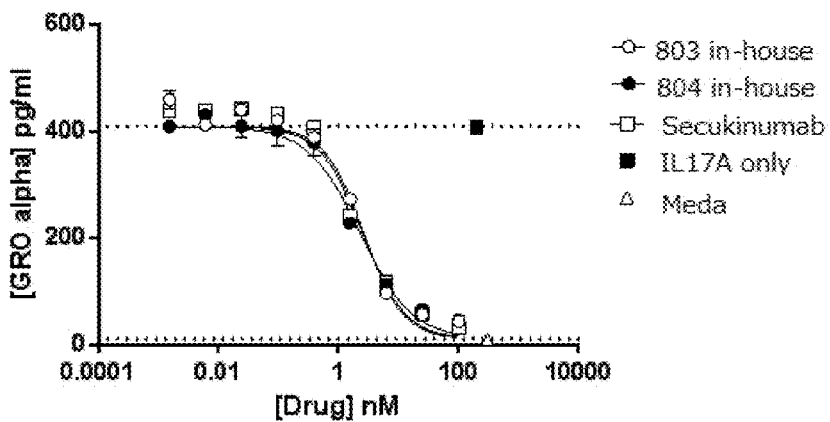

FIG. 8C     IL17A Inhibition HT29 cells
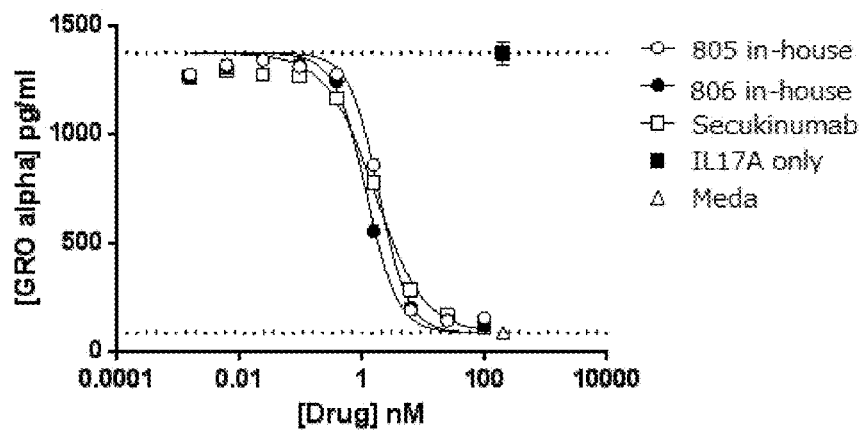
FIG. 8D     IL17A Inhibition HT29 cells
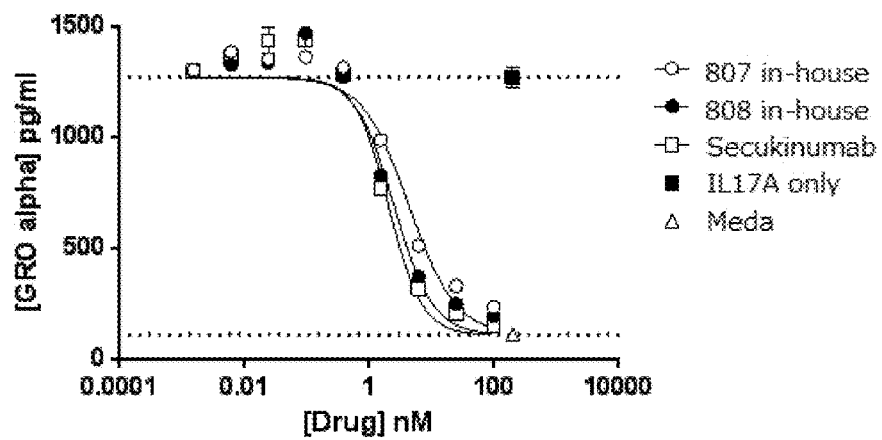

FIG. 9A   IL17A Inhibition HT29 cells
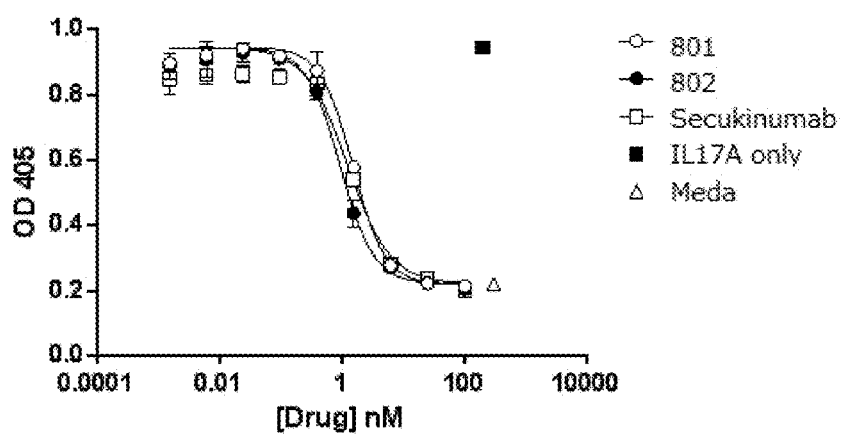
FIG. 9B   IL17A Inhibition HT29 cells
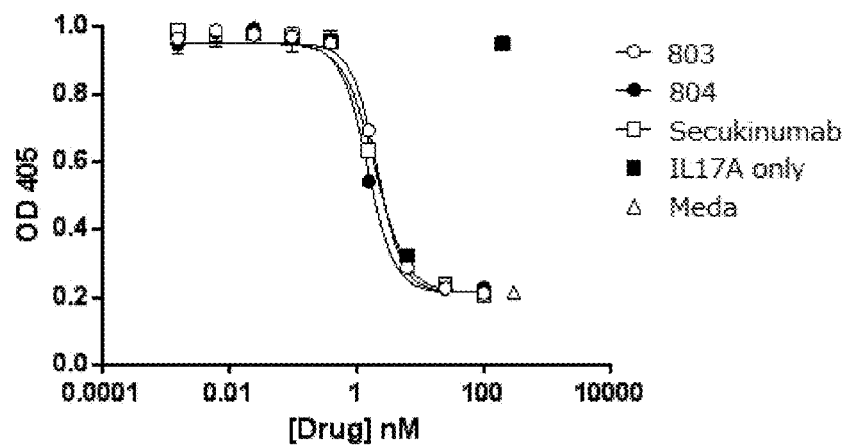

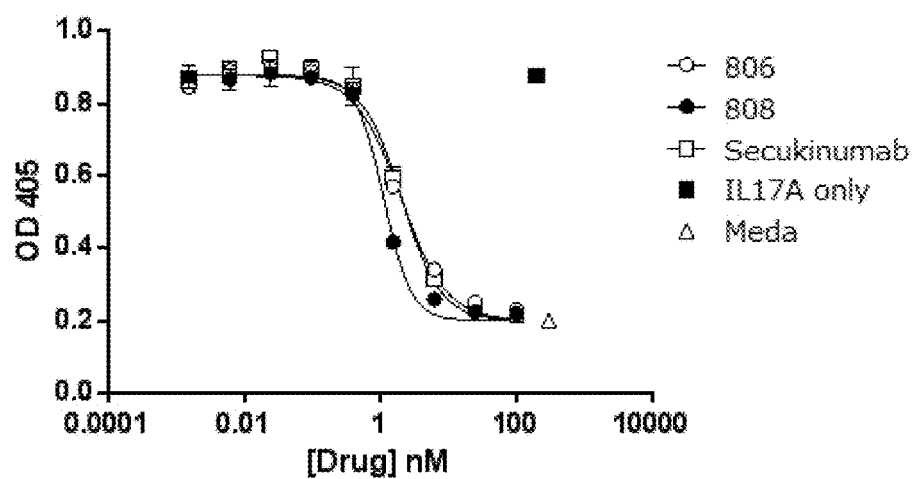
FIG. 9C   IL17A Inhibition HT29 cells

FIG. 16A    COVA801 + anti human IgG-Alexa488
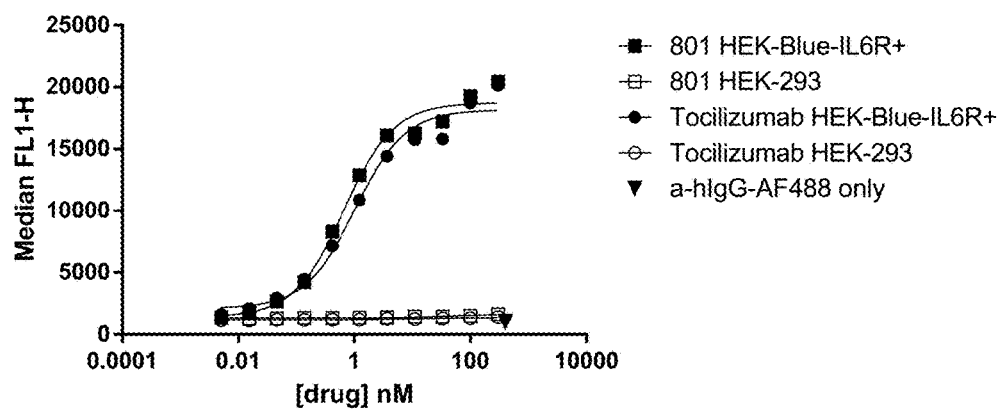
FIG. 16B    COVA801 + IL-17A-biotin + SA-APC
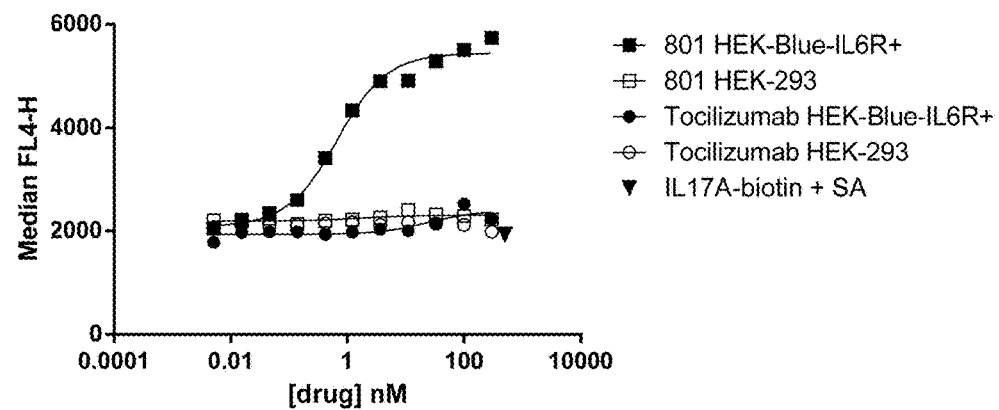

FIG. 16C    COVA802 + anti human IgG-Alexa488
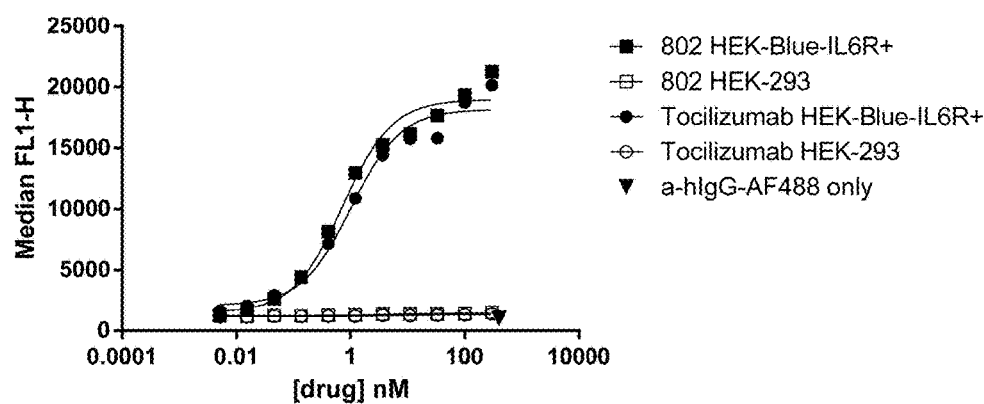
FIG. 16D    COVA802 + IL-17A-biotin + SA-APC
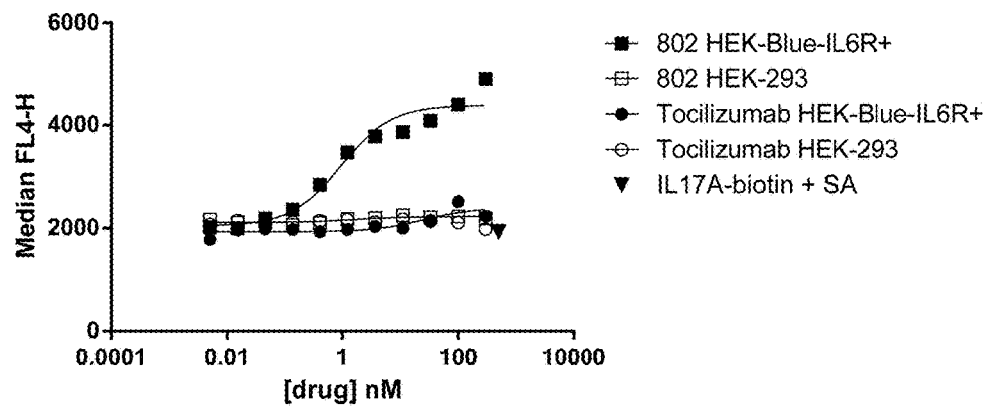

FIG. 16E    COVA803 + anti human IgG-Alexa488
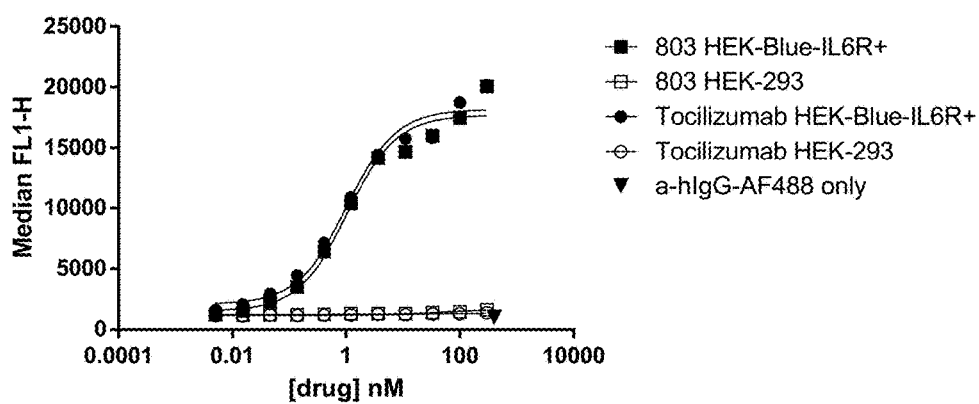
FIG. 16F    COVA803 + IL-17A-biotin + SA-APC
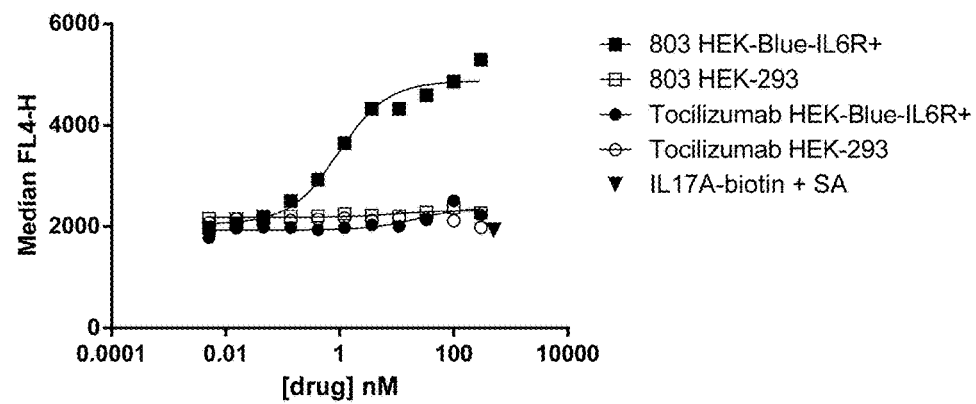

FIG. 16G  COVA804 + anti human IgG-Alexa488
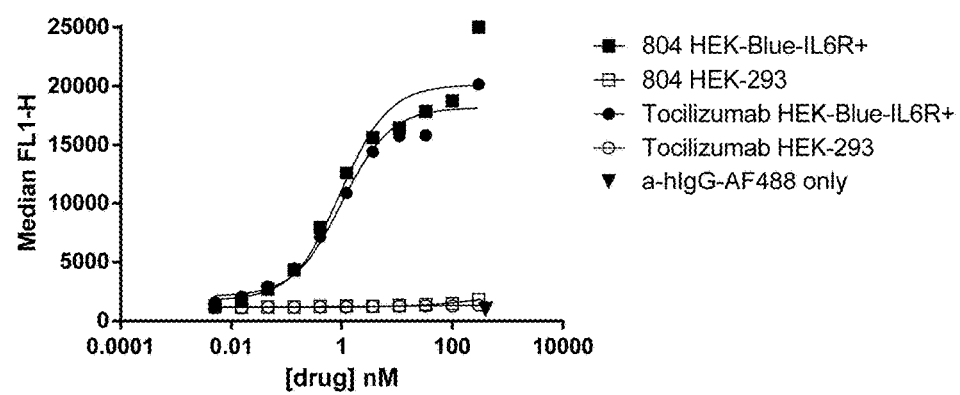
FIG. 16H  COVA804 + IL-17A-biotin + SA-APC
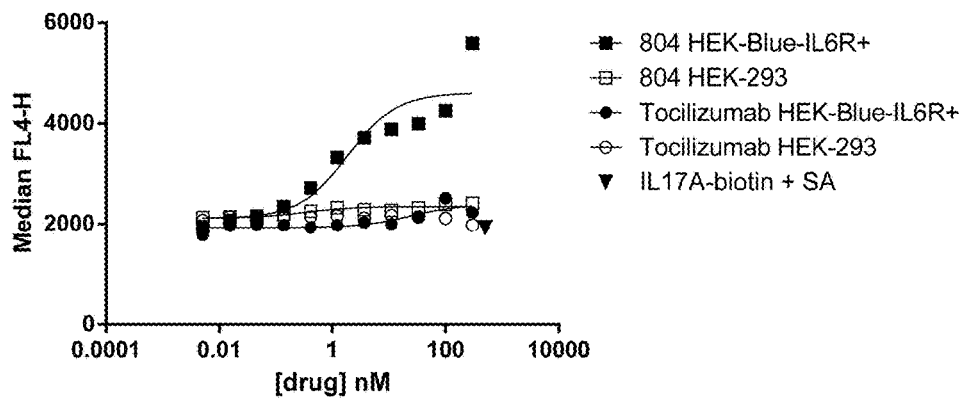

FIG. 16I  COVA805 + anti human IgG-Alexa488
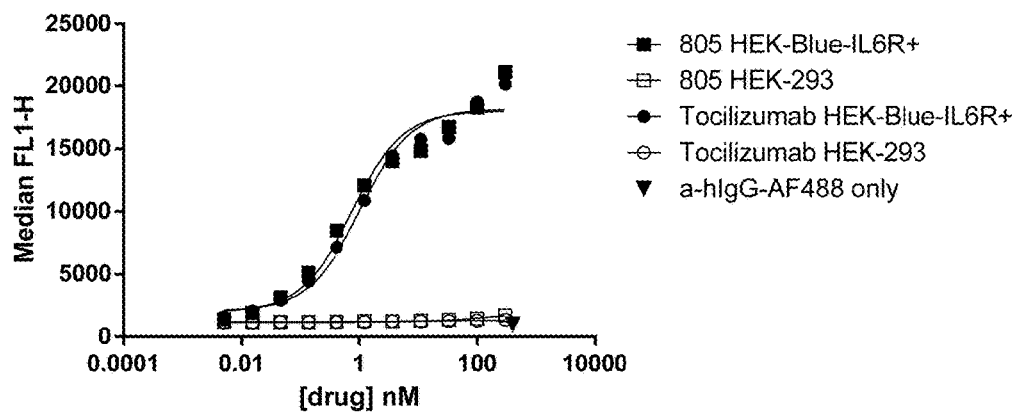
FIG. 16J  COVA805 + IL-17A-biotin + SA-APC
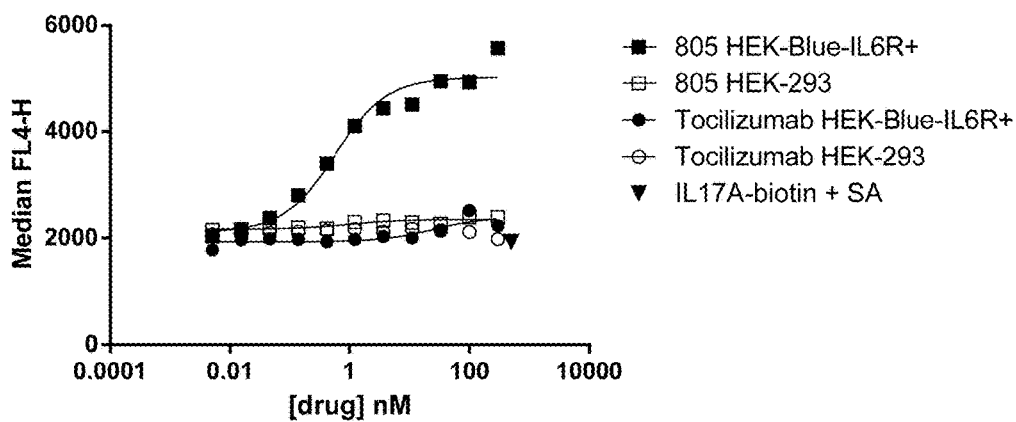

FIG. 16K  COVA806 + anti human IgG-Alexa488
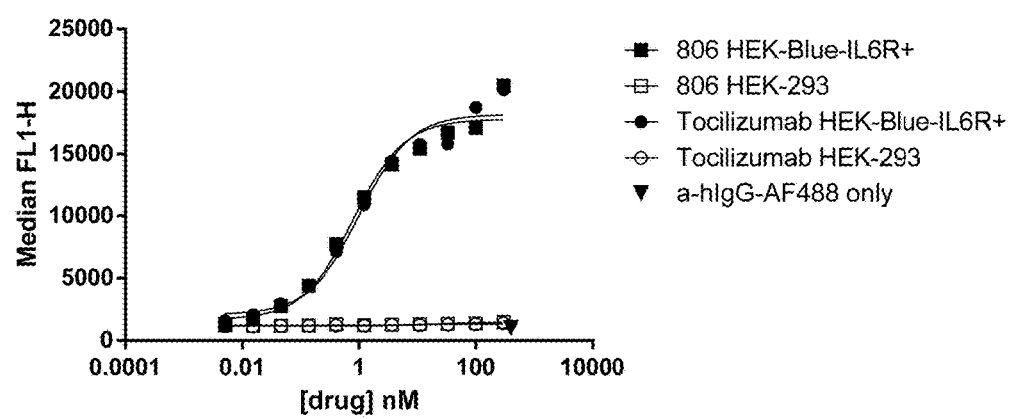
FIG. 16L  COVA806 + IL-17A-biotin + SA-APC
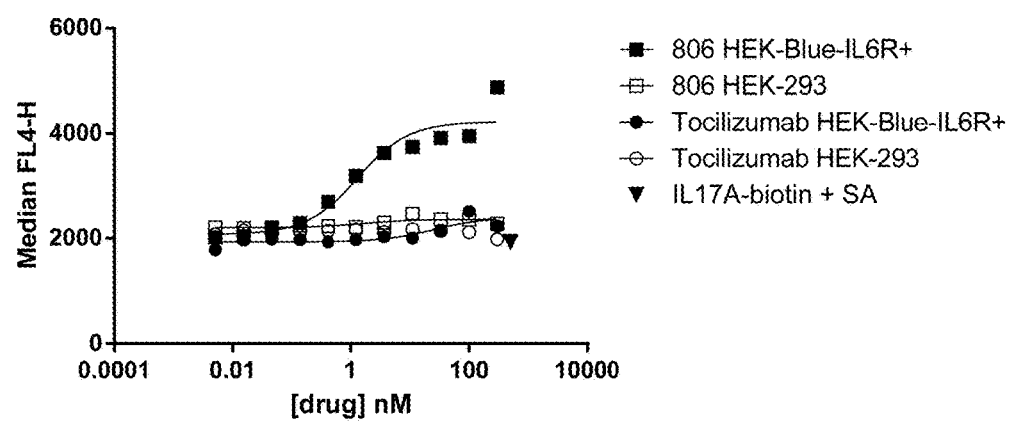

FIG. 16M    COVA807 + anti human IgG-Alexa488
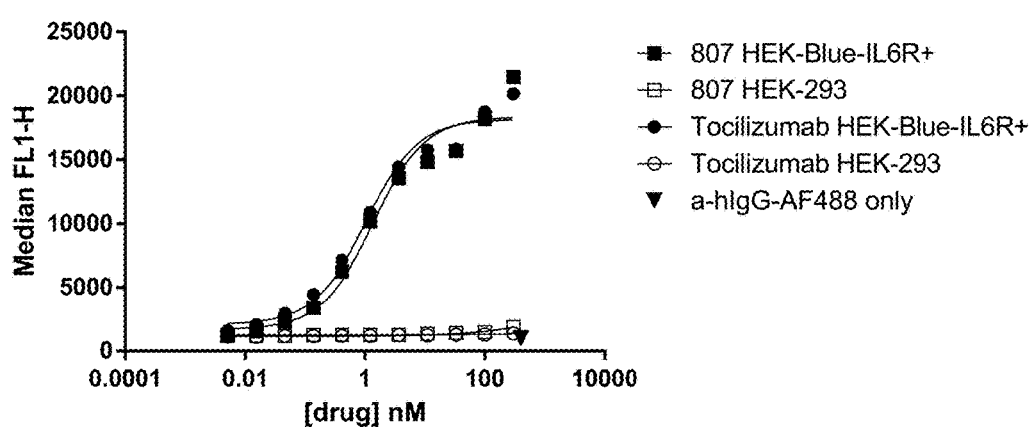
FIG. 16N    COVA807 + IL-17A-biotin + SA-APC
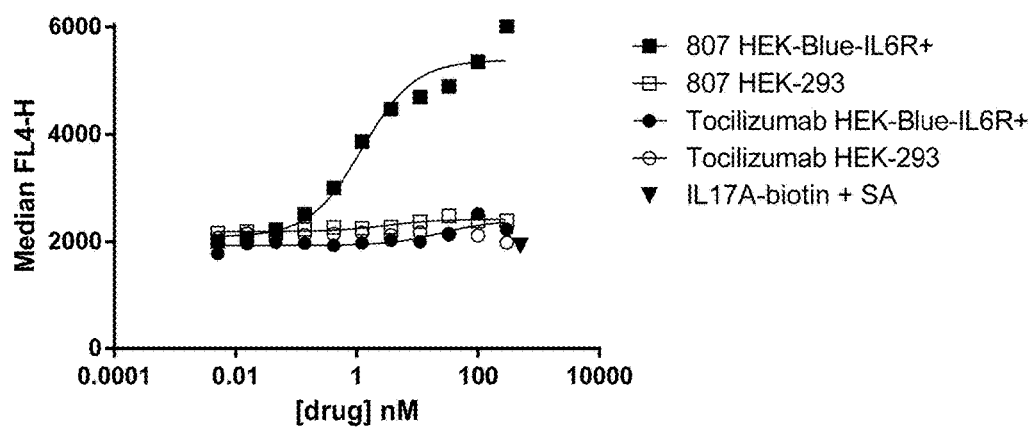

FIG. 16O   COVA808 + anti human IgG-Alexa488
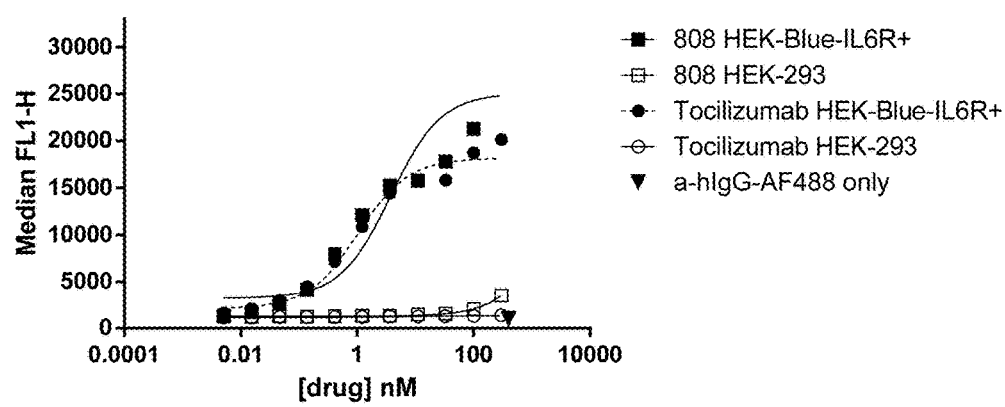
FIG. 16P   COVA808 + IL-17A-biotin + SA-APC
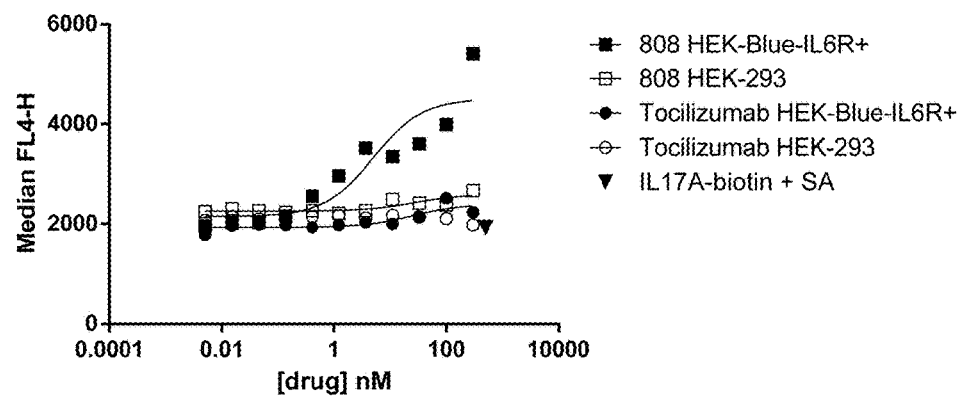

ANTIBODY-FYNOMER CONJUGATES

CROSS REFERENCES TO THE RELATED APPLICATIONS

This application is a U.S. National Stage of International Patent Application No. PCT/JP2015/058645, filed Mar. 16, 2015, entitled ANTIBODY-FYNOMER CONJUGATES, and naming inventors Roland Newman, Steve Granger, Michael Lyman, Dragan Grabulovski, Richard Woods, Michela Silacci, Wenjuan Zha, Isabella Attinger-Toller and Mutsumi Samejima, which published as International Patent Publication No. WO/2015/141862 on Sep. 24, 2015, and claims the priority of U.S. provisional patent application No. 61/954,437 filed Mar. 17, 2014. The entire content of the foregoing applications are incorporated herein by reference, including all text, tables and drawings.

TECHNICAL FIELD

The present invention relates to a fusion protein that can bind to both interleukin-17a (IL-17a) and interleukin-6 receptor (IL-6R). The present invention also relates to a transformed cell that produces the fusion polypeptide, a composition comprising the fusion polypeptide, and a method for treating a disease or disorder using the fusion polypeptide.

BACKGROUND ART

Th17 cells are central mediators in chronic inflammatory processes and principal pathogenic effectors in several types of autoimmunity conditions previously thought to be Th1-mediated (Weaver T. et al. (2008) Annu. Rev. Immunol., 25, p. 821-852). The pro-inflammatory cytokine IL-17 is mainly expressed by Th17 cells and is present at elevated levels in synovial fluid of patients with rheumatoid arthritis (RA) and has been shown to be involved in early RA development. In addition, IL-17 is a potent inducer of TNF-alpha and IL-1, the latter being mainly responsible for bone erosion and the very painful consequences for affected patients (Lubberts E. (2008) Cytokine, 41, p. 84-91). Furthermore, inappropriate or excessive production of IL-17 is associated with the pathology of various other diseases and disorders, such as osteoarthritis, loosening of bone implants, acute transplant rejection (Antonysamy et al., (1999) J. Immunol, 162, p. 577-584; van Kooten et al. (1998) J. Am. Soc. Nephrol., 9, p. 1526-1534), septicemia, septic or endotoxic shock, allergies, asthma (Molet et al. (2001) J. Allergy Clin. Immunol., 108, p. 430-438), bone loss, psoriasis (Teunissen et al. (1998) J. Invest. Dermatol, 111, p. 645-649), ischemia, systemic sclerosis (Kurasawa et al. (2000) Arthritis Rheum., 43, p. 2455-2463), stroke, and other inflammatory disorders. Consequently, a need exists for therapies that modulate the biological activities of IL-17.

Early neutralization of endogenous IL-17 by an IL-17 receptor-IgG1-Fc fusion protein starting after the immunization protocol during the initial phase of arthritis suppresses the onset of experimental arthritis (Lubberts et al. (2001) J. Immunol., 167, p. 1004-1013). Moreover, treatment with a neutralizing anti-IL-17 antibody in an animal model after the onset of collagen-induced arthritis reduced joint inflammation, cartilage destruction and bone erosion (Lubberts et al. (2004) Arthritis and Rheumatism, 50; 650-659). Histological analysis confirmed the suppression of joint inflammation, and systemic IL-6 levels were significantly decreased after treatment with an anti-IL-17 antibody. In contrast, systemic as well as local IL-17 overexpression using an adenoviral vector expressing murine IL-17 accelerated the onset of collagen-induced arthritis (CIA) and aggravated synovial inflammation at the site (Lubberts et al. (2001) J. Immunol., 167, p. 1004-1013 and Lubberts et al. (2002), Inflamm. Res. 51, p 102-104). More recently it could be demonstrated that the use of anti-IL-17 antibodies improved the clinical symptoms of psoriasis, rheumatoid arthritis and non-infectious uveitis (Leonardi C. et al. (2012) N. Engl. J. Med. 366, p. 1190-1199; Hueber W. et al. (2010) Sci Transl Med. 2(52):52ra72).

Interleukin 6 (IL-6) is a potent cytokine that regulates cell growth and differentiation, and is also an important mediator of acute inflammatory responses. IL-6 acts via a receptor complex consisting of a specific IL-6 receptor (IL-6R) and a signal transducing subunit (gp130). Dysregulated IL-6 signaling has been implicated in the pathogenesis of many diseases, such as multiple myeloma, autoimmune diseases and prostate cancer. Accordingly, there exists a need for therapies that modulate the biological activities of IL-6 and/or IL-6R.

SUMMARY OF THE INVENTION

It is an object of the present invention to provide a fusion polypeptide that can bind to both interleukin-17a (herein after, "IL-17a") and interleukin-6 receptor (hereinafter, "IL-16R"). It is another object of the present invention to provide a fusion polypeptide that can suppress, reduce, decrease, inhibit or block both IL-17a and IL-16R activities. It is still another object of the present invention to provide a transformed cell that produces the fusion polypeptide. It is further object of the present invention to provide a composition comprising the fusion polypeptide for treating a disease or disorder. It is still further object of the present invention to provide a method for treating a disease or disorder using the fusion polypeptide.

The inventors herein provide data showing that fusion polypeptides, namely FynomAbs comprising a fynomer sequence ("fyno," also referred to by Fynomer™) that binds to interleukin-17a (IL-17a) and is conjugated to an antibody or subsequence thereof ("mAb") that binds to interleukin-6 receptor (IL-6R) can bind to and suppress, reduce, decrease, inhibit or block both IL-17a and IL-6R function or activity. The data also show that different lots of exemplary FynomAbs produced at different times and from different cells behaved similarly across the lots. The exemplary 8 FynomAb constructs had very similar affinities for IL-17a and IL-6R and had similar functional activity in cell based assays. The light chain fusions (COVA802, COVA804, COVA806 and COVA808) had better SEC profiles and were less prone to aggregation.

In one embodiment, a bi-specific fusion polypeptide comprising a fynomer sequence that binds to interleukin-17a (IL-17a) and is conjugated to an antibody that binds to interleukin-6 receptor (IL-6R) or a subsequence of the antibody is provided. The bi-specific fusion polypeptide may be a fusion polypeptide that bind to IL-17a and bind to IL-6R simultaneously.

In one embodiment, the fynomer sequence may be conjugated to a heavy or light chain sequence of the antibody that binds to IL-6R or a subsequence of the heavy or light chain sequence. The fynomer sequence may be conjugated to the amino terminus or carboxyl terminus of a heavy chain sequence of the antibody or a subsequence thereof. The fynomer sequence may be conjugated to the amino terminus or the carboxyl terminus of a light chain sequence of the antibody or a subsequence thereof.

The bi-specific fusion polypeptide may include one or more of IL-17a binding sequences conjugated to the antibody that binds to IL-6R or a subsequence of the antibody. In particular embodiments, the bi-specific fusion polypeptide may include two or more, e.g., three, four, five, six, seven or eight IL-17a binding fynomer sequences that are conjugated to a IL-6R binding antibody or a subsequence thereof.

The IL-17a binding fynomer sequence may be those having various length. In one embodiment, the fynomer sequence is from about 10 to 80 amino acids in length.

The IL-17a binding fynomer sequence may be those having various affinities for IL-17a. In one embodiment, the fynomer sequence may have a binding affinity ($K_d$) for binding to IL-17a from about $10^{-9}$ M to about $10^{-13}$ M. In a preferred embodiment, the fynomer sequence may have a binding affinity ($K_d$) for binding to glycosylated IL-17a of about 1 to about 200 nM. In further preferred embodiment, the fynomer sequence may have a binding affinity ($K_d$) for binding to glycosylated human IL-17a from about 1 to about 200 nM, or from about 5 to about 50 nM. The fynomer sequence may have a comparable or greater binding affinity ($K_d$ or KD) for glycosylated IL-17a than binding affinity of the fynomer sequence of SEQ ID NO:1 for glycosylated IL-17a.

The IL-17a binding fynomer sequence may be those having identity to reference fynomer sequences. In particular embodiments, a fynomer sequence may be a sequence at least 90% or more (e.g., at least 91%, 92%, 93%, 94%, 95%, 96%, 97%, 98%, 99% or 100%) identical to any of the reference sequences as shown below:

(SEQ ID NO: 2)
GVTLFVALYDYKQKGHLDLSFHKGEKFQILSTHEYEDWWEARSLTTGETG

YIPSNYVAPVDSIQ; (aka 11L0-C6)

(SEQ ID NO: 3)
GVTLFVALYDYSARGQLDLSFHKGEKFQILSTHEYEDWWEARSLTTGETG

YIPSNYVAPVDSIQ; (aka 11L5-B06)

(SEQ ID NO: 5)
GVTLFVALYDYESVSWSDLSFHKGEKFQILSTHEYEDWWEARSLTTGETG

YIPSNYVAPVDSIQ; (aka 11L9-C09)

(SEQ ID NO: 6)
GVTLFVALYDYSSRGVLDLSFHKGEKFQILSTHEYEDWWEARSLTTGETG

YIPSNYVAPVDSIQ; (aka 11L10-A05)

(SEQ ID NO: 1)
GVTLFVALYDYANHGNRDLSFHKGEKFQILSTHEYEDWWEARSLTTGETG

YIPSNYVAPVDSIQ; (aka 1L3-B9)

(SEQ ID NO: 4)
GVTLFVALYDYDKLSALDLSFHKGEKFQILSTHEYEDWWEARSLTTGETG

YIPSNYVAPVDSIQ; (aka 11L6-F03)
and (SEQ ID NO: 7)
GVTLFVALYDYSRKSNLDLSFHKGEKFQILSTHEYEDWWEARSLTTGETG YIPSNYVAPVDSIQ. (aka 11L11-A09)

The IL-17a binding fynomer sequence may be those having amino acid substitutions, insertions, additions or deletions to the above reference fynomer sequences. In one embodiment, the fynomer sequence may be any of the following sequences:

(SEQ ID NO: 2)
GVTLFVALYDYKQKGHLDLSFHKGEKFQILSTHEYEDWWEARSLTTGETG

YIPSNYVAPVDSIQ;

(SEQ ID NO: 3)
GVTLFVALYDYSARGQLDLSFHKGEKFQILSTHEYEDWWEARSLTTGETG

YIPSNYVAPVDSIQ;

(SEQ ID NO: 5)
GVTLFVALYDYESVSWSDLSFHKGEKFQILSTHEYEDWWEARSLTTGETG

YIPSNYVAPVDSIQ;

(SEQ ID NO: 6)
GVTLFVALYDYSSRGVLDLSFHKGEKFQILSTHEYEDWWEARSLTTGETG

YIPSNYVAPVDSIQ;

(SEQ ID NO: 1)
GVTLFVALYDYANHGNRDLSFHKGEKFQILSTHEYEDWWEARSLTTGETG

YIPSNYVAPVDSIQ;

(SEQ ID NO: 4)
GVTLFVALYDYDKLSALDLSFHKGEKFQILSTHEYEDWWEARSLTTGETG

YIPSNYVAPVDSIQ;
and (SEQ ID NO: 7)
GVTLFVALYDYSRKSNLDLSFHKGEKFQILSTHEYEDWWEARSLTTGETG

YIPSNYVAPVDSIQ, or any of the foregoing sequences with 1-2, 2-3, 3-4, 5-6, 6-7, 7-8, 8-9, 9-10, 10-15, 15-20, 20-25 or 25-30 conservative, non-conservative, or conservative and non-conservative amino acid substitutions, or any of the foregoing sequences with 1-2, 2-3, 3-4, 5-6, 6-7, 7-8, 8-9, 9-10, 10-15, 15-20, 20-25 or 25-30 amino acid deletions or insertions.

In one embodiment, the IL-17a binding fynomer sequence may contain certain motif sequence identical to those contained in the reference fynomer sequences. In one embodiment, one or more of the motifs of GVTLFVALYDY (SEQ ID NO:35), DLSFHKGEKFQIL (SEQ ID NO:36), STHEYE (SEQ ID NO:37), STHEYED (SEQ ID NO:38), WWEAR (SEQ ID NO:39), DWWEAR (SEQ ID NO:40) and SLTTGETGYIPSNYVAPVDSIQ (SEQ ID NO:41) are included in the IL-17a binding fynomer sequence used in the present invention. In particular embodiment, the fynomer sequence may include the sequence STHEYE from amino acid positions 31-36 of the sequence, or the sequence QILSTHEYEDWWEAR (SEQ ID NO:42) from amino acid positions 28-42 of the sequence.

The IL-17a binding fynomer sequence may be those having a particular amino acid residue at a specified position or location. In particular, the fynomer sequence may have an E residue positioned immediately after the src loop sequence, and/or an E residue positioned immediately after the src loop sequence, STHEY.

The IL-17a binding fynomer sequence may be those having with particular activities or functions. In one embodiment, the fynomer sequence may bind to IL-17a and inhibit, decrease or suppress IL-17 receptor function or signaling. In further embodiment, the fynomer sequence may bind to glycosylated IL-17a and inhibit, decrease or suppress IL-17 receptor function or signaling. In yet further embodiment, the fynomer sequence may bind to glycosylated IL-17a and inhibit, decrease or suppress production of IL-6 by fibroblasts. For example, the fynomer sequence may have an $IC_{50}$ for inhibiting, decreasing or suppressing production of IL-6 by fibroblasts from about 10 to about 250 nM, or from about 10 to about 100 nM.

The bi-specific fusion polypeptide of the present invention comprises an antibody that binds to IL-6R or a subsequence of the antibody, such as VH or VL chain that binds to IL-6R. In one embodiment, the antibody or subsequence thereof may have a binding affinity $(K_d)$ for binding to IL-6R from about $10^{-5}$M to about $10^{-13}$M.

The IL-6R binding antibody or a subsequence thereof, such as VH or VL chain, may be those having various length. In particular, the sequence may be those having about 50 to 100 amino acids in length. In particular embodiments, the antibody or subsequence thereof may be an Fab, Fab', F(ab')$_2$, Fv, Fd, single-chain Fv (scFv), disulfide-linked Fvs (sdFv), $V_L$, $V_H$, diabody (($V_L$-$V_H$)$_2$ or ($V_H$-$V_L$)$_2$), triabody (trivalent), tetrabody (tetravalent), minibody ((scF$_v$-$C_H$3)$_2$), IgGdeltaCH2, scFv-Fc or (scFv)$_2$-Fc fragment.

The IL-6R binding antibody or a subsequence thereof may be those having various isotypes. In an embodiment, the antibody may be those having an IgG, IgA, IgE, IgM or IgD isotype.

The IL-6R binding antibody or subsequence thereof may be those having significant identity to reference sequences shown below. In particular embodiments, the antibody or subsequence thereof may be those having a sequence at least 90% or more (e.g., at least 91%, 92%, 93%, 94%, 95%, 96%, 97%, 98%, 99% or 100%) identical to any of the following heavy chain (HC) and light chain (LC) sequences:

(SEQ ID NO: 12)
(HC) QVQLQESGPGLVRPSQTLSLTCTVSGYSITSDHAWSWVRQPPGRGL

EWIGYISYSGITTYNPSLKSRVTMLRDTSKNQFSLRLSSVTAADTAVYYC

ARSLARTTAMDYWGQGSLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG;

(SEQ ID NO: 13)
(LC) DIQMTQSPSSLSASVGDRVTITCRASQDISSYLNWYQQKPGKAPKL

LIYYTSRLHSGVPSRFSGSGSGTDFTFTISSLQPEDIATYYCQQGNTLPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

The IL-6R binding antibody or subsequence thereof may be those having one or more amino acid substitutions, insertions, additions or deletions to one of reference sequences. In particular embodiments, an antibody or subsequence thereof may be any of the following heavy chain (HC) and light chain (LC) sequences:

(SEQ ID NO: 12)
(HC) QVQLQESGPGLVRPSQTLSLTCTVSGYSITSDHAWSWVRQPPGRGL

EWIGYISYSGITTYNPSLKSRVTMLRDTSKNQFSLRLSSVTAADTAVYYC

ARSLARTTAMDYWGQGSLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG;

(SEQ ID NO: 13)
(LC) DIQMTQSPSSLSASVGDRVTITCRASQDISSYLNWYQQKPGKAPKL

LIYYTSRLHSGVPSRFSGSGSGTDFTFTISSLQPEDIATYYCQQGNTLPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC, or those having 1-2, 2-3, 3-4, 5-6, 6-7, 7-8, 8-9, 9-10, 10-15, 15-20, 20-25, 25-30 conservative, non-conservative, or conservative and non-conservative amino acid substitutions, or amino acid insertions or deletions within or outside of the variable chain sequence of either of the foregoing heavy chain (HC) or light chain (LC) sequence.

The IL-6R binding antibody or subsequence thereof may be any of the following heavy chain (HC) and/or light chain (LC) sequences set forth as:

(SEQ ID NO: 14)
(HC) QVQLQESGPGLVRPSQTLSLTCTVSGYSITSDHAWSWVRQPPGRGL

EWIGYISYSGITTYNPSLKSRVTMLRDTSKNQFSLRLSSVTAADTAVYYC

ARSLARTTAMDYWGQGSLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGGGGGSGGGGSGGGGSGVTLFVALYDYKQKGHLDLSFHKGEKFQILSTH

EYEDWWEARSLTTGETGYIPSNYVAPVDSIQ;

(SEQ ID NO: 15)
(LC) DIQMTQSPSSLSASVGDRVTITCRASQDISSYLNWYQQKPGKAPKL

LIYYTSRLHSGVPSRFSGSGSGTDFTFTISSLQPEDIATYYCQQGNTLPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC (aka COVA 801);

(SEQ ID NO: 16)
(HC)QVQLQESGPGLVRPSQTLSLTCTVSGYSITSDHAWSWVRQPPGRGL
EWIGYISYSGITTYNPSLKSRVTMLRDTSKNQFSLRLSSVTAADTAVYYC
ARSLARTTAMDYWGQGSLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PG;

(SEQ ID NO: 17)
(LC)DIQMTQSPSSLSASVGDRVTITCRASQDISSYLNWYQQKPGKAPKL
LIYYTSRLHSGVPSRFSGSGSGTDFTFTISSLQPEDIATYYCQQGNTLPY
TFGQGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGECGGGGSGGGGSGGGGSGVTLFVALYDYKQKGHL
DLSFHKGEKFQILSTHEYEDWWEARSLTTGETGYIPSNYVAPVDSIQ
(aka COVA 802);

(SEQ ID NO: 18)
(HC)QVQLQESGPGLVRPSQTLSLTCTVSGYSITSDHAWSWVRQPPGRGL
EWIGYISYSGITTYNPSLKSRVTMLRDTSKNQFSLRLSSVTAADTAVYYC
ARSLARTTAMDYWGQGSLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PGGGGGSGGGGSGGGGSGVTLFVALYDYSARGQLDLSFHKGEKFQILSTH
EYEDWWEARSLTTGETGYIPSNYVAPVDSIQ;

(SEQ ID NO: 19)
(LC)DIQMTQSPSSLSASVGDRVTITCRASQDISSYLNWYQQKPGKAPKL
LIYYTSRLHSGVPSRFSGSGSGTDFTFTISSLQPEDIATYYCQQGNTLPY
TFGQGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC (aka COVA 803);

(SEQ ID NO: 20)
(HC)QVQLQESGPGLVRPSQTLSLTCTVSGYSITSDHAWSWVRQPPGRGL
EWIGYISYSGITTYNPSLKSRVTMLRDTSKNQFSLRLSSVTAADTAVYYC
ARSLARTTAMDYWGQGSLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PG;

(SEQ ID NO: 21)
(LC)DIQMTQSPSSLSASVGDRVTITCRASQDISSYLNWYQQKPGKAPKL
LIYYTSRLHSGVPSRFSGSGSGTDFTFTISSLQPEDIATYYCQQGNTLPY
TFGQGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGECGGGGSGGGGSGGGGSGVTLFVALYDYSARGQL
DLSFHKGEKFQILSTHEYEDWWEARSLTTGETGYIPSNYVAPVDSIQ
(aka COVA 804);

(SEQ ID NO: 22)
(HC)QVQLQESGPGLVRPSQTLSLTCTVSGYSITSDHAWSWVRQPPGRGL
EWIGYISYSGITTYNPSLKSRVTMLRDTSKNQFSLRLSSVTAADTAVYYC
ARSLARTTAMDYWGQGSLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PGGGGGSGGGGSGGGGSGVTLFVALYDYESVSWSDLSFHKGEKFQILSTH
EYEDWWEARSLTTGETGYIPSNYVAPVDSIQ;

(SEQ ID NO: 23)
(LC)DIQMTQSPSSLSASVGDRVTITCRASQDISSYLNWYQQKPGKAPKL
LIYYTSRLHSGVPSRFSGSGSGTDFTFTISSLQPEDIATYYCQQGNTLPY
TFGQGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC (aka COVA 805);

(SEQ ID NO: 24)
(HC)QVQLQESGPGLVRPSQTLSLTCTVSGYSITSDHAWSWVRQPPGRGL
EWIGYISYSGITTYNPSLKSRVTMLRDTSKNQFSLRLSSVTAADTAVYYC
ARSLARTTAMDYWGQGSLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PG;

(SEQ ID NO: 25)
(LC) DIQMTQSPSSLSASVGDRVTITCRASQDISSYLNWYQQKPGKAPKL

LIYYTSRLHSGVPSRFSGSGSGTDFTFTISSLQPEDIATYYCQQGNTLPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGECGGGGSGGGGSGGGGSGVTLFVALYDYESVSWS

DLSFHKGEKFQILSTHEYEDWWEARSLTTGETGYIPSNYVAPVDSIQ (aka COVA 806);

(SEQ ID NO: 26)
(HC) QVQLQESGPGLVRPSQTLSLTCTVSGYSITSDHAWSWVRQPPGRGL

EWIGYISYSGITTYNPSLKSRVTMLRDTSKNQFSLRLSSVTAADTAVYYC

ARSLARTTAMDYWGQGSLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGGGGGSGGGGSGGGGSGVTLFVALYDYSSRGVLDLSFHKGEKFQILSTH

EYEDWWEARSLTTGETGYIPSNYVAPVDSIQ;

(SEQ ID NO: 27)
(LC) DIQMTQSPSSLSASVGDRVTITCRASQDISSYLNWYQQKPGKAPKL

LIYYTSRLHSGVPSRFSGSGSGTDFTFTISSLQPEDIATYYCQQGNTLPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC (aka COVA 807);

(SEQ ID NO: 28)
(HC) QVQLQESGPGLVRPSQTLSLTCTVSGYSITSDHAWSWVRQPPGRGL

EWIGYISYSGITTYNPSLKSRVTMLRDTSKNQFSLRLSSVTAADTAVYYC

ARSLARTTAMDYWGQGSLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG;

(SEQ ID NO: 29)
(LC) DIQMTQSPSSLSASVGDRVTITCRASQDISSYLNWYQQKPGKAPKL

LIYYTSRLHSGVPSRFSGSGSGTDFTFTISSLQPEDIATYYCQQGNTLPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGECGGGGSGGGGSGGGGSGVTLFVALYDYSSRGVL

DLSFHKGEKFQILSTHEYEDWWEARSLTTGETGYIPSNYVAPVDSIQ (aka COVA 808), or those having 1-2, 2-3, 3-4, 5-6, 6-7, 7-8, 8-9, 9-10, 10-15, 15-20, 20-25, or 25-30 conservative, non-conservative, or conservative and non-conservative amino acid substitutions, or amino acid insertions or deletions within or outside of a variable chain sequence of either of the foregoing heavy chain (HC) or light chain (LC) sequence.

The IL-6R binding antibody may be a known IL-6R antibody such as Tocilizumab. The subsequence of the antibody may be a heavy chain or light chain of the antibody, or those having amino acid substitutions, insertions or deletions within or outside the variable region sequence of the heavy or light chain. The subsequence may also be those having amino acid substitutions, insertions or deletions within or outside a complementarity determining region (CDR) of the heavy or light chain variable region sequence of the antibody. The subsequence may also be those having amino acid substitutions, insertions or deletions within or outside the framework region (FR) of the heavy or the light chain variable region sequence of the known IL-6R binding antibody.

The IL-6R binding sequence may be those having particular activities or functions. In one embodiment, the IL-6R binding sequence binds to IL-6R and inhibits, decreases or suppresses IL-6R function or signaling.

According to the present invention, an IL-6R binding antibody, subsequence thereof, or VH or VL chain thereof and a fynomer sequence may be conjugated directly or by way of a linker. In one embodiment, conjugation may be by way of a covalent bond or an amide bond. In another embodiment, conjugation may be by way of a linker. Non-limiting examples of linkers may include peptides and carbon sequences. In one embodiment, a peptide sequence having about 1-5, 5-10, 10-15, 15-20, 20-25, 25-50 or 50-100 amino acid residues; and a carbon chain having about 1-5, 5-10, 10-15, 15-20, 20-25, 25-50 or 50-100 carbon atoms may be employed as a linker. Examples of linker peptides may be those including or consisting of a motif of (GGGGS (SEQ ID NO:43))$_X$ (X=1, 2, 3, 4, 5, 6, 7, 8, 9 or 10) or of GGGGSGGGGSGGGGS (SEQ ID NO:44).

Target sequences to which the bi-specific fusion polypeptide of the present invention binds include mammalian IL-17a and IL-6R. In particular embodiment, the target may be human IL-17a and/or IL-6R.

The bi-specific fusion polypeptide of the present invention may be provided as an isolated and/or purified polypeptide. The present invention also provides composition such as a pharmaceutical composition comprising the bi-specific fusion polypeptide of the invention. The composition may be a sterile pharmaceutical composition or formulation.

According to the present invention, transformed cells that produce the bi-specific fusion polypeptide of the present invention are also provided. The cell may be a prokaryotic or eukaryotic cell.

The bi-specific fusion polypeptide of the present invention may be used for the treatment of a disease or condition in a subject such as human. The disease or condition to be treated by this invention may include, but not limited to, autoimmune disease or disorder, and inflammation associated with or caused by an aberrant or undesirable immune response. In one embodiment, the bi-specific fusion polypeptide of the present invention is administered to a subject in need of the treatment of an autoimmune disease or disorder, or inflammation. Autoimmune diseases, disorders and inflammation may be those affecting any cell, tissue or organ in the subject. The autoimmune disease, disorder or inflammation to be treated by the bi-specific fusion polypeptide may be those affecting muscle, skeleton, neural system, connective tissue, endocrine system, skin, airway or pulmonary system, gastro-intestinal system, ocular system, or circulatory system.

The bi-specific fusion polypeptide of the present invention may be administered alone or co-administered with a second Or further agent that is useful for the treatment of the autoimmune disease or disorder, or inflammation to be treated by the bi-specific fusion polypeptide. In one embodiment, the bi-specific fusion polypeptide of the present invention may be administered before, simultaneously with, or after the administration of the second agent.

According to the present invention, a pharmaceutical composition for the treatment of a disease or disorder such as an autoimmune disease or disorder, or inflammation to be treated by the bi-specific fusion polypeptide comprising the bi-specific fusion polypeptide and a pharmaceutically acceptable carrier or diluent is also provided. The composition may further comprise a second or further agent that is useful for the treatment of the disease or condition to be treated by the bi-specific fusion polypeptide.

According to the present invention, use of the bi-specific fusion polypeptide for the manufacture of a pharmaceutical composition for the treatment of a disease or disorder, such as an autoimmune disease or disorder, or inflammation is also provided.

BRIEF DESCRIPTION OF DRAWINGS

FIG. 2A-2D shows SDS-PAGE analysis of stable CHO FynomAb material made for mouse PK study.

FIG. 3 shows SDS-PAGE analysis of stable CHO FynomAb material made for cynomolgus (cyno) PK study.

FIG. 8A-8D shows HT-29 IL-17A assay with stable CHO pool FynomAb material produced for mouse PK study.

FIG. 9A-9C shows HT-29 IL-17A assay with stable CHO pool FynomAb material produced for cynomolgus (cyno) PK study.

FIG. 16A-16P shows simultaneous binding of cell surface expressed IL-6R and soluble IL-17A.

DETAILED DESCRIPTION

Figure 1:
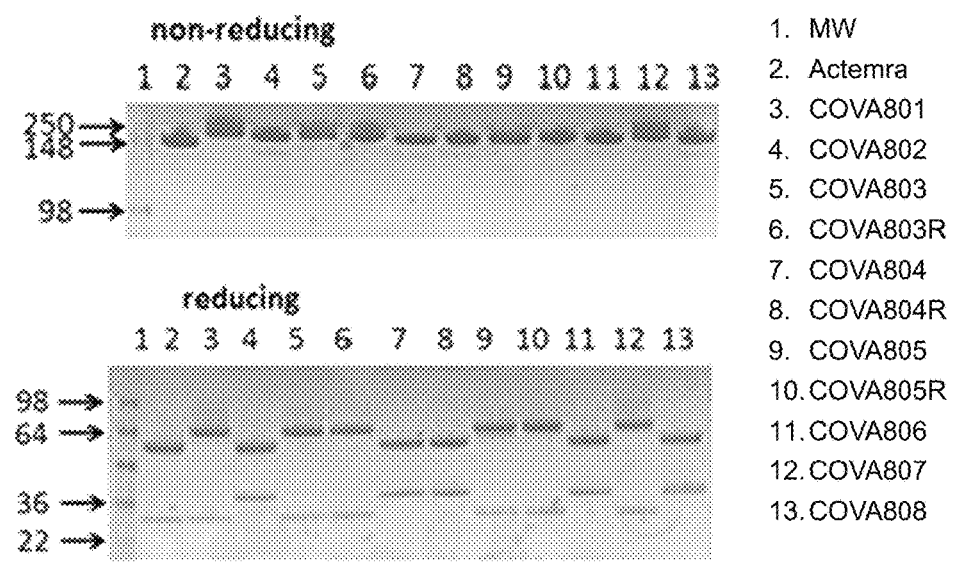
FIG. 1 shows SDS-PAGE analysis of transient CHO FynomAb material.

The term "fynomer" refers to a non-immunoglobulin derived binding (poly)peptide modeled after, based upon or derived from the human Fyn kinase SH3 domain, a so-called scaffold described in Gebauer and Skerra (2009) Curr Opinion in Chemical Biology 13:245-255). The SH3 domain of the human Fyn kinase may be used as a scaffold to engineer proteins (termed fynomers) that bind with high affinity and specificity to different targets, such as proteins (WO 2008/022759, WO 2011/023685, Grabulovski D. et al., (2007) J Biol Chem 282, p. 3196-3204, Bertschinger J. et al. (2007) Protein Eng Des Sel, 20, p. 57-68, and Schlatter et al. (2012) mAbs, 4(4) p. 497-50). The sequence of Fyn3 sequence, with respective RT loop (EARTED) and src loop (NSSE) regions underlined is shown below:

```
                                                             (SEQ ID NO: 45)
GVTLFVALYDYEARTEDDLSFHKGEKFQILNSSEGDWWEARSLTTGETGYIPSNYVAPVDSIQ
          RT loop              src loop
```

An "IL-17a fynomer" or "anti-IL-17a fynomer," and grammatical variations thereof, mean a fynomer sequence that binds to an interleukin 17a (IL-17a) protein. The amino acid positions within the RT loop and src-loop are believed to determine the binding specificity to the glycosylated IL-17A. Representative IL-17a binding fynomer sequences (SEQ ID NOs:1-7) are as follows:

```
            RT loop              src loop
SEQ ID NO 1:
GVTLFVALYDYANHGNRDLSFHKGEKFQILSTHEYEDWWEARSLTTGETG

YIPSNYVAPVDSIQ;

SEQ ID NO 2:
GVTLFVALYDYKQKGHLDLSFHKGEKFQILSTHEYEDWWEARSLTTGETG

YIPSNYVAPVDSIQ;

SEQ ID NO 3:
GVTLFVALYDYSARGQLDLSFHKGEKFQILSTHEYEDWWEARSLTTGETG

YIPSNYVAPVDSIQ;

SEQ ID NO 4:
GVTLFVALYDYDKLSALDLSFHKGEKFQILSTHEYEDWWEARSLTTGETG

YIPSNYVAPVDSIQ;

SEQ ID NO 5:
GVTLFVALYDYESVSWSDLSFHKGEKFQILSTHEYEDWWEARSLTTGETG

YIPSNYVAPVDSIQ;

SEQ ID NO 6:
GVTLFVALYDYSSRGVLDLSFHKGEKFQILSTHEYEDWWEARSLTTGETG

YIPSNYVAPVDSIQ;
and

SEQ ID NO 7:
GVTLFVALYDYSRKSNLDLSFHKGEKFQILSTHEYEDWWEARSLTTGETG

YIPSNYVAPVDSIQ.
```

An "IL-6R antibody" or "anti-IL-6R antibody," and grammatical variations thereof, mean a polyclonal or monoclonal antibody that binds to an interleukin 6 receptor (IL-6R) protein. Representative IL-6R binding antibody heavy chain and light chain sequences (SEQ ID NOs:8 and 9) are as follows:

```
Tocilizumab heavy chain sequence (SEQ ID NO: 8),
CDRs are underlined
  1 QVQLQESGPG LVRPSQTLSL TCTVSGYSIT SDHAWSWVRQ PPGRGLEWIG

51 YISYSGITTY NPSLKSRVTM LRDTSKNQFS LRLSSVTAAD TAVYYCARSL

101 ARTTAMDYWG QGSLVTVSSA STKGPSVFPL APSSKSTSGG TAALGCLVKD

151 YFPEPVTVSW NSGALTSGVH TFPAVLQSSG LYSLSSVVTV PSSSLGTQTY

201 ICNVNHKPSN TKVDKKVEPK SCDKTHTCPP CPAPELLGGP SVFLFPPKPK

251 DTLMISRTPE VTCVVVDVSH EDPEVKFNWY VDGVEVHNAK TKPREEQYNS

301 TYRVVSVLTV LHQDWLNGKE YKCKVSNKAL PAPIEKTISK AKGQPREPQV

351 YTLPPSREEM TKNQVSLTCL VKGFYPSDIA VEWESNGQPE NNYKTTPPVL

401 DSDGSFFLYS KLTVDKSRWQ QGNVFSCSVM HEALHNHYTQ KSLSLSPG*

Tocilizumab light chain sequence (SEQ ID NO: 9),
CDRs are underlined
  1 DIQMTQSPSS LSASVGDRVT ITCRASQDIS SYLNWYQQKP GKAPKLLIYY

51 TSRLHSGVPS RFSGSGSGTD FTFTISSLQP EDIATYYCQQ GNTLPYTFGQ

101 GTKVEIKRTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201 LSSPVTKSFN RGEC*
```

Additional examples of IL-6R binding antibodies, and/or heavy chain and light chain sequences of antibodies that bind to IL-6R, are described in US 20130122012; US 20120225060; US 20120128626; and US 20120077731. Nanobodies that bind to IL-6R are described in WO/2008/020079.

As used herein, the terms "IL-17a, "IL-17a protein," "IL-17a sequence," and "IL-17a domain" refer to all or a portion of an IL-17a protein sequence (e.g., a subsequence such as an antigenic region or epitope) isolated from, based upon or present in any naturally occurring context, or artificially produced (e.g., genetically engineered) IL-17a. Thus, the term IL-17a and the like include cellular as well as recombinantly or synthetically produced IL-17a sequences.

As used herein, the terms "IL-6R, "IL-6R protein," "IL-6R sequence," and "IL-6R domain" refer to all or a portion of an IL-6R protein sequence (e.g., a subsequence such as an antigenic region or epitope) isolated from, based upon or present in any naturally occurring context, or artificially produced (e.g., genetically engineered) IL-6R. Thus, the term IL-6R and the like include cellular as well as recombinantly or synthetically produced IL-6R sequences.

Mammalian IL-17a and IL-6R sequences are known to those skilled in the art. A representative non-limiting example of human IL-17a protein sequence (SEQ ID NO:10) is:

MTPGKTSLVSLLLLLSLEAIVKAGITIPRNPGCPNSEDKNFPRTVMVNLN

IHNRNTNTNPKRSSDYYNRSTSPWNLHRNEDPERYPSVIWEAKCRHLGCI

NADGNVDYHMNSVPIQQEILVLRREPPHCPNSFRLEKILVSVGCTCVTPI

VHHVA.

A representative non-limiting example of human IL-6R protein sequence (SEQ ID NO:11) is:

MLAVGCALLAALLAAPGAALAPRRCPAQEVARGVLTSLPGDSVTLTCPGV

EPEDNATVHWVLRKPAAGSHPSRWAGMGRRLLLRSVQLHDSGNYSCYRAG

RPAGTVHLLVDVPPEEPQLSCFRKSPLSNVVCEWGPRSTPSLTTKAVLLV

RKFQNSPAEDFQEPCQYSQESQKFSCQLAVPEGDSSFYIVSMCVASSVGS

KFSKTQTFQGCGILQPDPPANITVTAVARNPRWLSVTWQDPHSWNSSFYR

LRFELRYRAERSKTFTTWMVKDLQHHCVIHDAWSGLRHVVQLRAQEEFGQ

GEWSEWSPEAMGTPWTESRSPPAENEVSTPMQLTTNKDDDNILFRDSANA

TSLPVQDSSSVPLPTFLVAGGSLAFGTLLCIAIVLRFKKTWKLRALKEGK

TSMHPPYSLGQLVPERPRPTPVLVPLISPPVSPSSLGSDNTSSHNRPDAR

DPRSPYDISNTDYFFPR.

The term "antibody" refers to a protein that binds to another molecule (antigen) via heavy and light chain variable domains, denoted $V_H$ and $V_L$, respectively. "Antibody" refers to any polyclonal or monoclonal immunoglobulin molecule, or mixtures thereof, such as IgM, IgG, IgA, IgE, IgD. Antibodies belong to any antibody class or subclass. Exemplary subclasses for IgG are $IgG_1$, $IgG_2$, $IgG_3$ and $IgG_4$.

The term "monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

Antibodies include antibodies having kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa and two lambda light chains. The primary difference between kappa and lambda light chains is in the sequences of the constant region.

An antibody that includes or consists of a Heavy (H) chain and/or Light (L) chain or fragment of a Heavy (H) chain or Light (L) chain may include a single H or L chain or a single H or L chain fragment, or a plurality (2, 3, 4 or more) of Heavy (H) chains and/or Light (L) chains, or a plurality of fragments of Heavy (H) chains and/or Light (L) chains. A fusion polypeptide (FynomAb) that includes a Heavy (H) chain and/or Light (L) chain of an antibody or fragment may be but is not required to include 2 Heavy (H) chains and 2 Light (L) chains and therefore fusion polypeptides (Fynom-Abs) as set forth herein. An antibody or fragment thereof may be an oligomeric (higher order or valent) forms, such as a trimer, tetramer, pentamer, hexamer, heptamer, and so forth, with other antibodies, fragments thereof, Heavy (H) chain, Light (L) chain, or polypeptides distinct from an antibody Heavy (H) or Light (L) chain.

As used herein, the term "bi-specific" and grammatical variations thereof, when used in reference to a fusion polypeptide sequence, means that the fusion polypeptide binds to two distinct targets. Polypeptide targets are considered distinct when they have distinct amino acid sequences. The bi-specific fusion polypeptide of the present invention binds to interleukin 6 receptor (IL-6R) and interleukin-17a (IL-17a).

As used herein, the term "fusion" or "chimera" and grammatical variations thereof, when used in reference to a sequence, means that the sequence contains one or more portions that are based upon, derived from, or obtained or isolated from, two or more different proteins. That is, for example, a portion of the sequence may be based upon or from one particular protein, and another portion of the sequence may be based upon or from a different particular protein. Thus, a fusion or chimeric polypeptide is a molecule in which different portions of the polypeptide are of different protein origins.

The terms "protein," "polypeptide" and "peptide" are used interchangeably herein to refer to two or more amino acids, or "residues," covalently linked by an amide bond or equivalent. Amino acid sequences may be linked by non-natural and non-amide chemical bonds including, for example, those formed with glutaraldehyde, N-hydroxysuccinimide esters, bifunctional maleimides, or N, N'-dicyclohexylcarbodiimide (DCC). Non-amide bonds include, for example, ketomethylene, aminomethylene, olefin, ether, thioether and the like (see, e.g., Spatola in Chemistry and Biochemistry of Amino Acids, Peptides and Proteins, Vol. 7, pp 267-357 (1983), "Peptide and Backbone Modifications," Marcel Decker, NY).

The present invention provides a fusion polypeptide (FynomAbs) comprising a fynomer sequence that binds to interleukin-17a (IL-17a) and is conjugated to an antibody that binds to interleukin-6 receptor (IL-6R) or subsequence thereof that binds to IL-6R. The fynomer sequence may be bound to the amino- or carboxy-terminal end of the IL-6R binding antibody or subsequence thereof. Likewise, either the amino- or carboxy-terminal end of fynomer sequence may be bound to the amino- or carboxy-terminal end of the antibody or subsequence thereof. Multiple fynomers may be bound, via the amino- or carboxy-terminal end of the fynomer sequence, to multiple amino- or carboxy-terminal ends of the antibody or subsequence thereof. In addition, end-to-end or in series multiples of fynomers may be bound to the amino- or carboxy-terminal end of the antibody or subsequence thereof.

The term "bind," or "binding," when used in reference to a fynomer, an antibody or subsequence thereof, or a fusion polypeptide (e.g., FynomAb), means that the fynomer, the antibody or subsequence thereof, or the fusion polypeptide specifically binds to all or a part of a target. The fynomer, the antibody or subsequence thereof, or the fusion polypeptide (FynomAb) binds specifically or selectivity to IL-17a and/or IL-6R protein, which is selective for an epitope or antigenic determinant present in IL-17a or IL-6R protein. Selective binding refers to binding to a target protein. Binding to a non-target protein that does not significantly interfere with binding to the target protein is also considered selective. Selective binding may be distinguished from non-selective binding using specificity, affinity, and competitive and non-competitive binding assays, described herein or known in the art.

Fynomer/antibody fusion polypeptides (FynomAbs) of the invention may have the same or substantially the same binding specificity as the exemplified fynomers, antibodies and subsequences thereof. The affinity for a target may be more or less than that of a reference fynomer, antibody, or subsequence thereof, or a reference fynomer/antibody fusion polypeptide (FynomAb). A given FynomAb may or may not detectably compete with or inhibit binding of another fynomer, antibody, subsequence or FynomAb to regions of a target that do not interfere with each other.

A fynomer/antibody fusion polypeptide (FynomAb) that specifically binds to all or a part of sequence on a target may also bind to other proteins that have the same or a similar epitope as the target. Fusion polypeptides (FynomAbs) that bind to the same sequence or epitope or a part of the epitope can have more or less relative binding affinity or specificity for the target than a reference fynomer or antibody or fusion thereof.

Fynomers and antibodies, and fusion polypeptides (FynomAbs), also include sequences that compete for binding to their respective targets. Thus, for example, a given fynomer, antibody, subsequence or FynomAb may inhibit or compete for binding of another fynomer, antibody, subsequence or FynomAb for binding to IL-17a and/or IL-6R. In a particular non-limiting example, a fynomer, antibody, subsequence or FynomAb may inhibit binding to IL-17a and/or IL-6R by at least 30%, at least 35%, at least 40%, at least 45%, at least 50%, at least 55%, at least 60%, at least 65%, at least 70%, at least 75%, at least 80%, at least 85%, at least 90%, or at least 95%, or more of any of COVA801 to 808. Accordingly, the fynomer may be the one that competes for binding of any of the fynomers denoted as SEQ ID NOs:1-7 for binding to IL-17a (e.g., glycosylated IL-17a), and the antibody or subsequence thereof may be the one that competes for binding of an antibody comprising SEQ ID NOs:8 and 9 for binding to IL-6R.

FynomAbs of the invention may include fynomer/antibody or subsequence thereof or fusion polypeptide (FynomAb) with more or less affinity for target (e.g., IL-17a or IL-6R) than a reference fynomer/antibody or subsequence thereof or fusion polypeptide (FynomAb). For example, a FynomAb of the present invention may be those having more or less affinity for IL-17a (e.g., glycosylated IL-17a) and/or IL-6R and having a sequence at least 60% or more (e.g., at least 65%, 70%, 75%, 80%, 85%, 90%, 95%, 96%, 97%, 98% or 99%) identical to a fynomer sequence as set forth in SEQ ID NOs:1-7, or sequence at least 60% or more (e.g., at least 65%, 70%, 75%, 80%, 85%, 90%, 95%, 96%, 97%, 98% or 99%) identical to a heavy or light chain variable region sequence as set forth in SEQ ID NOs:8 or 9. In a particular embodiment, the fusion polypeptide (FynomAb) of the invention has greater affinity for glycosylated IL-17a than a fynomer sequence as set forth in SEQ ID NO:1.

FynomAbs of the invention therefore include sequences having the same or different binding affinity for IL-17a (e.g., glycosylated IL-17a) and/or IL-6R. For example, a FynomAb of the invention may have an affinity for target (e.g., glycosylated IL-17a and/or IL-6R) that is greater or less than 2-5, 5-10, 10-100, 100-1000 or 1000-10,000 fold affinity or any numerical value or range or value within such ranges, as another FynomAb, for example, COVA801-808.

Binding affinity may be determined by association ($K_a$) and dissociation ($K_d$) rate. Equilibrium affinity constant, KD, is the ratio of $K_a/K_d$. A fynomer or antibody having the same binding affinity as another fynomer or antibody, means that the dissociation constant ($K_d$) of each antibody is within about 1 to 10 fold (1-10 fold greater affinity or 1-10 fold less affinity, or any numerical value or range or value within such ranges, than the reference fynomer or antibody). Exemplary affinities for a target antigen (e.g., IL-17a such as glycosylated IL-17a, or IL-6R) have a dissociation constant ($K_d$) less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-8}$ M, $10^{-8}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{14}$ M, $10^{-14}$ M, $5 \times 10^{-15}$ M, and $10^{-15}$ M. Typically, binding affinities ($K_d$) for target may be less than $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, or $10^{-12}$ M.

More particular exemplary fynomer or fusion polypeptide (FynomAb) affinities for target antigen IL-17a (e.g., glycosylated IL-17a) have a KD of between about 0.01 nM to about 0.50 nM, or about 0.02 nM to about 0.40 nM. More particular exemplary antibody or subsequence thereof or fusion polypeptide (FynomAb) affinities for target antigen IL-6R have a KD of between about 0.20 nM to about 1.25 nM, or about 0.30 nM to about 1.10 nM.

Fynomers and antibodies, and fusion polypeptides (FynomAbs) may include those having at least a part of an "activity" or "function" as a reference fynomer, antibody, or a fusion comprising FynomAb. The activity or function may be binding affinity (e.g., $K_d$, KD), binding specificity, or activity, e.g., antagonist activity. The term "at least a part" means that the fynomer, antibody, or fusion polypeptide (FynomAb) retains at least a measurable or detectable amount of the activity or function of the reference fynomer, antibody, or the fusion polypeptide (FynomAb) exemplified herein. The fynomer, antibody, or fusion polypeptide (FynomAb) of the present invention may have a greater or less activity or function than the reference fynomer, antibody, or fusion polypeptide (FynomAb).

The fynomer, antibody, or fusion polypeptide (FynomAb) may have an antagonisting or agonisting activity or function. In one embodiment, the fynomer, antibody or fusion polypeptide (FynomAb) may be those having antagonisting or agonisting activity or function against IL-17a and/or IL-6R.

An "antagonist" is capable of decreasing, reducing, or inhibiting one or more activities of the target molecule, such as signaling by IL-17a or IL-6R. An antagonist may interfere with the binding of IL-17a to a receptor or IL-6R to a ligand, and incapacitates or kills cells activated by the ligand, and/or interfere with signal transduction. The antagonist may completely block, substantially decrease, reduce or inhibit interactions between the ligand and receptor.

An "agonist" is capable of increasing, inducing or activating one or more activities of a target molecule, such as signaling by IL-17a or IL-6R. Agonists may increase, induce or promote binding of a receptor to a ligand (or vice versa), or may act directly on the receptor or ligand to increase, induce, promote or activate signal transduction.

Fynomers, antibodies, or fusion polypeptides (FynomAbs) having an activity or function of a reference fynomer, antibody, or a fusion polypeptide (FynomAb) may be identified through various methods disclosed herein or known in the art. For example, binding assays against IL-17a (e.g., glycosylated IL-17a) or IL-6R on plates (ELISA), or on cells (cell based ELISA) may be employed. Specific inhibition of binding to IL-17a or IL-6R may be used as a measure of binding specificity as well as affinity. Examples of assays may be those can determine function or activity, such as IL-17a or IL-6R activity, e.g., signaling activity.

As set forth herein, an antibody, fynomer or fusion polypeptide (FynomAb) of the present invention may be those having one or more modifications in a reference sequence. Non-limiting examples of the modifications may include one or more amino acid substitutions (e.g., 1-3, 3-5, 5-10 or more residues), additions (e.g., 1-3, 3-5, 5-10 or more residues) or deletions (e.g., subsequences or fragments) of a reference fynomer, a reference antibody (heavy or light chain), or a fusion polypeptide (FynomAb). In particular embodiments, a modified fynomer, antibody, or fusion polypeptide (FynomAb) retains at least part of a function or an activity of unmodified reference antibody, fynomer or fusion polypeptide (FynomAb), e.g., binding affinity (e.g., $K_d$, KD) or binding specificity to IL-6R or IL-17a (e.g., glycosylated IL-17a), in vitro or in vivo or in or on a cell (e.g., in culture), or in vivo.

The fynomer, antibody or subsequence thereof or Fynom-Abs may include those having at least partial sequence identity (less than 100%) to a parental or reference fynomer, or antibody heavy or light chain variable region sequence, or fusion polypeptide (FynomAb) set forth herein respectively. For example, the fynomers set forth herein (SEQ ID NOs: 1-7), and/or heavy and light chain sequences of tocilizumab (SEQ ID NOs:8-9). The percent identity of such fynomer, antibody, subsequence thereof or fusion polypeptide (FynomAbs) may be as little as 60%, or may be more (e.g., 65%, 70%, 75%, 80%, 85%, 90%, 95%, 96%, 97%, 98% or 99%). The percent identity may extend over the entire sequence length of a sequence as set forth in SEQ ID NOs:1-9, or a contiguous region or area within any of SEQ ID NOs:1-9. In an aspect, the length of the sequence sharing the percent identity is 5 or more contiguous amino acids, e.g., 5, 6, 7, 8, 9, 10, 11, 12, 13, 14, 15, 16, 17, 18, 19 or 20 contiguous amino acids. In another aspect, the length of the sequence sharing the percent identity is 20 or more contiguous amino acids, e.g., 20, 21, 22, 23, 24, 25, 26, 27, 28, 29, 30, 31, 32, 33, 34 or 35 contiguous amino acids. In a further aspect, the length of the sequence sharing the percent identity is 35 or more contiguous amino acids, e.g., 35, 36, 37, 38, 39, 40, 41, 42, 43, 44, 45, 45, 47, 48, 49 or 50 contiguous amino acids. In yet further aspect, the length of the sequence sharing the percent identity is 50 or more contiguous aminoacids, e.g., 50-55, 55-60, 60-65, 65-70, 70-75, 75-80, 80-85, 85-90, 90-95, 95-100 or 100-110 contiguous amino acids.

In accordance with the invention, there are provided fusion polypeptides (FynomAbs) having any of fynomer sequence, heavy or light chain variable region of the antibody as set forth in SEQ ID NOs:1-9 or a sequence containing one or more amino acid substitutions in the sequence of SEQ ID NOs: 1-9. In an embodiment, the substituted fynomer and/or antibody heavy and/or light chain sequence may retain at least partial binding affinity and/or specificity to the target IL-17a (e.g, glycosylated IL-17a) and/or IL-6R.

In one embodiment, the fynomer sequence may have 1-15, 1-12, 1-8, 1-5, 1-3 or fewer (e.g., 1 or 2) amino acid substitutions. In particular, a substitution will be of an amino acid within any fynomer sequence (SEQ ID NOs:1-7).

In another embodiment, any substitution is not in a motif of GVTLFVALYDY (SEQ ID NO:35), DLSFHKGEKFQIL (SEQ ID NO:36), STHEY (SEQ ID NO:46), STHEYE (SEQ ID NO:37), STHEYED (SEQ ID NO:38), WWEAR (SEQ ID NO:39), DWWEAR (SEQ ID NO:40), SLTTGETGY-IPSNYVAPVDSIQ (SEQ ID NO:41), or QILSTHEYEDW-WEAR (SEQ ID NO:42) in the fynomer sequence. In another embodiment, the E amino acid residue positioned immediately after the src loop sequence in the fynomer sequence is not substituted.

The antibody or fusion polypeptide (FynomAb) may have one or more substitutions in the constant or variable (e.g., hypervariable, such as CDR or FR) region. One or a few amino acid substitutions in the constant or variable regions are likely to be tolerated. Non-conservative substitution of multiple amino acids in one or more hypervariable regions is likely affect binding activity, specificity of the antibody or fusion polypeptide (FynomAb).

Thus, modifications may include deleting small and large regions of amino acid sequences from the reference antibody, fynomer or fusion polypeptide (FynomAb). The deleted region may optionally be substituted with another amino acid sequence. The substituted sequence may be the same, or greater or shorter in length as the deleted region.

A particular example of an antibody or fusion polypeptide (FynomAb) modification is an alteration to have a different isotype or subclass, for example, by substitution of the heavy or light chain constant region. An alteration of Ig subclass can result in a change or an improvement in a function or activity (e.g., an anti-IL-6R activity, stability). Another example is an alteration that results in an improved characteristic, such as increased serum stability and/or half-life in vivo or PK. (e.g., as described in Antibody Engineering Vol. 1, Konterman R and Duebel S, eds., 2010, Springer, WO 2006/130834 and Horton et al., *Cancer Res* 68:8049 (2008)). Non-limiting examples of substitutions in the Fc include I253A, H310A, H435 R, H435Q, G236R, L328 R, S239D, I332E. Non-limiting examples of substitutions in IgG1 may be at residues 238, 252, 253, 254, 255, 256, 265, 272, 289, 288, 303, 305, 307, 309, 311, 312, 317, 340, 356, 360, 362, 376, 378, 380, 382, 386, 388, 400, 413, 415, 424, 433, 434, 435, 439 and/or 477 of the Fc region.

In an embodiment, a heavy or light chain CDR (CDR1, CDR2 or CDR3) or FR may have 1-15, 1-12, 1-8, 1-5, 1-3 or fewer (e.g., 1 or 2) amino acid substitutions. In an embodiment, the substitution within a variable region sequence may be a conservative amino acid substitution, e.g., within a CDR or FR. In another embodiment, the substitution within a variable region sequence may not be within a CDR. In another embodiment, the substitution may be within an FR. In another embodiment, the substitution within a variable region sequence may not be within an FR. Examples of heavy chain and light chain variable region CDR sequences that confer IL-6R binding are set forth in SEQ ID NOs:8 and 9, namely, heavy chain variable region CDRs1-3 are: SDHAWS (SEQ ID NO:47); YISYSGIT-TYNPSLKS (SEQ ID NO:48); and SLARTTAMDY (SEQ ID NO:49); and light chain variable region CDRs1-3 are:

```
RASQDISSYLN (SEQ ID NO: 50); YTSRLHS
  (SEQ ID NO: 51); and QQGNTLPYT (SEQ ID NO: 52).
```

The structural determinants that contribute to antigen binding by an antibody, such as complementarity determining regions (CDR) and framework regions (FR) within hyper variable regions are known in the art. The location, structure and function of additional regions, such as D- and J-regions are also known. An Antibody, subsequence thereof or a fusion polypeptide (FynomAb) that binds to a given target (e.g., IL-6R) may typically have one or more CDR and FR sequences with sufficient sequence identity to a heavy or light chain sequence that binds to IL-6R so as to retain at least partial function or IL-6R binding activity. For example, as exemplified herein, one or more CDRs of heavy or light chain sequence as set forth in SEQ ID NOs:8-9 may retain at least partial function or activity of an antibody that has binding specificity to IL-6R.

Regional mutability analysis may be used to predict the effect of particular substitutions in complementarity determining regions (CDR) and framework regions (FR) (Shapiro et al., *J Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) may be used to identify the nature of the antibody recognition domain and, therefore, amino acids that participate in ligand binding. Predictive models based upon QSAR may in turn be used to predict the effect of substitutions (mutations). For example, the effect of mutations on the association and dissociation rate of an antibody interacting with its antigen has been used to construct quantitative predictive models for both kinetic ($K_a$ and $K_d$) constants, which may in turn be used to predict the effect of other mutations on the antibody (De Genst et al., *J Biol. Chem.* 277:29897 (2002)). The skilled artisan can therefore use such analysis to predict amino acid substitutions that are likely to result in an antibody or subsequence that retains at least partial activity or function of non-substituted antibody, subsequence or fusion polypeptide (FynomAb), e.g., retains at least partial binding to IL-6R.

The effect of a given substitution may be assayed in order to identify antibodies and fusion polypeptides (FynomAbs) retaining at least a part of the binding activity, specificity or antibody function or activity of unsubstituted reference antibody or fusion polypeptide (FynomAb). For example, an amino acid substitution, addition, deletion or insertion in a hypervariable region of an antibody or fusion polypeptide (FynomAb) that binds to IL-6R may be assayed for IL-6R binding activity or binding specificity. Accordingly, antibodies and fusion polypeptides (FynomAbs) having amino acid substitutions, as well as additions, deletions and insertions are included so long as at least a part of a function or activity such as binding affinity, binding specificity, binding to a target (e.g., IL-6R) on a cell in vitro (e.g., in culture), or in vivo is at least partially retained.

The term "identity" and grammatical variations thereof, mean that two or more referenced entities are the same. Thus, where two amino acid sequences are identical, they have the same amino acid sequence. The identity may be over a defined area (region or domain) of the sequence. "Areas, regions or domains" of homology or identity mean that a portion of two or more referenced entities share homology or are the same. Thus, where two sequences are identical over one or more sequence regions they share identity in these regions.

Amino acid substitutions may be conservative or non-conservative. A "conservative substitution" means the replacement of one amino acid by a biologically, chemically or structurally similar residue. Biologically similar means that the substitution is compatible with biological activity, e.g., retains binding to IL-17a or IL-6R. Structurally similar means that the amino acids have side chains with similar length, such as alanine, glycine and serine, or similar size. Chemical similarity means that the residues have the same charge or are both hydrophilic or hydrophobic. Particular non-limiting examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Amino acid substitutions may be with the same amino acid, except a naturally occurring L-amino acid may be substituted with a D-amino acid. Modifications therefore include one or more D-amino acids substituted for L-amino acids, or mixtures of D-amino acids substituted for L-amino acids.

The extent of identity between two sequences may be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol. Biol.* 132:185 (2000); and Smith et al., *J. Mol. Biol.* 147:195 (1981)). Programs for quantitating protein structural similarity using Delaunay-based topological mapping have also been developed (Bostick et al., *Biochem. Biophys. Res. Commun.* 304:320 (2003)).

Modifications include changes to an activity or function of a reference composition (e.g., affinity or specific binding to IL-17a or IL-6R). Modified fynomers, antibodies and fusion polypeptides (FynomAbs) having altered characteristics, such as increased binding affinity, increased antagonist activity, may be produced using a method known in the art. For example, affinity maturation techniques may be used to improve antibody binding affinity (US 2004/0162413 A1; U.S. Pat. Nos. 6,656,467, 6,531,580, 6,590,079 and 5,955,358; Fiedler et al., Protein Eng. 15:931 (2002); Pancook et al., *Hybrid. Hybridomics* 20:383 (2001); Daugherty et al., *Protein Eng.* 11:825 (1998); Wu et al., *Proc. Nat'l Acad. Sci. USA* 95:6037 (1998); and Osbourn et al., *Immunotechnology* 2:181 (1996)).

Fynomers, antibodies and fusion polypeptides (FynomAbs) include subsequences (e.g., fragments) and modified forms (e.g., sequence variants) as set forth herein. A fynomer subsequence refers to a functional fragment or subsequence of a reference fynomer, e.g., a sequence having deletion of one or more amino acids of any of SEQ ID NOs:1-7. An "antibody" subsequence refers to a functional fragment or subsequence of an immunoglobulin. Non-limiting examples of antibody subsequences may include an Fab, Fab', F(ab')$_2$, Fv, Fd, single-chain Fv (scFv), disulfide-linked Fvs (sdFv), $V_L$, $V_H$, diabody (($V_L$-$V_H$)$_2$ or ($V_H$-$V_L$)$_2$), triabody (trivalent), tetrabody (tetravalent), minibody ((scF$_V$-C$_H$3)$_2$), IgGdeltaCH2, scFv-Fc or (scFv)$_2$-Fc fragment. In particular aspects, an Fab, Fab', F(ab')$_2$, Fv, Fd, single-chain Fv (scFv), disulfide-linked Fvs (sdFv) $V_L$, $V_H$, diabody (($V_L$-$V_H$)$_2$ or ($V_H$-$V_L$)$_2$), triabody (trivalent), tetrabody (tetravalent), minibody ((scF$_V$-C$_H$3)$_2$), IgGdeltaCH2, scFv-Fc and (scFv)$_2$-Fc subsequence. Such subsequences and fusion polypeptides (FynomAbs) may have at least a part of a sequence set forth in any of SEQ ID NOs:8 or 9 (e.g., one or more CDRs (CDR1-CDR3 of heavy or light chain variable region sequence) and/or FRs of SEQ ID NOs:8-9).

In particular aspects, a subsequence has substantially the same or has the same IL-17a or IL-6R binding affinity or IL-17a or IL-6R binding specificity, or one or more functions or activities of IL-17a binding fynomer or IL-6R binding antibody in vitro or in vivo, on a cell in vitro or in vivo. The terms "functional subsequence" and "functional fragment" when referring to a fynomer, antibody or fusion polypeptide (FynomAb) refers to a portion of a fynomer or antibody or fusion polypeptide (FynomAb) that retains at least a part of one or more functions or activities as an intact reference fynomer or antibody or fusion polypeptide (FynomAb), e.g., a fynomer that binds to IL-17a, an antibody that binds to IL-6R or a fusion polypeptide (FynomAb) that binds to IL-17a and IL-6R.

Antibody subsequences, including single-chain antibodies, may include all or a portion of heavy or light chain variable region(s) (e.g., CDR1, CDR2 or CDR3) alone or in combination with all or a portion of one or more of the following: hinge region, CH1, CH2, and CH3 domains. Also included are antigen-binding subsequences of any combination of heavy or light chain variable region(s) (e.g., CDR1, CDR2 or CDR3) with a hinge region, CH1, CH2, and CH3 domains.

Additional modifications of the bi-specific fusion polypeptides (FynomAbs) included in the invention are additions (derivatives)/insertions. Examples of additions may include an addition of a polypeptide sequence, which is an amino acid sequence having one or more molecules that is not normally present in a reference native (wild type) sequence is covalently attached to the sequence. A particular example of a peptide addition is one in which a second heterologous sequence, i.e., heterologous functional domain is attached (covalent or non-covalent binding) that confers a distinct or complementary function upon the bi-specific fusion polypeptide (FynomAb). Thus, the bi-specific fusion polypeptide (FynomAb) may include a heterologous domain, wherein the domain confers a distinct function, i.e. a heterologous functional domain. For example, an Fc region may be a chimera that includes portions of human IgG1 and IgG3 Fc regions.

Heterologous functional domains that can be employed in this invention are not restricted to amino acid residues or domains. Thus, a heterologous functional domain may consist of any of a variety of different types of small or large functional moieties. Such moieties may include nucleic acid, peptide, carbohydrate, lipids, small organic molecules/compounds, such as a drug (e.g., an anti-cell proliferative drug), a metal (gold, silver), or a radioisotope. Thus, in another embodiment, a FynomAb that is detectably labeled is provided here.

Non-limiting examples of heterologous domains may include purification or detection tags and labels. Specific examples of purification and detectable (detection) tags and labels may include enzymes (horseradish peroxidase, urease, catalase, alkaline phosphatase, beta-galactosidase, chloramphenicol transferase); enzyme substrates; ligands (e.g., biotin); receptors (avidin); radioactive isotopes/radionuclides (e.g., $C^{14}$, $S^{35}$, $P^{32}$, $P^{33}$, $H^3$, $I^{125}$, $I^{131}$, gallium-67 and 68, scantium-47, indium-111, and radium-223); T7-, polyhistidine, His-, myc-, HA- and FLAG-tags; electron-dense reagents; energy transfer molecules; paramagnetic labels; fluorophores (fluorescein, rhodamine, phycoerthrin); chromophores; chemi-luminescent (imidazole, luciferase); bio-luminescent agents; contrast agents (e.g., gadolinium; manganese; barium sulfate; an iodinated or noniodinated agent); an ionic agent or nonionic agent; magnetic and paramagnetic agents (e.g., iron-oxide chelate); nanoparticle; a prosthetic group (e.g., streptavidin/biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); or a bioluminescent material (e.g., luciferase, luciferin, aequorin). Enzymes are typically detected by their activity. For example, horseradish peroxidase is usually detected by its ability to convert a substrate such as 3,3-',5,5-'-tetramethylbenzidine (TMB) to a blue pigment, which may be quantified. Ligands may bind other molecules such as biotin, which may bind avidin or streptavidin, and IgG, which can bind protein A.

Additional non-limiting examples of detectable labels may include a radioactive material, such as a radioisotope, a metal or a metal oxide. Radioisotopes include radionuclides that emit alpha, beta or gamma radiation, such as one or more of: $^{3}H$, $^{10}B$, $^{18}F$, $^{11}C$, $^{14}C$, $^{13}N$, $^{18}O$, $^{15}O$, $^{32}P$, $^{33}P$, $^{35}S$, $^{35}Cl$, $^{45}Ti$, $^{46}Sc$, $^{47}Sc$, $^{51}Cr$, $^{52}Fe$, $^{59}Fe$, $^{57}Co$, $^{60}Cu$, $^{61}Cu$, $^{62}Cu$, $^{64}Cu$, $^{67}Cu$, $^{67}Ga$, $^{68}Ga$, $^{72}As$, $^{76}Br$, $^{77}Br$, $^{81m}Kr$, $^{82}Rb$, $^{85}Sr$, $^{89}Sr$, $^{86}Y$, $^{90}Y$, $^{95}Nb$, $^{94m}Tc$, $^{99m}Tc$, $^{97}Ru$, $^{103}Ru$, $^{105}Rh$, $^{109}Cd$, $^{111}In$, $^{113}Sn$, $^{113m}In$, $^{114}In$, $^{125}I$, $^{131}I$, $^{140}La$, $^{141}Ce$, $^{149}Pm$, $^{153}Gd$, $^{157}Gd$, $^{153}Sm$, $^{161}Tb$, $^{166}Dy$, $^{166}Ho$, $^{169}Er$, $^{169}Yb$, $^{175}Yb$, $^{177}Lu$, $^{186}Re$, $^{188}Re$, $^{201}Tl$, $^{203}Pb$, $^{211}At$, $^{212}Bi$ or $^{225}Ac$.

Still further non-limiting examples of detectable labels may include a metal or a metal oxide such as gold, silver, copper, boron, manganese, gadolinium, iron, chromium, barium, europium, erbium, praseodynium, indium, or technetium.

The drug that may be used as a heterologous domain that is attached to the antibody of fusion polypeptide (FynomAb) may be a cytotoxic agent. The term "cytotoxic agent" used in this context refers to a substance that decreases, inhibits, suppresses, reduces, interferes with or blocks the function, or growth, of cells and/or a substance that causes destruction of cells. The cytotoxic agent may be used to kill or inhibit the proliferation or replication of the target cells.

Examples of cytotoxic agents may include diptheria toxin, cholera toxin, ricin and mitomycin C. Additional examples include Calicheamicin, Duocarmycin, PBD, auristatins and dolastatins (U.S. Pat. Nos. 5,635,483 and 5,780,588); calicheamicin (U.S. Pat. Nos. 5,712,374, 5,714,586, 5,739,116, 5,767,285, 5,770,701, 5,770,710, 5,773,001, and 5,877, 296), Gemcitabine, Cisplatin, Doxorubicin, Irinotecan, BCNU, streptozoicin, vincristine and 5-fluorouracil (U.S. Pat. No. 5,770,710; see also, e.g., U.S. Pat. Nos. 4,362,663; 4,371,533; 5,475,092; 5,585,499; 5,846,545; and 6,333, 410).

Further examples of cytotoxic agents may include taxanes (e.g., Taxol) and maytansinoids. Examples of maytansinoids, which inhibit microtubule formation in mammalian cells, may include maytansinol and maytansinol analogs. Examples of maytansinol analogues include those having a modified aromatic ring, and those having modifications at other positions (see, e.g., maytansine and maytansinoids, such as maytansinol and C-3 maytansinol esters (U.S. Pat. No. 4,151,042); synthetic maytansinol and derivatives and analogues thereof (U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533).

The bi-specific fusion polypeptide FynomAb may have an addition or may be a derivative. For example the polypeptide may include a sugar residue, phosphate group, ubiquitin, fatty acid or lipid, or may be glycosylated, phosphorylated, acetylated, amidated or formylated. The polypeptide may be derivatized by a protecting/blocking group or any of numerous chemical modifications. Modification of the polypeptide may also be intra- or inter-molecular disulfide bond(s).

Linkers, such as amino acid or peptidimimetic sequences may be inserted between the fynomer and/or antibody sequence and the heterologous functional domain so that the two entities maintain, at least in part, the distinct function or activity. In an embodiment, a fynomer domain is joined to a Heavy (H) chain or Light (L) chain immediately after the last amino acid at the amino($NH_2$)-terminus or the carboxy (C)-terminus of the Heavy (H) chain or the Light (L) chain. Linkers may have one or more properties that include a flexible conformation, an inability to form an ordered secondary structure or a hydrophobic or charged character which could promote or interact with either domain. Examples of amino acids typically found in flexible protein regions may include Gly, Asn and Ser. Other near neutral amino acids, such as Thr and Ala, may also be used in the linker sequence. The length of the linker sequence may vary without significantly affecting the function or activity of the fusion protein (see, e.g., U.S. Pat. No. 6,087,329). In a particular aspect, a fynomer and an antibody heavy or light chain are joined by a peptide sequence having from about 1 to 25 amino acid residues.

Examples of linkers may also include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST). Linkers further include a linear carbon chain, such as $C_N$ (where N=1-100 carbon atoms, e.g., C, CC, CCC, CCCC, CCCCC, CCCCCC, CCCCCCC, CCCCCCCC).

It is understood that a fynomer, antibody or subsequence may have multiple (e.g., two or more) variations, modifications or labels. For example, a heavy or light chain sequence of an antibody may be coupled to biotin so that it can be detected with avidin as well as labeled with $I^{125}$ so that it provides detectable signal. Other permutations and possibilities are readily apparent to those of ordinary skill in the art, and are considered to be within the scope of the invention.

Examples of antibodies and fusion polypeptides (Fynom-Abs) may include mammalian, human, humanized, and primatized sequences. The term "human," in reference to an antibody means that the amino acid sequence is fully human origin. A "human antibody" therefore refers to an antibody having human immunoglobulin amino acid sequences, i.e., human heavy and light chain variable and constant regions that specifically bind to target. A "human IL-6R antibody" or "human anti-IL-6R antibody" therefore refers to an antibody having human immunoglobulin amino acid sequence and binds to IL-6R. That is, all of the antibody amino acids are human or can or do exist in a human antibody. Thus, for example, an antibody that is non-human may be made fully human by substituting the non-human amino acid residues with amino acid residues that can or do exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); and Chothia and Lesk *J. Mol. Biol.* 186:651 (1987)). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31: 169 (1994); and Padlan *Mol. Immunol.* 28: 489 (1991)). Human antibodies therefore include antibodies in which one or more amino acid residues have been substituted with one or more amino acids present in another human antibody.

The term "humanized" when used in reference to an antibody, means that the amino acid sequence of the antibody has non-human amino acid residues (e.g., mouse, rat, goat, rabbit, non-human primate, etc.) of one or more determining regions (CDRs) that specifically bind to the desired target (e.g., IL-6R) in an acceptor human immunoglobulin molecule, and one or more human amino acid residues in the Fv framework region (FR), which are amino acid residues that flank the CDRs. Human framework region residues of the immunoglobulin may be replaced with corresponding non-human residues. Residues in the human framework regions can therefore be substituted with a corresponding residue from the non-human. CDR donor antibody to alter, generally to improve, antigen affinity or specificity, for example. In addition, a humanized antibody may include residues, which are found neither in the human antibody nor in the donor CDR or framework sequences. For example, a framework substitution at a particular position that is not found in a human antibody or the donor non-human antibody may be predicted to improve binding affinity or specificity human antibody at that position.

Antibody framework and CDR substitutions based upon molecular modeling are known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., Nature 332:323 (1988)). Antibodies referred to as "primatized" are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

Fynomer and antibody subsequences may be prepared by genetic techniques including expression of all or a part of the fynomer or antibody coding sequence into a host cell. IL-6R binding antibodies may be generated using techniques including conventional hybridoma technology, recombinant, and phage display technologies, or a combination thereof (see U.S. Pat. Nos. 4,902,614, 4,543,439, and 4,411,993; see, also Monoclonal Antibodies, Hybridomas: A New Dimension in Biological Analyses, Plenum Press, Kennett, McKearn, and Bechtol (eds.), 1980, and Harlow et al., *Antibodies: A Laboratory Manual*, Cold Spring Harbor Laboratory Press, 2nd ed. 1988). IL-6R binding monoclonal antibodies may also be obtained by direct cloning of immunoglobulin sequences from animals, including primate or human subjects.

An animal such as mouse, rabbit, rat, sheep, cow or steer, sheep, goat, pig, horse, guinea pig, and primates including humans may be immunized with IL-6R in order to obtain an antibody that binds to IL-6R. Such animal may be a genetically modified non-human animal having human IgG gene loci (e.g., lambda or kappa light chain), which is capable of expressing human antibody. Transgenic animals with one or more human immunoglobulin genes (kappa or lambda) that do not express endogenous immunoglobulins are described, for example in, U.S. Pat. No. 5,939,598. Such animals may therefore be used to produce human antibodies. Non-limiting examples of the animals may include human transchromosomic KM Mice™ (Tomizuka et al., *Proc. Natl. Acad. Sci. USA* 97:722 (2000); and Ishida et al., *Cloning Stem Cells* 4:91 (2004)) which can produce human immunoglobulin genes (WO02/43478) and HAC mice (WO02/092812). Conventional hybridoma technology using splenocytes isolated from immunized animals that respond to the antigen and fused with myeloma cells may be used to obtain human monoclonal antibodies. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). An overview of the technology for producing human antibodies is described in Lonberg and Huszar (*Int. Rev. Immunol.* 13: 65 (1995)).

Fynomer and antibody subsequences may also be produced by proteolytic hydrolysis. An antibody, for example, may be digested with pepsin or papain. Antibody fragments produced by enzymatic cleavage with pepsin provide a 5S fragment denoted F(ab')$_2$. This fragment may be further cleaved using a thiol reducing agent to produce 3.5S Fab' monovalent fragments. Alternatively, an enzymatic cleavage using pepsin directly produces two monovalent Fab' fragments and the Fc fragment (see, e.g., U.S. Pat. Nos. 4,036,945 and 4,331,647; and Edelman et al., Methods Enzymol. 1:422 (1967)). Other methods of cleaving antibodies, such as separation of heavy chains to form monovalent light-heavy chain fragments, further cleavage of fragments, or other enzymatic or chemical cleavage may also be used. Single-chain Fvs and antibodies may be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988).

Antibodies may be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, Mol. Immunol. 31:169 (1994); and Padlan, *Mol. Immunol.* 28:489 (1991)) may be used to humanize antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Nucleic acids encoding fynomers, antibodies and fusion polypeptides (FynomAbs) are also provided. In one embodiment, a nucleic acid encodes a sequence at least 60% or more (e.g., at least 65%, 70%, 75%, 80%, 85%, 90%, 95%, 96%, 97%, 98%, 99%, or 100%) identical to any fynomer sequence that binds to IL-17a, for example, 60% or more identical to the nucleic acid sequence that encodes the polypeptide as set forth in SEQ ID NOs:1-7.

In another embodiment, a nucleic acid encodes a sequence at least 60% or more (e.g., 65%, 70%, 75%, 80%, 85%, 90%, 95%, 96%, 97%, 98%, 99% or 100%) identical to any heavy or light chain variable region sequence as set forth in SEQ ID NOs:8 or 9. In an additional embodiment, a nucleic acid encodes a sequence at least 60% or more (e.g., at least 65%, 70%, 75%, 80%, 85%, 90%, 95%, 96%, 97%, 98%, 99% or 100%) identical to any heavy or light chain variable region sequence of an antibody that binds to IL-6R, such as heavy or light chain sequence as set forth in SEQ ID NOs:8 or 9 that is fused or conjugated to any fynomer sequence that binds to IL-17a, for example, a sequence set forth in SEQ ID NOs:1-7. In a further embodiment, a nucleic acid encodes a sequence having one or more amino acid additions, deletions or substitutions of SEQ ID NOs:1-7, or SEQ ID NOs:8 or 9, or a fusion polypeptide comprising any of SEQ ID NOs:1-7 fused to any of SEQ ID NOs:8 or 9.

The terms "nucleic acid" and "polynucleotide" and the like refer to at least two or more ribo- or deoxy-ribonucleic acid base pairs (nucleotides) that are linked through a phosphodiester bond or equivalent. Nucleic acids include polynucleotides and polynucleosides. Nucleic acids include single, double or triplex, circular or linear, molecules. Exemplary nucleic acids include but are not limited to: RNA, DNA, cDNA, naturally occurring and non-naturally occurring nucleic acid, e.g., synthetic nucleic acid.

Nucleic acids may be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. In particular aspects, a nucleic acid sequence has a length about 10-20, 20-30, 30-50, 50-100, 100-150, 150-200, 200-250, 250-300, 300-400, 400-500, 500-1000 or 1000-2000, nucleotides, or any numerical value or range within or encompassing such lengths. Shorter polynucleotides are commonly referred to as "oligonucleotides" or "probes" of single- or double-stranded DNA. However, there is no upper limit to the length of such oligonucleotides.

The term "isolated," when used in relation to the components (e.g., fynomers, antibodies, heavy or light chains sequences, fusion polypeptides (FynomAbs), nucleic acids encoding same, etc.), means that the component is made by the hand of man or is separated, completely or at least in part, from their naturally occurring in vivo environment. Generally, an isolated component substantially free of one or more materials with which they normally associate in nature, for example, one or more protein, nucleic acid, lipid, carbohydrate, cell membrane. The term "isolated" does not exclude alternative physical forms of the component, such as multimers/oligomers, variants, modifications or derivatized forms, or forms expressed in host cells produced by the hand of man. The term "isolated" also does not exclude composition or formulation containing the component that is produced by the hand of man.

An "isolated" component may also be "purified" when it is free of most or all of the materials with which it typically associates in nature. Thus, an isolated fusion polypeptide (FynomAb) that also is substantially pure or purified does not include polypeptides or polynucleotides present among millions of other sequences, such as in a polypeptide library or nucleic acids in a genomic or cDNA library, for example. A "purified" component may be combined with one or more other molecules. Thus, "purified" does not exclude combinations of the components, such as combinations of FynomAbs (multiple FynomAbs), and FynomAbs in combination with other active agents or drugs.

Nucleic acids may be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or confers expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid may be inserted into a plasmid for propagation into a host cell and for subsequent genetic manipulation. A plasmid is a nucleic acid that may be propagated in a host cell; plasmids may optionally contain expression control elements in order to drive expression of the nucleic acid encoding fynomer, antibody (heavy or light chains) or fusion polypeptide (FynomAb) in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of fynomer, antibody (heavy or light chains) or fusion polypeptide (FynomAb).

Nucleic acids encoding fynomer, antibody (heavy or light chains) or fusion polypeptide (FynomAb) may be produced synthetically or using recombinant methods, or isolated from a cell such as a hybridoma. Isolated nucleic acids may be inserted into a suitable expression vector, and introduced into suitable host cells (e.g., CHO, plant and other cells) which may be cultured for the production of fynomer, antibody (heavy or light chains) or fusion polypeptide (FynomAb).

In accordance with the invention, there are provided host cells that express or are transformed with a nucleic acid that encodes a fynomer, antibody (heavy or light chains) or fusion polypeptide (FynomAb) of the invention. Host cells and progeny thereof may be stably or transiently transfected for expression of fynomer, antibody (heavy or light chains) or fusion polypeptide (FynomAb).

Host cells may include but are not limited to prokaryotic and eukaryotic cells such as bacteria, fungi (yeast), plant, insect, and animal (e.g., mammalian, including primate and human) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression.

The term "transformed" or "transfected" when use in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The cell(s) may be propagated so that the desired polypeptide is generated. The progeny of a transfected or transformed cell may not be identical to the parent cell, since there may be mutations that occur during replication.

The invention further provides a pharmaceutical composition comprising the bi-specific fusion polypeptide of the invention and a pharmaceutically or physiologically acceptable carrier, diluent or excipient. As used herein, the term "pharmaceutically acceptable" and "physiologically acceptable," when referring to a carrier, diluent or excipient may be a solvent (aqueous or non-aqueous), detergent, solution, emulsion, dispersion media, coating or isotonic and absorption promoting or delaying agent, that is compatible with pharmaceutical administration and with the other components in the composition. Pharmaceutical composition of the present invention may be provided in the form of tablet (coated or uncoated), capsule (hard or soft), microbead, emulsion, powder, granule, crystal, suspension, syrup or elixir.

A pharmaceutical composition may be formulated so that it is compatible with a particular route of administration or use. A pharmaceutical composition for parenteral, intradermal, or subcutaneous administration may contain a sterile diluent, such as water, saline solution, fixed oils, polyethylene glycols, glycerine, propylene glycol or other synthetic solvents. The composition may further contain one or more preservatives to prevent microorganism growth (e.g., antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose).

A pharmaceutical composition for injection may be in the form of sterile aqueous solution (where water soluble) or extemporaneous preparation for sterile injectable solution or dispersion consisting of a dispersion medium and sterile powders. For intravenous administration, examples of suitable carriers may include physiological saline, bacteriostatic water, Cremophor ELT™ (BASF, Parsippany, N.J.) and phosphate buffered saline (PBS). The carrier may be a solvent or dispersion medium containing, for example, water, ethanol, polyol (e.g., glycerol, propylene glycol, and polyetheylene glycol), or a suitable mixture thereof. Fluidity may be maintained, for example, by the use of a coating such as lecithin, or by the use of surfactants. Examples antibacterial and antifungal agents may include parabens, chlorobutanol, phenol, ascorbic acid and thimerosal. Including an agent that delays absorption, for example, aluminum monostearate and gelatin can prolong absorption of injectable compositions. Polysorbate 20 or polysorbate 80 may be added into the composition, for example, up to 1%. Other non-limiting examples of additives may include histidine HCl, α,α-treahlose dehydrate.

Additional pharmaceutical formulations and delivery systems are known to the skilled artisan and are applicable in the methods of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms, Technonic Publishing Co., Inc., Lancaster, Pa., (1993); and Poznansky, et al., Drug Delivery Systems, R. L. Juliano, ed., Oxford, N.Y. (1980), pp. 253-315).

The invention provides a method and use of the bi-specific fusion polypeptide for modulating or treating a response, disorder or disease associated with Il-17a and/or IL-6R function or activity. Examples of responses, disorders and diseases may include, without limitation, immune responses, disorders and diseases, inflammatory responses, disorders and diseases, and inflammation. Examples of responses, disorders and diseases also include, without limitation, autoimmune responses, disorders and diseases. Examples of responses may further include T cell and/or B cell responses, disorders and diseases.

In one embodiment, a method or use in which the bi-specific fusion polypeptide or the pharmaceutical composition as set forth herein is administered to a subject in need of the treatment for an immune response, disorder or disease, an inflammatory response, disorder or disease, or inflammation is provided. In another embodiment, a method or use for the treatment of an autoimmune disorder or disease is provided. In an additional embodiment, a method or use for modulating a T cell and/or B cell response, or for treating a disorder and disease associated with T cell and/or B cell response is provided. In a further embodiment, a method or use for modulating Il-17a and/or IL-6R function or activity is provided.

Examples of responses, disorders and diseases that can be modulated or treated in accordance with the invention may include, but are not limited to, acute and chronic undesirable or aberrant immune responses, disorders or diseases, inflammatory responses, disorders or diseases or inflammation. Examples of responses, disorders and diseases may also include, but are not limited to, acute and chronic autoimmune responses, disorders and diseases. The responses, disorders and diseases may be those mediated by antibody or cell, or a combination of antibody and cell. Furthermore, responses, disorders and diseases may be those mediated by Il-17a and/or IL-6R function or activity. Moreover, responses, disorders and diseases may be those amenable to treatment by modulating Il-17a and/or IL-6R function or activity.

In one embodiment, a method or use of the bi-specific fusion polypeptide for decreasing, reducing, inhibiting, suppressing, limiting or controlling an acute or chronic undesirable or aberrant immune response, disorder or disease, inflammatory response, disorder or disease or inflammation in a subject is provided. In an embodiment, a method or use for decreasing, reducing, inhibiting, suppressing, limiting or controlling an acute or chronic autoimmune response, disorder or disease in a subject is provided. In further embodiment, a method or use for decreasing, reducing, inhibiting, suppressing, limiting or controlling an acute or chronic antibody and/or cell mediated response, disorder or disease in a subject is provided. In a still further embodiment, a method or use for decreasing, reducing, inhibiting, suppressing, limiting or controlling an acute or chronic response, disorder or disease that is mediated by Il-17a and/or IL-6R function or activity is provided. In yet further embodiment, a method or use for decreasing, reducing, inhibiting, suppressing, limiting or controlling an acute or chronic response, disorder or disease that is amenable to treatment by modulating Il-17a and/or IL-6R function or activity is provided.

The terms "immune disorder" and "immune disease" mean an immune function or activity, which is characterized by different physiological symptoms or abnormalities, depending upon the disorder or disease. An "undesirable immune response" or "aberrant immune response" as used herein, refers to any immune response, activity or function that is greater or less than desired or physiologically normal response, activity or function. Examples include acute or chronic immune responses, activities or functions. "Undesirable immune response" is generally characterized as an undesirable or aberrant increased or inappropriate response, activity or function of the immune system. However, an undesirable immune response, function or activity may be a normal response, function or activity, for example. Thus, normal immune responses so long as they are undesirable, even if not considered aberrant, are included within the meaning of these terms. An undesirable immune response, function or activity can also be an abnormal response, function or activity. An abnormal (aberrant) immune response, function or activity deviates from normal.

One non-limiting example of an undesirable or aberrant immune response is where the immune response is hyper-responsive, such as in the case of an autoimmune disorder or disease. Another non-limiting example of an undesirable or aberrant immune response is where an immune response leads to acute or chronic inflammatory response or inflammation in any tissue or organ, such as in skeletal joints (rheumatoid arthritis, juvenile idiopathic arthritis), lung or airways (allergy), or gut or gastrointestinal tract (Crohn's disease, inflammatory bowel disease (IBD) or ulcerative colitis).

Undesirable or aberrant immune responses, inflammatory responses, inflammation are characterized by many different physiological adverse symptoms or complications, which may be humoral, cell-mediated or a combination thereof. Responses, disorders and diseases that may be treated in accordance with the invention include, but are not limited to, those that either directly or indirectly lead to or cause cell or tissue/organ damage in a subject. At the whole body, regional or local level, an immune response, inflammatory response, or inflammation may be characterized by swelling, pain, headache, fever, nausea, skeletal joint pain, swelling, stiffness or lack of mobility, rash, redness or other discoloration. At the cellular level, an immune response, inflammatory response, or inflammation may be characterized by one or more of T cell activation and/or differentiation, cell infiltration of the region by macrophages, monocytes, etc., production of antibodies, production of cytokines, lymphokines, chemokines, interferons and interleukins, cell growth and maturation factors (e.g., proliferation and differentiation factors), cell accumulation or migration and cell, tissue or organ damage. Thus, methods and uses of the invention include treatment of and an ameliorative effect upon any such physiological symptoms or cellular or biological responses characteristic of immune responses, inflammatory response, or inflammation.

Autoimmune responses, disorders and diseases are generally characterized as an undesirable or aberrant response, activity or function of the immune system characterized by increased or undesirable humoral or cell-mediated immune responsiveness or memory, or decreased or insufficient tolerance to self-antigens. Autoimmune responses, disorders and diseases that may be treated in accordance with the invention include but are not limited to responses, disorders and diseases that cause cell or tissue/organ damage in the subject.

In one embodiment, a method or use for decreasing, reducing, inhibiting, suppressing, limiting or controlling an undesirable or aberrant immune response, immune disorder, inflammatory response, or inflammation in a subject is provided. In another embodiment, a method or use for decreasing, reducing, inhibiting, suppressing, limiting or controlling an autoimmune response, disorder or disease in a subject is provided. In further embodiment, a method or use for decreasing, reducing, inhibiting, suppressing, limiting or controlling an adverse symptom of the undesirable or aberrant immune response, immune disorder, inflammatory response, or inflammation, or an adverse symptom of the autoimmune response, disorder or disease is provided.

In one aspect, the method or use according to the invention may result in a reduction in occurrence, frequency, severity, progression, or duration of a symptom of the condition (e.g., undesirable or aberrant immune response, immune disorder, inflammatory response, or inflammation). For example, the method or use of the invention may protect the subject from the progression of, or decrease, reduce, inhibit, suppress, limit or control, severity, frequency, duration or probability of an adverse symptom of the undesirable or aberrant immune response, immune disorder, inflammatory response, or inflammation, or an autoimmune response, disorder or disease.

Examples of adverse symptoms of an undesirable or aberrant immune response, immune disorder, inflammatory response, or inflammation, or an adverse symptom of an autoimmune response, disorder or disease may include swelling, pain, rash, discoloration, headache, fever, nausea, diarrhea, bloat, lethargy, skeletal joint stiffness or reduced mobility, difficulty with breathing, reduced muscle or limb mobility, paralysis, a sensory impairment, such as vision or tissue or cell damage. The adverse symptom may occur in particular tissues or organs, or regions or areas of the body, such as in skin, epidermal or mucosal tissue, gut, gastro-intestinal, bowel, genito-urinary tract, pancreas, thymus, lung, liver, kidney, muscle, central or peripheral nerves, spleen, skin, a skeletal joint (e.g., knee, ankle, hip, shoulder, wrist, finger, toe, or elbow), blood or lymphatic vessel, or a cardio-pulmonary tissue or organ. Additional examples of adverse symptoms of an autoimmune response, disorder or disease may include T cell production, survival, proliferation, activation or differentiation, and/or production of autoantibodies, or pro-inflammatory cytokines or chemokines (e.g., IL-17a and IL-6).

Non-limiting examples of aberrant or undesirable immune responses, disorders and diseases may include inflammatory responses, disorders and diseases, inflammation, autoimmune responses, disorders and diseases, treatable in accordance with the invention include: polymyositis, vasculitis syndrome, giant cell arteritis, Takayasu arteritis, relapsing, polychondritis, acquired hemophilia A, Still's disease, adult-onset Still's disease, amyloid A amyloidosis, polymyalgia rheumatica, Spondyloarthritides, Pulmonary arterial hypertension, graft-versus-host disease, autoimmune myocarditis, contact hypersensitivity (contact dermatitis), gastro-oesophageal reflux disease, erythroderma, Behçet's disease, amyotrophic lateral sclerosis, transplantation, Neuromyelitis Optica, rheumatoid arthritis, juvenile rheumatoid arthritis, malignant rheumatoid arthritis, Drug-Resistant Rheumatoid Arthritis, Neuromyelitis optica, Kawasaki disease, polyarticular or systemic juvenile idiopathic arthritis, psoriasis, chronic obstructive pulmonary disease (COPD), Castleman's disease, asthma, allergic asthma, allergic encephalomyelitis, arthritis, arthritis chronica progrediente, reactive arthritis, psoriatic arthritis, enterophathic arthritis, arthritis deformans, rheumatic diseases, spondyloarthropathies, ankylosing spondylitis, Reiter syndrome, hypersensitivity (including both airway hypersensitivity and dermal hypersensitivity), allergies, systemic lupus erythematosus (SLE), cutaneous lupus erythematosus, erythema nodosum leprosum, Sjögren's Syndrome, inflammatory muscle disorders, polychondritis, Wegener's granulomatosis, dermatomyositis, Steven-Johnson syndrome, chronic active hepatitis, myasthenia gravis, idiopathic sprue, autoimmune inflammatory bowel disease, ulcerative colitis, Crohn's disease, Irritable Bowel Syndrome, endocrine ophthalmopathy, scleroderma, Grave's disease, sarcoidosis, multiple sclerosis, primary biliary cirrhosis, vaginitis, proctitis, insulin-dependent diabetes mellitus, insulin-resistant diabetes mellitus, juvenile diabetes (diabetes mellitus type I), autoimmune haematological disorders, hemolytic anemia, aplastic anemia, pure red cell anemia, idiopathic thrombocytopenia (ITP), autoimmune uveitis, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, inflammatory disease of skin, cornea inflammation, myositis, loosening of bone implants, metabolic disorder, atherosclerosis, dislipidemia, bone loss, osteoarthritis, osteoporosis, periodontal disease of obstructive or inflammatory airways diseases, bronchitis, pneumoconiosis, pulmonary emphysema, acute and hyperacute inflammatory reactions, acute infections, septic shock, endotoxic shock, adult respiratory distress syndrome, meningitis, pneumonia, cachexia wasting syndrome, stroke, herpetic stromal keratitis, dry eye disease, iritis, conjunctivitis, keratoconjunctivitis, Guillain-Barre syndrome, Stiff-man syndrome, Hashimoto's thyroiditis, autoimmune thyroiditis, encephalomyelitis, acute rheumatic fever, sympathetic ophthalmia, Goodpasture's syndrome, systemic necrotizing vasculitis, antiphospholipid syndrome, Addison's disease, pemphigus vulgaris, pemphigus foliaceus, dermatitis herpetiformis, atopic dermatitis, eczematous dermatitis, aphthous ulcer, lichen planus, autoimmune alopecia, Vitiligo, autoimmune hemolytic anemia, autoimmune thrombocytopenic purpura, pernicious anemia, sensorineural hearing loss, idiopathic bilateral progressive sensorineural hearing loss, autoimmune polyglandular syndrome type I or type II, immune infertility or immune-mediated infertility.

The term "contacting" means direct or indirect interaction between two or more entities (e.g., between a fusion polypeptide (FynomAb) and a target, such as IL-17a and/or IL-6R). A particular example of direct interaction is binding. Contacting as used herein may be contacting in solution, in solid phase, in vitro, ex vivo, in a cell or in vivo. Contacting in vivo may be referred to as administering, administration, to administer, delivering or delivery to a subject or patient.

In the method or use of the present invention, the fusion polypeptide or composition as set forth herein may be administered prior to, substantially contemporaneously with, or following an onset of undesirable or aberrant immune response, immune disorder, inflammatory response, or inflammation, or an autoimmune response, disorder or disease, or one or more adverse symptoms, disorders, illnesses, pathologies, diseases, or complications caused by or associated with the foregoing. Thus, the method or use of the invention may be practiced prior to (i.e. prophylaxis), concurrently with or after an evidence of the response, disorder or disease begins, or one or more adverse symptoms, disorders, illnesses, pathologies, diseases, or complications caused by or associated with the undesirable or aberrant immune response, immune disorder, inflammatory response, inflammation or an autoimmune response, disorder or disease. Administering the fusion polypeptide or composition as set forth herein prior to, concurrently with or immediately following development of an adverse symptom may decrease, reduce, inhibit, suppress, limit or control the occurrence, frequency, severity, progression, or duration of one or more adverse symptoms, disorders, illnesses, pathologies, diseases, or complications caused by or associated with the undesirable or aberrant immune response, immune disorder, inflammatory response, inflammation or autoimmune response, disorder or disease.

According to the method or use of the present invention, the bi-specific fusion polypeptide of the present invention may be formulated and/or administered in combination with a second agent, such as an immunosuppressive, anti-inflammatory, or palliative agent. The fusion polypeptide of the present invention may be administered prior to, substantially contemporaneously with or following administering the second agent, such as an immunosuppressive, anti-inflammatory, or palliative agent. The fusion polypeptide of the present invention may be formulated in combination with the second agent such as an immunosuppressive, anti-inflammatory, or palliative agent.

Non-limiting examples of the second agents may include anti-inflammatory agents, such as steroidal and non-steroidal anti-inflammatory drugs (NSAIDs) and anti-inflammatory biologics such as antibodies that limit or control inflammatory responses or symptoms. Second agents and drugs include immunosuppressive corticosteroids (steroid receptor agonists) such as budesonide, prednisone, flunisolide; anti-inflammatory agents such as flunisolide hydrofluoroalkane, estrogen, progesterone, dexamethasone and loteprednol; beta-agonists (e.g., short or long-acting) such as bambuterol, formoterol, salmeterol, albuterol; anticholinergics such as ipratropium bromide, oxitropium bromide, cromolyn and calcium-channel blocking agents; antihistamines such as terfenadine, astemizole, hydroxyzine, chlorpheniramine, tripelennamine, cetirizine, desloratadine, mizolastine, fexofenadine, olopatadine hydrochloride, norastemizole, levocetirizine, levocabastine, azelastine, ebastine and loratadine; antileukotrienes (e.g., anti-cysteinyl leukotrienes (CysLTs)) such as oxatomide, montelukast, zafirlukast and zileuton; phosphodiesterase inhibitors (e.g., PDE4 subtype) such as ibudilast, cilomilast, BAY 19-8004, theophylline (e.g., sustained-release) and other xanthine derivatives (e.g., doxofylline); thromboxane antagonists such as seratrodast, ozagrel hydrochloride and ramatroban; prostaglandin antagonists such as COX-1 and COX-2 inhibitors (e.g., celecoxib and rofecoxib), aspirin; and potassium channel openers. Additional non-limiting examples of classes of other agents and drugs include anti-inflammatory agents that are immunomodulatory therapies, such as pro-inflammatory cytokine antagonists, such as TNFα antagonists (e.g. etanercept, aka Enbrel™); immune cell antagonists, such as the B cell depleting agent rituximab, and the T cell costimulation blocker abatacept, which have been used to treat rheumatoid arthritis, and anti-inflammatory antibodies that bind to cytokines, such as anti-IgE (e.g., rhuMAb-E25 omalizumab), and anti-TNFα, IFNγ, IL-1, IL-2, IL-5, IL-6, IL-9, IL-13, IL-16, and growth factors such as granulocyte/macrophage colony-stimulating factor.

As disclosed herein, the method or use of the present invention using the bi-specific fusion polypeptide can provide a detectable or measurable therapeutic benefit or improvement to a subject.

The therapeutic benefit or improvement may be any measurable or detectable, objective or subjective, transient, temporary, or longer-term benefit to the subject or improvement in the response, disorder or disease, or one or more adverse symptoms, disorders, illnesses, pathologies, diseases, or complications caused by or associated with the undesirable or aberrant response, disorder or disease. Therapeutic benefits and improvements may include, but are not limited to, decreasing, reducing, inhibiting, suppressing, limiting or controlling the occurrence, frequency, severity, progression, or duration of an adverse symptom of undesirable or aberrant response, disorder or disease. Therapeutic benefits and improvements may also include, but are not limited to, decreasing, reducing, inhibiting, suppressing, limiting or controlling amounts or activity of inflammation and inflammatory responses, such as T cells, B-cells, autoantibodies, immune cell infiltration or mobilization, pro-inflammatory cytokines, lymphokines or chemokines.

According to the present invention, an effective or sufficient amount of the bi-specific fusion polypeptide is administered to a subject. An "effective amount" or "sufficient amount" refers to an amount that provides, in single or multiple doses, alone or in combination, with one or more other components (therapeutic agent such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

The term "effective amount" or "sufficient amount" for treatment (e.g., to ameliorate or to provide a therapeutic benefit or improvement) typically refers to an amount effective to provide a response, disorder or disease, of one, multiple or all adverse symptoms, consequences or complications of the response, disorder or disease, one or more adverse symptoms, disorders, illnesses, pathologies, diseases, or complications, for example, those caused by or associated with an undesirable or an undesirable or aberrant immune response, disorder or disease, an inflammatory response, disorder or disease, inflammation, an autoimmune response, disorder or disease, to a measurable extent, although decreasing, reducing, inhibiting, suppressing, limiting or controlling progression or worsening of the response, disorder or disease of a cell, tissue or organ, or an adverse symptom thereof, is a satisfactory outcome.

An effective amount or a sufficient amount may but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the response, disorder, or disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol.

As is typical for treatments, some subjects may exhibit a greater response, or less or no response to a given treatment. An effective amount or a sufficient amount therefore need not be effective in each and every subject treated, prophylactically or therapeutically, nor a majority of treated subjects in a given group or population. An effective amount or a sufficient amount means effectiveness or sufficiency in a particular subject, not a group or the general population. Accordingly, appropriate amounts will depend upon the condition treated, the therapeutic effect desired, as well as the individual subject (e.g., the bioavailability within the subject, gender or age).

The term "ameliorate" refers to a detectable or measurable improvement in a subject's condition or an underlying cellular response. A detectable or measurable improvement includes a subjective or objective decrease, reduction, inhibition, suppression, limit or control in the occurrence, frequency, severity, progression, or duration of the response, disorder or disease, such as an undesirable or undesirable or aberrant immune response, disorder or disease, an inflammatory response, disorder or disease, inflammation, an autoimmune response, disorder or disease, or one or more adverse symptoms, disorders, illnesses, pathologies, diseases, or complications caused by or associated with the response, disorder or disease, such as an undesirable or aberrant immune response, disorder or disease, an inflammatory response, disorder or disease, inflammation, an autoimmune response, disorder or disease, or a reversal of the response, disorder or disease, such as an undesirable or aberrant immune response, disorder or disease, an inflammatory response, disorder or disease, inflammation, an autoimmune response, disorder or disease. Such improvements can also occur at the cellular level.

Thus, a successful treatment outcome can lead to a "therapeutic effect," or "benefit" of decreasing, reducing, inhibiting, suppressing, limiting, controlling or preventing the occurrence, frequency, severity, progression, or duration of an undesirable or aberrant immune response, disorder or disease, an inflammatory response, disorder or disease, inflammation, an autoimmune response, disorder or disease, or one or more adverse symptoms or underlying causes or consequences of the undesirable or aberrant immune response, disorder or disease, an inflammatory response, disorder or disease, inflammation, an autoimmune response, disorder or disease, in a subject. Treatment methods affecting one or more underlying causes of the response, disorder or disease or adverse symptom are therefore considered to be beneficial. A decrease or reduction in worsening, such as stabilizing an undesirable or aberrant immune response, disorder or disease, an inflammatory response, disorder or disease, inflammation, an autoimmune response, disorder or disease, is also a successful treatment outcome.

A therapeutic benefit or improvement therefore need not be complete ablation of an undesirable or aberrant immune response, disorder or disease, an inflammatory response, disorder or disease, inflammation, an autoimmune response, disorder or disease, or any one, most or all adverse symptoms, complications, consequences or underlying causes associated with the an undesirable or aberrant immune response, disorder or disease, an inflammatory response, disorder or disease, inflammation, an autoimmune response, disorder or disease. Thus, a satisfactory endpoint may be achieved when there is an incremental improvement in a subject's response, disorder or disease, or a partial decrease, reduction, inhibition, suppression, limit, control or prevention in the occurrence, frequency, severity, progression, or duration, or inhibition or reversal, of the response, disorder or disease (e.g., stabilizing one or more symptoms or complications), such as an undesirable or aberrant immune response, disorder or disease, an inflammatory response, disorder or disease, inflammation, an autoimmune response, disorder or disease, or one or more adverse symptoms, disorders, illnesses, pathologies, diseases, or complications caused by or associated with an undesirable or aberrant immune response, disorder or disease, an inflammatory response, disorder or disease, inflammation, an autoimmune response, disorder or disease, over a short or long duration of time (hours, days, weeks or months).

Effectiveness of a method or use, such as a treatment that provides a potential therapeutic benefit or improvement of a response, disorder or disease, such as an undesirable or aberrant immune response, disorder or disease, an inflammatory response, disorder or disease, inflammation, an autoimmune response, disorder or disease, may be ascertained by various methods. Such methods include, for example, scores measuring swelling, pain, rash, headache, fever, nausea, diarrhea, bloat, lethargy, skeletal joint stiffness, lack of mobility, rash, or tissue or cell damage. Measuring T or B cell activation and/or differentiation, cell infiltration of a region, cell accumulation or migration to a region, production of antibodies, cytokines, lymphokines, chemokines, interferons and interleukins, cell growth and maturation factors using various immunological assays, such as ELISA. Determining the degree of cell, tissue or organ damage may be ascertained by CT scanning, MRI, ultrasound, molecular contrast imaging, or molecular ultrasound contrast imaging. For skeletal joints, inflammation may be assessed by patient self-assessment, tender joint-counts and swollen joint-counts, and the erythrocyte sedimentation rate (ESR) or C-reactive protein (CRP). For gastrointestinal tract, inflammation may be assessed by, endoscopy (colonoscopy, gastroscopy, ERCP), for example. For inflammation of the central nervous system (CNS), cells and cytokines in spinal tap reflect inflammation, for example.

The term "subject" refers to an animal, typically a mammalian animal, such as human, a non-human primate (e.g., ape, gibbon, chimpanzee, orangutan or macaque), a companion animal (e.g., dog and cat), a farm animal (e.g., horse, cow, goat, sheep or pigs) or an experimental animal (e.g., mouse, rat, rabbit or guinea pig). Examples of subjects may include animal disease models, for example, animal models of an undesirable or aberrant immune response, disorder or disease, an inflammatory response, disorder or disease, inflammation, an autoimmune response, disorder or disease (e.g., CIA, BXSB, EAE and SCID mice), for in vivo analysis.

Examples of subjects appropriate for the treatment may include those having an undesirable or aberrant immune response, disorder or disease, an inflammatory response, disorder or disease, inflammation, an autoimmune response, disorder or disease, those undergoing treatment for an undesirable or aberrant immune response, disorder or disease, an inflammatory response, disorder or disease, inflammation, an autoimmune response, disorder or disease, as well as those who have undergone treatment or therapy for an undesirable or aberrant immune response, disorder or disease, an inflammatory response, disorder or disease, inflammation, an autoimmune response, disorder or disease, including subjects where the undesirable or aberrant immune response, disorder or disease, inflammatory response, disorder or disease, inflammation, an autoimmune response, disorder or disease, is in remission.

Examples of the subjects may include those having or at risk of having any of: polymyositis, vasculitis syndrome, giant cell arteritis, Takayasu arteritis, relapsing, polychondritis, acquired hemophilia A, Still's disease, adult-onset Still's disease, amyloid A amyloidosis, polymyalgia rheumatica, Spondyloarthritides, Pulmonary arterial hypertension, graft-versus-host disease, autoimmune myocarditis, contact hypersensitivity (contact dermatitis), gastro-oesophageal reflux disease, erythroderma, Behçet's disease, amyotrophic lateral sclerosis, transplantation, Neuromyelitis Optica, rheumatoid arthritis, juvenile rheumatoid arthritis, malignant rheumatoid arthritis, Drug-Resistant Rheumatoid Arthritis, Neuromyelitis optica, Kawasaki disease, polyarticular or systemic juvenile idiopathic arthritis, psoriasis, chronic obstructive pulmonary disease (COPD), Castleman's disease, asthma, allergic asthma, allergic encephalomyelitis, arthritis, arthritis chronica progrediente, reactive arthritis, psoriatic arthritis, enterophathic arthritis, arthritis deformans, rheumatic diseases, spondyloarthropathies, ankylosing spondylitis, Reiter syndrome, hypersensitivity (including both airway hypersensitivity and dermal hypersensitivity), allergies, systemic lupus erythematosus (SLE), cutaneous lupus erythematosus, erythema nodosum leprosum, Sjögren's Syndrome, inflammatory muscle disorders, polychondritis, Wegener's granulomatosis, dermatomyositis, Steven-Johnson syndrome, chronic active hepatitis, myasthenia gravis, idiopathic sprue, autoimmune inflammatory bowel disease, ulcerative colitis, Crohn's disease, Irritable Bowel Syndrome, endocrine ophthalmopathy, scleroderma, Grave's disease, sarcoidosis, multiple sclerosis, primary biliary cirrhosis, vaginitis, proctitis, insulin-dependent diabetes mellitus, insulin-resistant diabetes mellitus, juvenile diabetes (diabetes mellitus type I), autoimmune haematological disorders, hemolytic anemia, aplastic anemia, pure red cell anemia, idiopathic thrombocytopenia (ITP), autoimmune uveitis, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, inflammatory disease of skin, cornea inflammation, myositis, loosening of bone implants, metabolic disorder, atherosclerosis, dislipidemia, bone loss, osteoarthritis, osteoporosis, periodontal disease of obstructive or inflammatory airways diseases, bronchitis, pneumoconiosis, pulmonary emphysema, acute and hyperacute inflammatory reactions, acute infections, septic shock, endotoxic shock, adult respiratory distress syndrome, meningitis, pneumonia, cachexia wasting syndrome, stroke, herpetic stromal keratitis, dry eye disease, iritis, conjunctivitis, keratoconjunctivitis, Guillain-Barre syndrome, Stiff-man syndrome, Hashimoto's thyroiditis, autoimmune thyroiditis, encephalomyelitis, acute rheumatic fever, sympathetic ophthalmia, Goodpasture's syndrome, systemic necrotizing vasculitis, antiphospholipid syndrome, Addison's disease, pemphigus vulgaris, pemphigus foliaceus, dermatitis herpetiformis, atopic dermatitis, eczematous dermatitis, aphthous ulcer, lichen planus, autoimmune alopecia, Vitiligo, autoimmune hemolytic anemia, autoimmune thrombocytopenic purpura, pernicious anemia, sensorineural hearing loss, idiopathic bilateral progressive sensorineural hearing loss, autoimmune polyglandular syndrome type I or type II, immune infertility or immune-mediated infertility.

Examples of the subjects may further include those that are at increased risk of an undesirable or aberrant immune response, disorder or disease, an inflammatory response, disorder or disease, inflammation, an autoimmune response, disorder or disease. A candidate subject, for example, has an undesirable or aberrant immune response, disorder or disease, an inflammatory response, disorder or disease, inflammation, an autoimmune response, disorder or disease, or is being treated with a therapy or drug for an undesirable or aberrant immune response, disorder or disease, an inflammatory response, disorder or disease, inflammation, an autoimmune response, disorder or disease. Candidate subjects also include subjects that would benefit from or are in need of treatment for an undesirable or aberrant immune response, disorder or disease, an inflammatory response, disorder or disease, inflammation, an autoimmune response, disorder or disease.

"At risk" subject may typically have increased risk factors for an undesirable or aberrant immune response, disorder or disease, an inflammatory response, disorder or disease, inflammation, an autoimmune response, disorder or disease. Particular examples of the subjects at risk may include those that have had an undesirable or aberrant immune response, disorder or disease, an inflammatory response, disorder or disease, inflammation, an autoimmune response, disorder or disease. Examples of subjects at risk may also include those prescribed a treatment or therapy for an undesirable or aberrant immune response, disorder or disease, an inflammatory response, disorder or disease, inflammation, an autoimmune response, disorder or disease. Examples of at risk subjects may also include those with risk factors such as a family history (e.g., genetic predisposition), gender, lifestyle (diet, smoking), occupation (medical and clinical personnel, agricultural and livestock workers) or environmental factors (allergen exposure).

According to the present invention, the composition comprising the fusion polypeptide may be packaged in a dosage unit form for ease of administration and uniformity of dosage. "Dosage unit form" as used herein refers to physically discrete units suited as unitary dosages treatment; each unit contains a quantity of the composition in association with the carrier, excipient, diluent, or vehicle calculated to produce the desired treatment or therapeutic (e.g., beneficial) effect. The unit dosage forms may vary according to factors including, but not limited to, the particular composition employed, the disorder or disease treated, the effect to be achieved, and the subject to be treated. Exemplary unit doses range from about 25-250, 250-500, 500-1,000, 1,000-2,500, 2,500-5,000, 5,000-25,000, or 5,000-50,000 pg; from about 50-500, 500-5,000, 5,000-25,000 or 25,000-50,000 ng; from about 50-500, 500-5,000, 5,000-25,000 or 25,000-50,000 µg; from about 25-250, 250-500, 500-1,000, 1,000-2,500, 2,500-5,000, 5,000-25,000, or 5,000-50,000 mg; and from about 1-5, 5-10, 10-25, 25-50, 50-100, 100-250, 250-500, 500-1,000, 1,000-2,500, or 2,500-5,000 grams.

As set forth herein, fusion polypeptides and compositions thereof may be contacted or provided in vitro, ex vivo or administered or delivered in vivo to a subject or patient in various doses and amounts, and frequencies. For example, a fusion polypeptide or a composition thereof may be administered or delivered to provide the intended effect, as a single or as multiple dosages, for example, in an effective or sufficient amount. Exemplary doses range from about 25-250, 250-500, 500-1,000, 1,000-2,500, 2,500-5,000, 5,000-25,000, or 5,000-50,000 pg/kg; from about 50-500, 500-5,000, 5,000-25,000 or 25,000-50,000 ng/kg; from about 50-500, 500-5,000, 5,000-25,000 or 25,000-50,000 pg/kg; and from about 25-250, 250-500, 500-1,000, 1,000-2,500, 2,500-5,000, 5,000-25,000, or 5,000-50,000 mg/kg, on consecutive days, alternating days or intermittently.

Single or multiple (e.g., 2, 3, 4, 5, 6, 7, 8, 9, 10, or more times) administrations or doses of the composition may be administered on the same or consecutive days, alternating days or intermittently. For example, the composition comprising the fusion polypeptide may be administered one, two, three, four or more times daily, on alternating days, bi-weekly, weekly, monthly, bi-monthly, or annually. the composition comprising the fusion polypeptide may be administered for any appropriate duration, for example, for period of 1 hour, or less, e.g., 30 minutes or less, 15 minutes or less, 5 minutes or less, or 1 minute, or less.

The composition comprising the fusion polypeptide may be administered to a subject prior to, substantially contemporaneously with, or within about 1-60 minutes, hours (e.g., within 1, 2, 3, 4, 5, 6, 8, 12, 24 hours), or days (1, 2, 3, 4, 5, 6, 7, 7-14, 14-21, 21-28, 28-45, 45-60 or 60-90 days) of a symptom or onset of an undesirable or aberrant immune response, disorder or disease, an inflammatory response, disorder or disease, inflammation, an autoimmune response, disorder or disease.

The composition comprising the fusion polypeptide may be administered via systemic, regional or local administration, by any route. For example, the composition comprising the fusion polypeptide may be administered systemically, regionally or locally, via injection, infusion, orally (e.g., ingestion or inhalation), topically, intravenously, intra-arterially, intramuscularly, intraperitoneally, intradermally, subcutaneously, intracavity, intracranially, transdermally (topical), parenterally, e.g. transmucosally or intrarectally (enema) catheter, or optically. Fusion polypeptides, compositions, methods and uses of the invention including pharmaceutical formulations administered via a (micro)encapsulated delivery system or packaged into an implant for administration.

The present invention also provides a kit including the fusion polypeptide (FynomAb) of the invention and packaged into suitable packaging material. A kit may optionally include a label or packaging insert including a description of the components or instructions for use in vitro, in vivo, or ex vivo, of the components therein. Exemplary instructions include instructions for a method, treatment protocol or therapeutic regimen.

A kit may contain a collection of components, e.g., two or more compositions each comprising different bi-specific fusion polypeptide, or a composition comprising a bi-specific fusion polypeptide and a composition comprising another therapeutically useful composition (e.g., an antiproliferative or immune-enhancing drug). The term "packaging material" refers to a physical structure housing the components of the kit. The packaging material may maintain the components sterilely, and may be made of material commonly used for such purposes (e.g., paper, corrugated fiber, glass, plastic, foil, ampules, vials, or tubes).

The kit may include a label or insert. The label or insert may be a "printed matter," e.g., paper or cardboard, or separate or affixed to a component, a kit or packing material (e.g., a box), or attached to an ampule, tube or vial containing a kit component. The label or insert may be a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards.

The label or insert may include identifying information of one or more components therein, dose amounts, clinical pharmacology of the active ingredient(s) including mechanism of action, pharmacokinetics (PK) and pharmacodynamics (PD). Labels or inserts can include information identifying manufacturer information, lot numbers, manufacturer location and date.

The label or insert may include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore may additionally include a label or instruction for practicing any of the methods and uses of the invention described herein.

The label or insert may include information on any benefit that a component may provide, such as a prophylactic or therapeutic benefit. The label or insert may include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

The kit may additionally include other components. Each component of the kit may be enclosed within an individual container and all of the various containers may be within a single package. Invention kits may be designed for cold storage. Invention kits can further be designed to contain host cells expressing fusion polypeptides of the invention, or that contain nucleic acids encoding fusion polypeptides. The cells in the kit may be maintained under appropriate storage conditions until the cells are ready to be used. For example, a kit including one or more cells can contain appropriate cell storage medium so that the cells may be thawed and grown.

Unless otherwise defined, all technical and scientific terms used herein have the same meaning as commonly understood by one of ordinary skill in the art to which this invention belongs. Although methods and materials similar or equivalent to those described herein may be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a fusion polypeptide (FynomAb)" or "a target (e.g., IL-17a or IL-6R)," may include single or a plurality of such fusion polypeptides, targets, and so forth.

As used herein, numerical values are often presented in a range format throughout this document. The use of a range format is merely for convenience and brevity and should not be construed as an inflexible limitation on the scope of the invention unless the context clearly indicates otherwise.

Accordingly, a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, and so forth.

In addition, reference to a range of 1-5,000 fold includes 1, 2, 3, 4, 5, 6, 7, 8, 9, 10, 11, 12, 13, 14, 15, 16, 17, 18, 19, 20 fold, etc., as well as 1.1, 1.2, 1.3, 1.4, 1.5, fold, etc., 2.1, 2.2, 2.3, 2.4, 2.5, fold, etc., and any numerical range within such a ranges, such as 1-2, 5-10, 10-50, 50-100, 100-500, 100-1000, 500-1000, 1000-2000, 1000-5000, etc. In a further example, reference to a range of KD $10^{-5}$ M to about KD $10^{-13}$ M includes any numerical value or range within or encompassing such values.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, 150-200, etc., includes ranges such as 5-20, 5-30, 5-40, 5-50, 5-75, 5-100, 5-150, 5-200, and 10-30, 10-40, 10-50, 10-75, 10-100, 10-150, 10-171, and 20-40, 20-50, 20-75, 20-100, 20-150, 20-200, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

Fyn SH3-derived polypeptides of the invention bind to IL-17A as determined by monoclonal lysate ELISA.

Method

Process for producing fynomers that bind IL-17a is described in PCT/EP2013/069481. In brief, Fyn-SH3 derived binding proteins specific to IL-17A were isolated using recombinant IL-17A (R&D Systems) as antigen and standard phage display as selection technology (Grabulovski D. et al., (2007) J Biol Chem 282, p. 3196-3204, Viti, F. et al. (2000) Methods Enzymol. 326, 480-505). Fyn SH3-derived polypeptide of the invention 1L3-B09 carrying the n-src-loop sequence "STHEYE" was enriched during the selection process. 1L3-B09 bound IL-17A and was found to inhibit glycosylated IL-17A as good as non-glycosylated IL-17A. In order to obtain Fyn SH3-derived IL-17A binders with higher affinities, 1L3-B09 was used as template for affinity maturation. The n-src-loop sequence "STHEYE" was kept constant and was combined with a randomized RT-loop repertoire (6 amino acid residues designated as (X1) (X2) (X3) (X4) (X5) (X6)). The process of affinity maturation library generation was essentially the same as described for cloning of the naïve library with a randomized RT-loop ("library 0" in Schlatter et al. (2012) mAbs, 4(4) p. 497-50).

After naïve and affinity maturation selections, enriched Fyn SH3-derived polypeptides were screened for binding to IL-17A by lysate ELISA. DNA encoding the Fyn SH3-derived binding proteins were cloned into the bacterial expression vector pQE12 (Qiagen) so that the resulting constructs carried a C-terminal myc-hexahistidine tag as described in Grabulovski et al. (Grabulovski et al. (2007) JBC, 282, p. 3196-3204). The polypeptides were expressed in the cytosol of *E. coli* bacteria in a 96-well format and 200 µl of cleared lysate per well was prepared as described in Bertschinger et al. (Bertschinger et al. (2007) Protein Eng Des Sel 20(2): p. 57-68). Briefly, transformed bacterial colonies were picked from the agar plate and grown in a round bottom 96-well plate (Nunc, cat. no. 163320) in 200 µl 2×YT medium containing 100 µg/ml ampicillin and 0.1% (w/v) glucose. Protein expression was induced after growth for 3 h at 37° C. and 200 r.p.m. by adding 1 mM IPTG (Applichem, Germany). Proteins were expressed overnight in a rotary shaker (200 r.p.m., 30° C.). Subsequently, the 96-well plate was centrifuged at 1800 g for 10 min and the supernatant was discarded. The bacterial pellets were resuspended in 200 µl lysis buffer (50 mM NaH2PO4, 300 mM NaCl, 10 mM imidazole, pH 8.0) containing 1 mg/ml lysozyme and left for 30 min on ice. Afterwards, the bacterial cells were lysed by sonication in a water bath (six bursts for 10 s) and then centrifuged at 1800 g for 10 min. Monoclonal bacterial lysates were used for ELISA: biotinylated IL-17A (produced in-house in HEK EBNA cells, biotinylation was performed with NHS-PEO4-biotin (Pierce) according to the manufacturer's instructions) was immobilized on streptavidin-coated wells (StreptaWells, High Bind, Roche), and after blocking with PBS, 2% milk (Rapilait, Migros, Switzerland), 50 µl of PBS, 4% milk containing 6 µg/ml anti-myc antibody 9E10 (final concentration 3 µg/ml) and 50 µl of bacterial lysate were applied. After incubating for 1 h and washing, bound Fyn SH3-derived polypeptides were detected with anti-mouse-HRP antibody conjugate (Sigma). The detection of peroxidase activity was done by adding BM blue POD substrate (Roche) and the reaction was stopped by adding 1 M H2SO4. The DNA sequence of the specific binders was verified by DNA sequencing.

Results

The sequences of seven representative IL-17A binding fynomer sequences (SEQ ID NOs:1-7) are as follows:

```
SEQ ID NO: 1(1L3-B9):
GVTLFVALYDYANHGNRDLSFHKGEKFQILSTHEYEDWWEARSLTTGETG

YIPSNYVAPVDSIQ;

SEQ ID NO: 2(11L0-C06):
GVTLFVALYDYKQKGHLDLSFHKGEKFQILSTHEYEDWWEARSLTTGETG

YIPSNYVAPVDSIQ;
```

```
SEQ ID NO: 3 (11L5-B06):
GVTLFVALYDYSARGQLDLSFHKGEKFQILSTHEYEDWWEARSLTTGETG

YIPSNYVAPVDSIQ;

SEQ ID NO: 4 (11L6-F03):
GVTLFVALYDYDKLSALDLSFHKGEKFQILSTHEYEDWWEARSLTTGETG

YIPSNYVAPVDSIQ;

SEQ ID NO: 5 (11L9-C09):
GVTLFVALYDYESVSWSDLSFHKGEKFQILSTHEYEDWWEARSLTTGETG

YIPSNYVAPVDSIQ;

SEQ ID NO: 6 (11L10-A05):
GVTLFVALYDYSSRGVLDLSFHKGEKFQILSTHEYEDWWEARSLTTGETG

YIPSNYVAPVDSIQ;
and

SEQ ID NO: 7 (11L11-A09):
GVTLFVALYDYSRKSNLDLSFHKGEKFQILSTHEYEDWWEARSLTTGETG

YIPSNYVAPVDSIQ.
```

Eight (8) different fynomer-antibody (FynomAbs) fusions were created by fusing four (4) separate anti-IL-17A binding fynomers to either the C-terminus of the heavy chain (COVA801, COVA803, COVA805, COVA807) or to the C-terminus of the light chain (COVA802, COVA804, COVA806, COVA808) of an IL-6R binding antibody, tocilizumab (see Table 1).

TABLE 1

FynomAb description.

| FynomAb | Fynomer | Format | MW (kDa) | pI |
|---|---|---|---|---|
| Actemra | — | parental | 145.0 | 8.62 |
| COVA801 | 11L0-C06 | HC, C-term | 161.6 | 8.23 |
| COVA802 | 11L0-C06 | LC, C-term | 161.6 | 8.23 |
| COVA803 | 11L5-B06 | HC, C-term | 161.5 | 8.09 |
| COVA804 | 11L5-C06 | LC, C-term | 161.5 | 8.09 |
| COVA805 | 11L9-C09 | HC, C-term | 161.6 | 7.65 |
| COVA806 | 11L9-C09 | LC, C-term | 161.6 | 7.65 |
| COVA807 | 11L10-A05 | HC, C-term | 161.4 | 8.09 |
| COVA808 | 11L10-A05 | LC, C-term | 161.4 | 8.09 |

HC: heavy chain;
LC: light chain;
pI: Isoelectric point;
MW: molecular weight;
kDa: kilodalton The studies assess the biochemical and functional characteristics as well as the pharmacokinetic properties of these different FynomAbs. Several different lots of the COVA801-808 FynomAbs were assessed. FynomAbs were either produced from transient or stable transfections of CHO cells. FynomAbs for the mouse and cynomolgus (cyno) monkey PK studies were produced from stable CHO cell lines.

Example 2

Protein Expression and Purification

Four separate lots of FynomAbs were prepared and evaluated in the studies documented below. Two lots of material were derived from transiently transfected CHO cells. The lots of material generated in house were derived from stable CHO pools using the Lonza expression vectors as described below.

The heavy and light chain sequences of Actemra (tocilizumab) were obtained from the CAS database and also confirmed as Sequence #15 in US 2011/0076275 A1. A modification was made to the sequence to mutate amino acids 356-358 DEL to EEM. This is a mutation from the G1m1 allotype to the nG1m1 and could potentially reduce immunogenicity.

```
Actemra (tocilizumab) heavy chain sequence
(SEQ ID NO: 8)  (CDRs in bold)
  1 QVQLQESGPG LVRPSQTLSL TCTVSGYSIT SDHAWSWVRQ PPGRGLEWIG

51 YISYSGITTY NPSLKSRVTM LRDTSKNQFS LRLSSVTAAD TAVYYCARSL

101 ARTTAMDYWG QGSLVTVSSA STKGPSVFPL APSSKSTSGG TAALGCLVKD

151 YFPEPVTVSW NSGALTSGVH TFPAVLQSSG LYSLSSVVTV PSSSLGTQTY

201 ICNVNHKPSN TKVDKKVEPK SCDKTHTCPP CPAPELLGGP SVFLFPPKPK

251 DTLMISRTPE VTCVVVDVSH EDPEVKFNWY VDGVEVHNAK TKPREEQYNS

301 TYRVVSVLTV LHQDWLNGKE YKCKVSNKAL PAPIEKTISK AKGQPREPQV

351 YTLPPSREEM TKNQVSLTCL VKGFYPSDIA VEWESNGQPE NNYKTTPPVL

401 DSDGSFFLYS KLTVDKSRWQ QGNVFSCSVM HEALHNHYTQ KSLSLSPG*

Actemra (tocilizumab) light chain sequence
(SEQ ID NO: 9)  (CDRs in bold)
  1 DIQMTQSPSS LSASVGDRVT ITCRASQDIS SYLNWYQQKP GKAPKLLIYY

51 TSRLHSGVPS RFSGSGSGTD FTFTISSLQP EDIATYYCQQGNTLPYTFGQ

101 GTKVEIKRTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201 LSSPVTKSFN RGEC*
```

These sequences for the tocilizumab heavy and light chains were codon optimized for CHO expression and the genes synthesized. Signal sequences were added to the 5' ends of each gene (Hc ss=MEWSWVFLFFLSVTTGVHS; Lc ss=MSVPTQVLGLLLLWLTDARC). The FynomAb fusion proteins were constructed by putting each of the four fynomer sequences on the C-terminus of either the heavy or light chain of tocilizumab, with a 15 amino acid linker in between (GGGGSx3). This created the genes required to generate eight FynomAbs. The synthesized genes were cloned into the Lonza pEE 12.4 (heavy chain) and 6.4 (light chain) vectors. These vectors were then combined to make a single expression vector to express the heavy and light chains combinations for tocilizumab and all eight FynomAb molecules.

TABLE 2

FynomAb description with fynomer sequences

| Molecule | Description | Fynomer Sequence |
|---|---|---|
| COVA801 | tocilizumab with C-terminal 11L0_C06 fynomer on heavy chain | GVTLFVALYDYKQKGHLDLSFHKGE KFQILSTHEYEDWWEARSLTTGETG YIPSNYVAPVDSIQ(SEQ ID NO: 2) |
| COVA802 | tocilizumab with C-terminal 11L0_C06 fynomer on light chain | GVTLFVALYDYKQKGHLDLSFHKGE KFQILSTHEYEDWWEARSLTTGETG YIPSNYVAPVDSIQ(SEQ ID NO: 2) |
| COVA803 | tocilizumab with C-terminal 11L5_B06 fynomer on heavy chain | GVTLFVALYDYSARGQLDLSFHKGE KFQILSTHEYEDWWEARSLTTGETG YIPSNYVAPVDSIQ(SEQ ID NO: 3) |
| COVA804 | tocilizumab with C-terminal 11L5_B06 fynomer on light chain | GVTLFVALYDYSARGQLDLSFHKGE KFQILSTHEYEDWWEARSLTTGETG YIPSNYVAPVDSIQ(SEQ ID NO: 3) |
| COVA805 | tocilizumab with C-terminal 11L9_C09 fynomer on heavy chain | GVTLFVALYDYESVSWSDLSFHKGE KFQILSTHEYEDWWEARSLTTGETG YIPSNYVAPVDSIQ(SEQ ID NO: 5) |
| COVA806 | tocilizumab with C-terminal 11L9_C09 fynomer on light chain | GVTLFVALYDYESVSWSDLSFHKGE KFQILSTHEYEDWWEARSLTTGETG YIPSNYVAPVDSIQ(SEQ ID NO: 5) |
| COVA807 | tocilizumab with C-terminal 11L10_A05 fynomer on heavy chain | GVTLFVALYDYSSRGVLDLSFHKGE KFQILSTHEYEDWWEARSLTTGETG YIPSNYVAPVDSIQ(SEQ ID NO: 6) |
| COVA808 | tocilizumab with C-terminal 11L10_A05 fynomer on light chain | GVTLFVALYDYSSRGVLDLSFHKGE KFQILSTHEYEDWWEARSLTTGETG YIPSNYVAPVDSIQ(SEQ ID NO: 6) |

CHO-K1-SV cells were nucleofected (Amaxa) with linearized DNA of each of the eight FynomAb vectors and tocilizumab. These cells were put into MSX selection and cultured in pairs of static flasks until the cultures recovered. Once the cells recovered they were transferred to shake flasks and either immediately frozen or expanded to production flasks for large scale protein expression.

The first rounds of production flasks were purified for generating material for the in-house mouse PK study and for use in the in vitro assays. The frozen cultures of these same pools were later thawed and expanded when more protein was needed for the cynomolgus PK studies.

Expression levels were quantified by AlphaLISA and Western blot. Expression levels of the stable pools ranged from approximately 100-500 mg/L. Production flasks were cultured for ten days before harvest, filtration, and freezing with protease inhibitors. Some low expression pools were "cold captured" and sorted—the antibody on the cell surfaces was stained and then the cells sorted by flow cytometry to capture the highest producing cells for culture and production. Supernatants from the stable pools (0.5-8.0 L) were filtered through a 0.2 µM vacuum filter upon harvest and protease inhibitor tablets (Sigma, cat# P2714, 1 tablet/100 mL supernatant) were added prior to freezing or storage at 4° C.

Supernatants for all FynomAb production cell lines were initially purified under aseptic conditions using HiTrap MabSelect SuRe columns (1 or 5 mL columns; sometimes multiples in tandem) loading at a flow rate of 5-20 mL/minute. Columns were washed with PBS until a baseline A280 reading was reached, followed by elution with glycine, pH 3.0.

The different lots of the CHO stable material made for each FynomAb along with protein yields are listed in Table 3.

TABLE 3 yields of FynomAbs and tocilizumab produced

| Construct | Host/ Expression | Yield (mg) | Conc. mg/mL (µM) | Volume (mL) | Yield (mg/L sup) |
|---|---|---|---|---|---|
| tocilizumab | CHO-S/ transient | 1.31 | 5.0 (35.5) | 0.26 | 2.6 |
| tocilizumab | CHO-K1SV/ stable | 2.9 | 4.40 (30.3) | 0.66 | 1.2 |
| tocilizumab | CHO-K1SV/ stable (sorted) | 291 | 2.75 (19.0) | 105.8 | 36.4 |
| COVA801 | CHO-K1SV/ stable | 36.0 | 4.0 (24.7) | 9.0 | >72 |
| COVA801 | CHO-K1SV/ stable | 410 | 1.35 (8.3) | 303.7 | 205 |
| COVA802 | CHO-K1SV/ stable | 1.43 | 3.96 (24.4) | 0.36 | 3.0 |
| COVA802 | CHO-K1SV/ stable | 7.1 | 1.68 (10.3) | 4.3 | 1.6 |
| COVA802 | CHO-K1SV/ stable | 252 | 0.91 (5.6) | 276.9 | 45.8 |
| COVA803 | CHO-K1SV/ stable | 26.1 | 3.86 (23.8) | 6.8 | >50 |
| COVA803 | CHO-K1SV/ stable | 330 | 1.27 (7.8) | 259.8 | 110.0 |
| COVA804 | CHO-K1SV/ stable | 32.2 | 4.81 (29.7) | 6.7 | >72 |
| COVA804 | CHO-K1SV/ stable | 337 | 0.96 (5.9) | 351.0 | 112.3 |
| COVA805 | CHO-K1SV/ stable | 19.5 | 2.78 (17.2) | 7.0 | >41 |
| COVA806 | CHO-K1SV/ stable | 47.9 | 5.1 (31.5) | 9.4 | >90 |
| COVA806 | CHO-K1SV/ stable | 428 | 2.74 (16.9) | 156.2 | 142.7 |
| COVA807 | CHO-K1SV/ stable | 59.7 | 6.63 (40.9) | 9.0 | >120 |
| COVA807 | CHO-K1SV/ stable | 59.7 | 6.63 (40.9) | 9.0 | >120 |
| COVA808 | CHO-K1SV/ stable | 22.8 | 3.35 (20.7) | 6.8 | >48 |
| COVA808 | CHO-K1SV/ Stable (sorted) | 245 | 1.41 (8.7) | 173.8 | 54.4 |

Example 3

SDS-PAGE Analysis

Figure 2A:
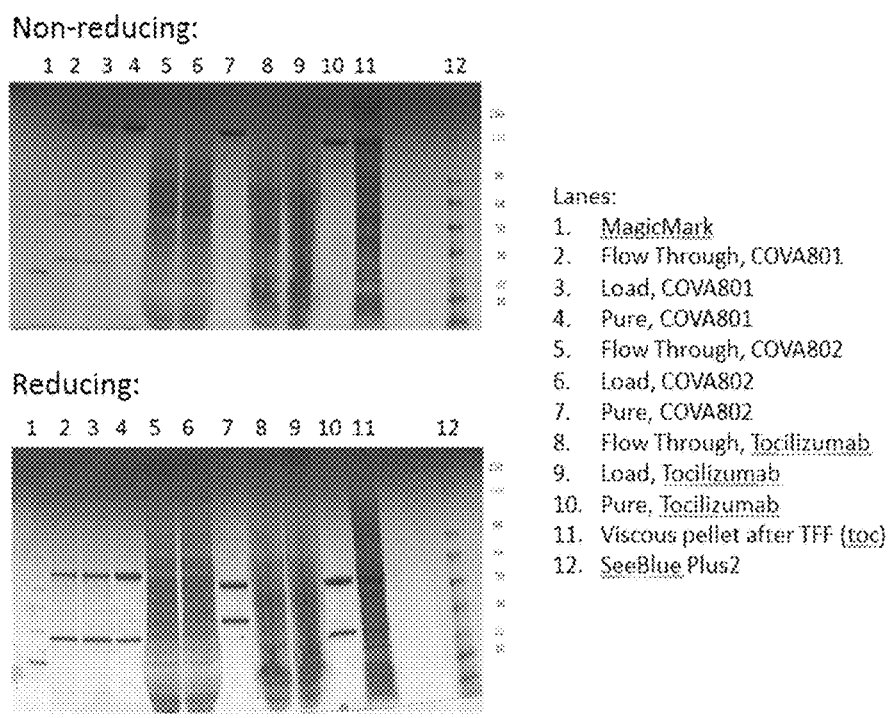
Figure 2B:
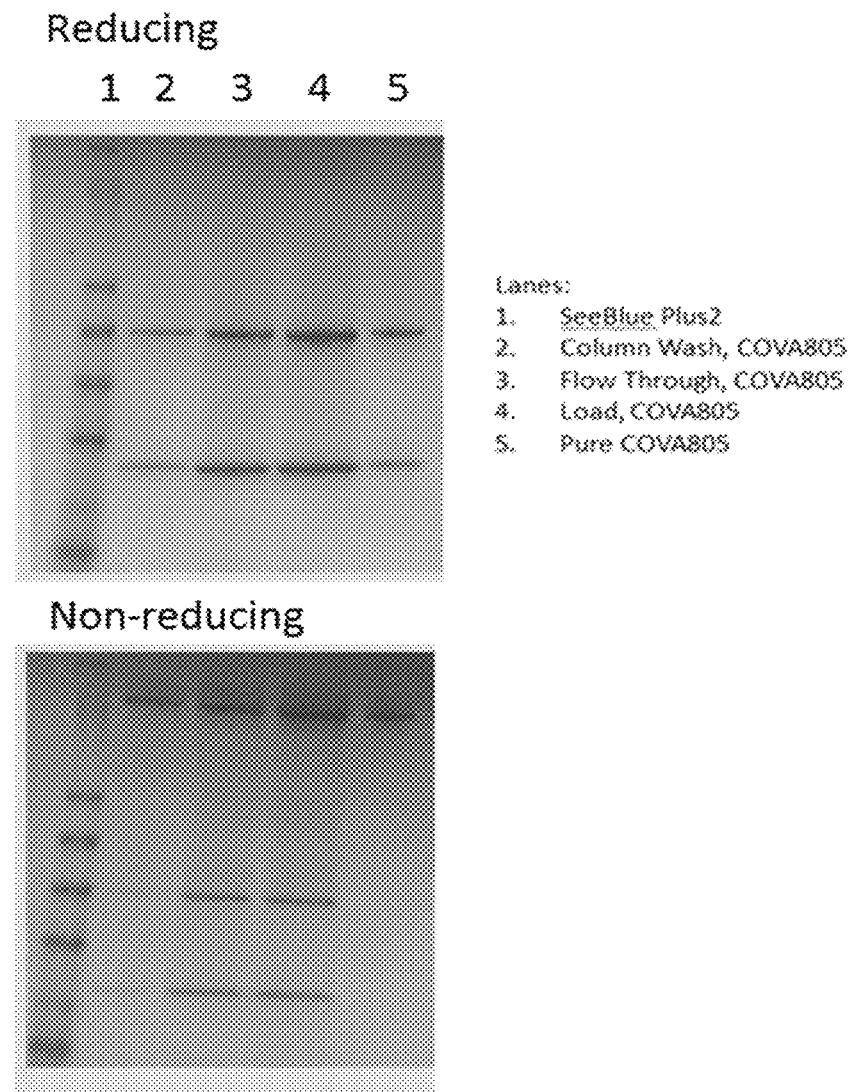
Figure 2D:
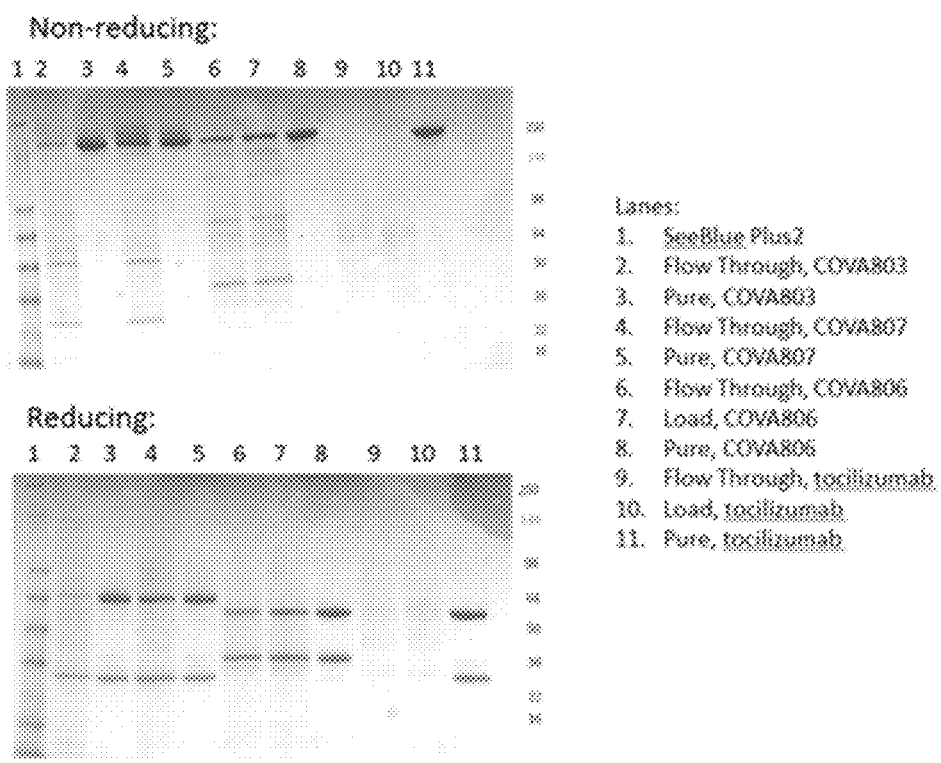
Figure 4A:
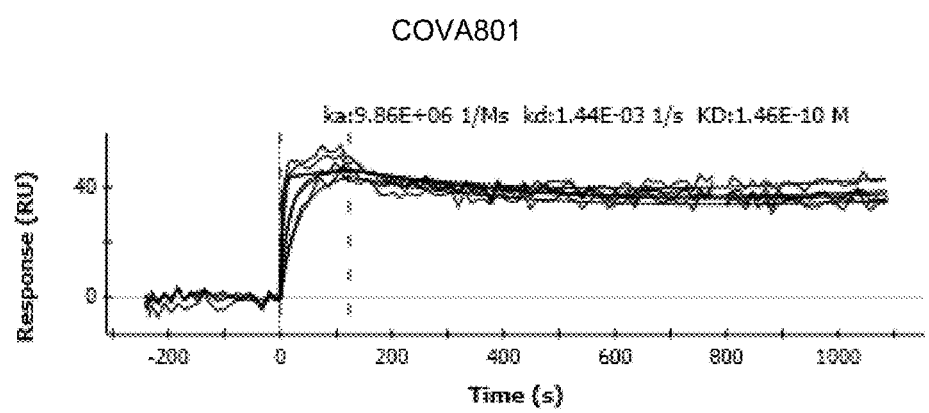
FIG. 4A-4L shows kinetic binding analysis of FynomAb interaction with recombinant human IL-17A.
Figure 4B:
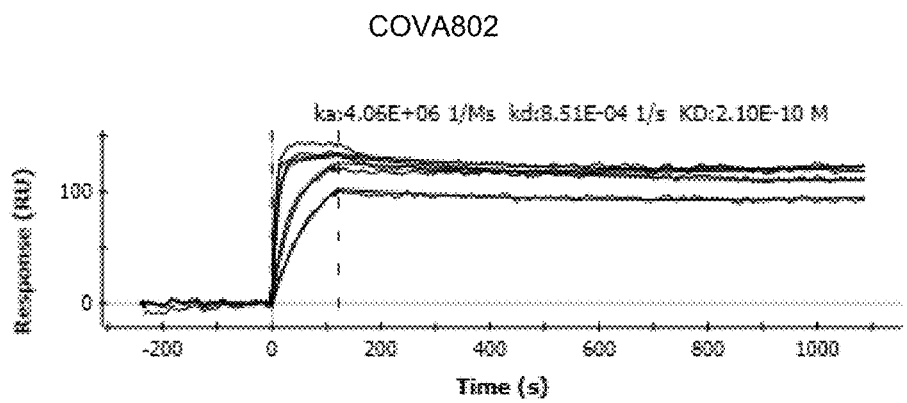
Figure 4C:
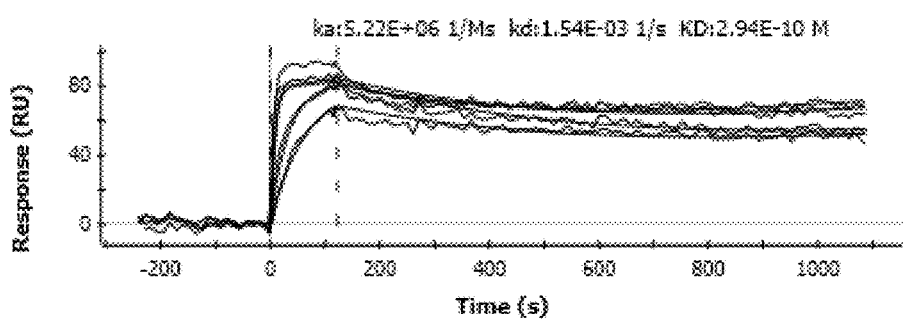
Figure 4D:
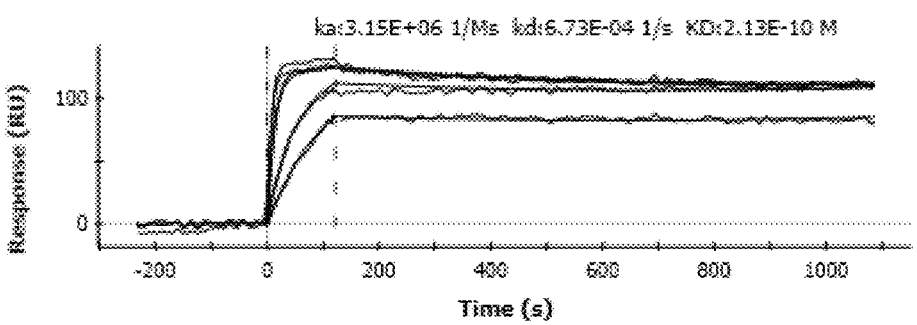
Figure 4E:
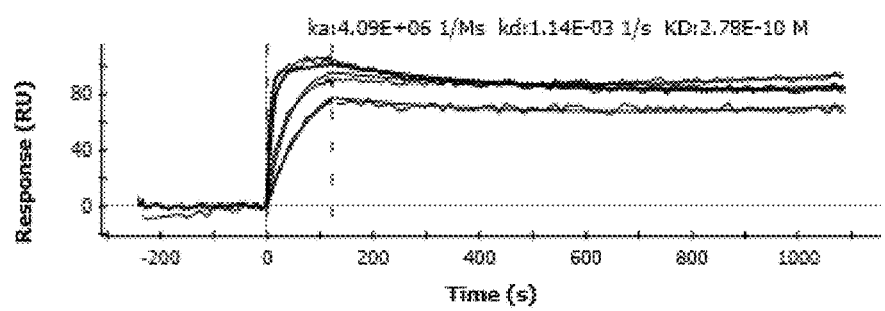
Figure 4F:
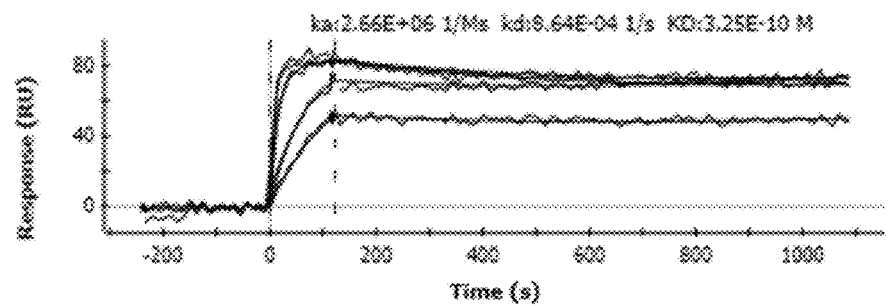
Figure 4G:
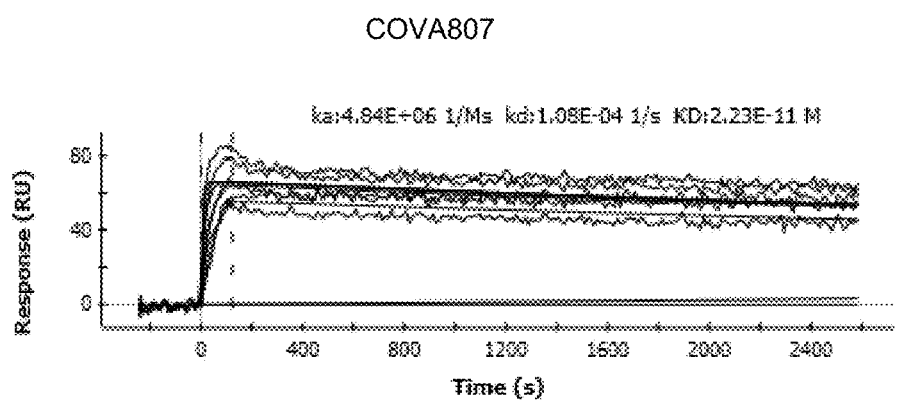
Figure 4H:
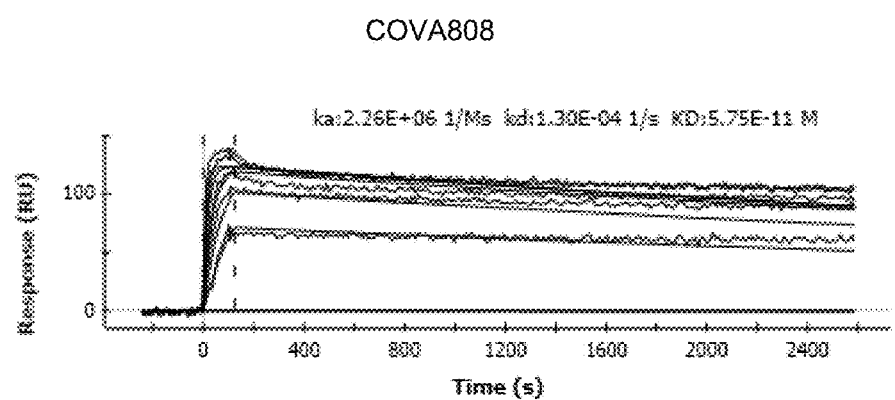
Figures 4I, 4J:
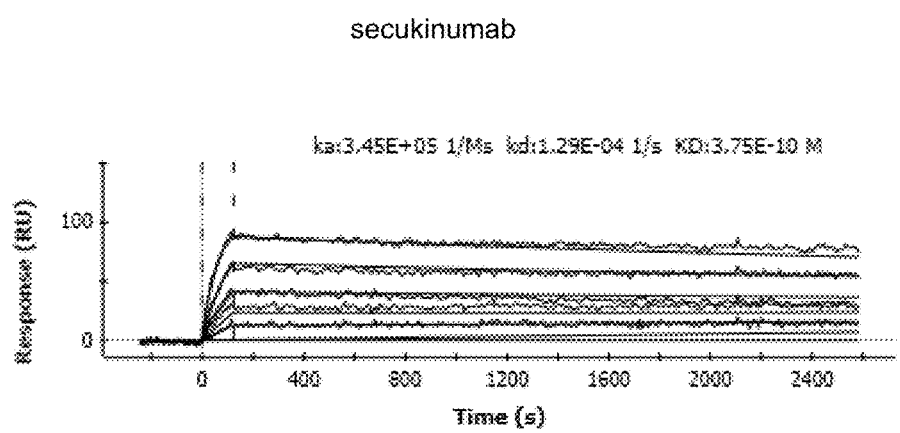
Figure 4K:
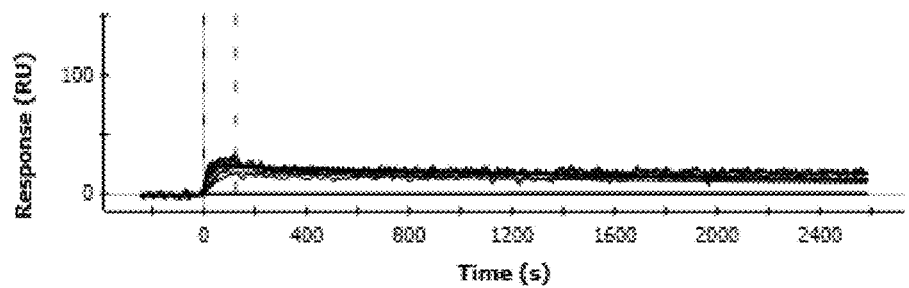
Figure 4L:
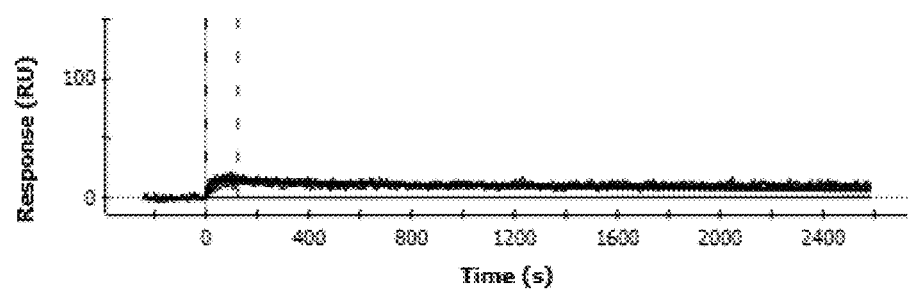

SDS-PAGE analysis was performed on three separate lots of each FynomAb and tocilizumab. Five micrograms of each protein were electrophoresed under both reducing and non-reducing conditions on 4-20% Tris-glycine gradient gels using Tris-glycine SDS sample and running buffers. Gels were stained overnight with Coomassie brilliant blue (SimplyBlue SafeStain, Invitrogen) and de-stained until sufficiently clear with distilled water. Results are shown in FIG. 1 (SDS-PAGE analysis of transient CHO material), FIGS. 2 and 3 (SDS-PAGE analysis of stable CHO material made for mouse PK study).

Example 4

Analytical HPLC-SEC

Three separate lots of FynomAbs were assessed by analytical HPLC-SEC. One lot of transient CHO material, and the other two lots were produced internally from stably transfected CHO cell lines. Ten micrograms of each FynomAb protein were injected onto a Zenix-C SEC-300 column (Sepax Technologies) using PBS as the mobile phase with a flow rate of 1 mL/min. Absorbance at A280 was monitored. The presence of the fynomer retards the elution of the FynomAbs compared to Actemra to varying degrees, presumably due to a secondary interaction between the solid phase and the fynomers. Soluble aggregation is observed as peaks eluting before the major peak of the FynomAb, and is most evident in the heavy chain fusion constructs COVA801, COVA803, COVA805 and COVA807.

The light chain fusions (COVA802, COVA804, COVA806 and COVA808 FynomAbs) had much cleaner SEC profiles, with no aggregation observed for COVA804 or COVA806 FynomAbs. These data are consistent with prior data, which also showed that the light chain fusions had cleaner SEC profiles with less apparent soluble aggregation.

Example 5

Affinity Measurements for Human IL-17a and Human IL-6R

To determine the affinity and kinetic parameters of FynomAb binding to human IL-17A and human IL-6R, an anti-human antibody was amine coupled to a GLM chip. The COVA801-808 FynomAbs or control antibodies were then captured as ligand, and either IL-17A or IL-6R was flowed as the analyte. PBST was utilized as mobile phase, and regeneration was achieved with two 15-second injections of 100 mM HCl. Secukinumab was used as a positive control for IL-17A binding and as a negative control for IL-6R binding. Tocilizumab and/or Actemra were used as positive controls for IL-6R binding and as negative controls for IL-17-A binding.

Secukinumab was used as a positive control for IL-17A binding and as a negative control for IL-6R binding. The VH and VL chains of Secukinumab are as follows:

Variable Light chain (SEQ ID NO: 33)
Signal sequence (underlined), variable domain (kappa) (in bold)
MSVPTQVLGLLLLWLTDARCEIVLTQSPGTLSLSPGERATLSCRASQSVS

SSYLAWYQQKPGQAPRLLIYGASSRATGIPDRFSGSGSGTDFTLTISRLE

PEDFAVYYCQQYGSSPCTFGQGTRLEIKRTVAAPSVFIFPPSDEQLKSGT

-continued
ASVVCLLNNFYPREAKVQWKVDNALQSGNSQESVTEQDSKDSTYSLSSTL

TLSKADYEKHKVYACEVTHQGLSSPVTKSFNRGEC*

Variable Heavy chain (SEQ ID NO: 34)
Signal sequence (underlined), variable domain (kappa) (in bold)
MEWSWVFLFFLSVTTGVHSEVQLVESGGGLVQPGGSLRLSCAASGFTFSN

YWMNWVRQAPGKGLEWVAAINQDGSEKYYVGSVKGRFTISRDNAKNSLYL

QMNSLRVEDTAVYYCVRDYYDILTDYYIHYWYFDLWGRGTLVTVSSASTK

GPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCD

KTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQGN

VFSCSVMHEALHNHYTQKSLSLSPG*

Tocilizumab and/or Actemra were used as a positive control for IL-6R binding and as negative controls for IL-17-A binding.

IL-17a Binding

Representative sensorgrams for IL-17A binding by the COVA801-808 FynomAbs as well as for secukinumab (positive control and reference) and tocilizumab or Actemra (negative controls) are shown in FIG. 4. A summary of the kinetic binding data from multiple studies for multiple lots of each FynomAb and secukinumab is summarized in Table 4. Sensorgrams shown are for COVA801-808, separate lots of tocilizumab (toc), commercial Actemra, and secukinumab (sec).

Fit kinetics are in fairly good agreement with other data values, and most constructs have an apparent KD similar to secukinumab. The assessment of binding to IL17A is confounded by complex association with the FynomAbs, as seen by significant deviation from 1:1 binding in the FynomAb data sets but not in the secukinumab data set. It appears that significant re-binding of IL-17A is occurring that is more easily observed with a prolonged dissociation phase. Thus, the reported kinetic and affinity values for the FynomAb/IL-17A interaction should be carefully interpreted. Although COVA807 and COVA808 had lower KD values, the significant deviation from 1:1 binding of IL-17A by these two FynomAbs may account for their apparent higher affinity. We observed inferior functional activity of the COVA807 FynomAb in the IL-17A functional assay (see HT29 IL-17A functional assay data below).

TABLE 4

Summary of SPR data for FynomAb binding to human IL-17A

| FynomAb | Avg. $k_a$ (1/Ms) | Avg. $k_d$ (1/s) | Avg. KD (nM) | St. dev. of KD (M) | No. of experiments |
|---------|-------------------|------------------|--------------|--------------------|---------------------|
| COVA801 | 6.17E+06 | 4.11E−04 | 4.86E−11 | ±6.61E−10 | 4 |
| COVA802 | 3.26E+06 | 2.53E−04 | 7.82E−11 | ±1.14E−10 | 4 |
| COVA803 | 4.96E+06 | 3.57E−04 | 6.89E−11 | ±1.26E−10 | 5 |
| COVA804 | 2.42E+06 | 1.29E−04 | 4.68E−11 | ±6.78E−11 | 8 |
| COVA805 | 3.53E+06 | 5.81E−04 | 1.43E−10 | ±1.92E−10 | 2 |
| COVA806 | 2.01E+06 | 2.33E−04 | 9.98E−11 | ±1.27E−10 | 5 |

TABLE 4-continued

Summary of SPR data for FynomAb binding to human IL-17A

| FynomAb | Avg. $k_a$ (1/Ms) | Avg. $k_d$ (1/s) | Avg. KD (nM) | St. dev. of KD (M) | No. of experiments |
|---|---|---|---|---|---|
| COVA807 | 4.34E+06 | 9.66E−05 | 2.23E−11 | ±7.07E−14 | 2 |
| COVA808 | 2.95E+06 | 7.97E−05 | 3.11E−11 | ±1.74E−11 | 5 |
| secukinumab | 6.46E+05 | 1.01E−04 | 4.47E−10 | ±3.97E−10 | 4 |

Figure 5:
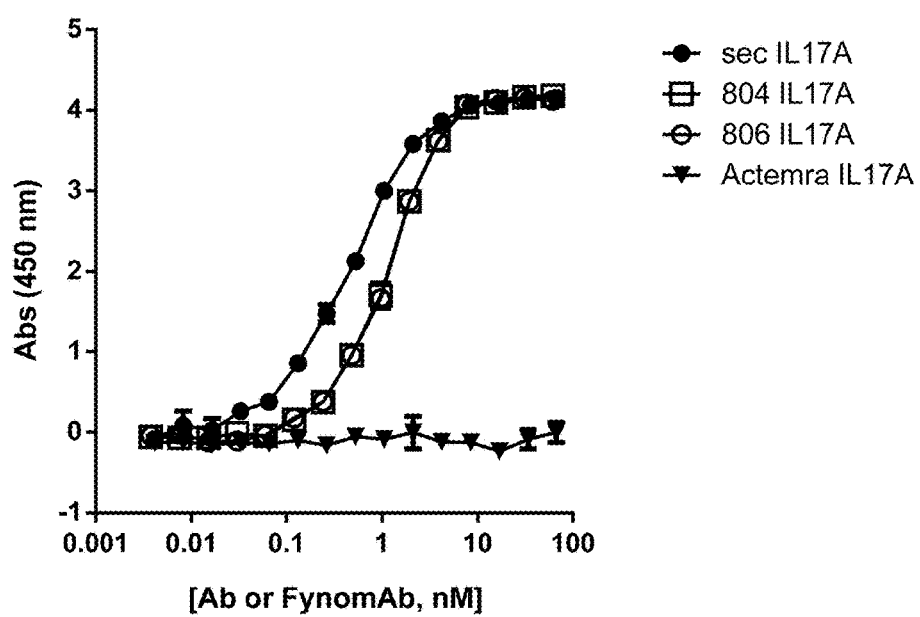
FIG. 5 shows IL-17A binding ELISA for COVA804 and COVA806.
Figure 6A:
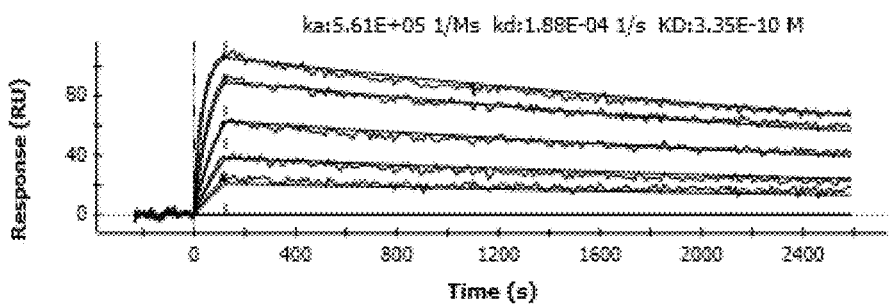
FIG. 6A-6L shows kinetic binding analysis of FynomAb interaction with recombinant human IL-6R.
Figure 6B:
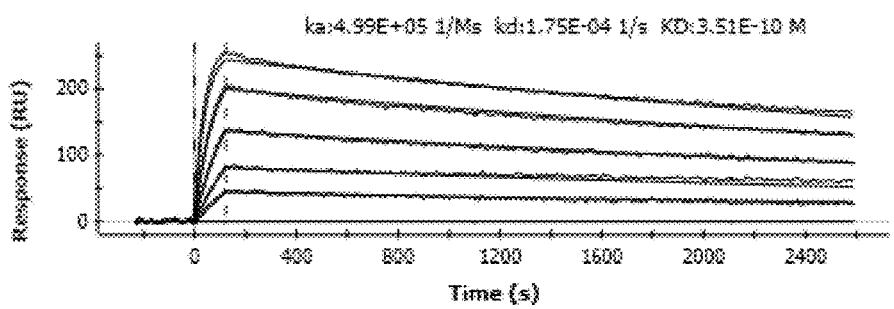
Figure 6C:
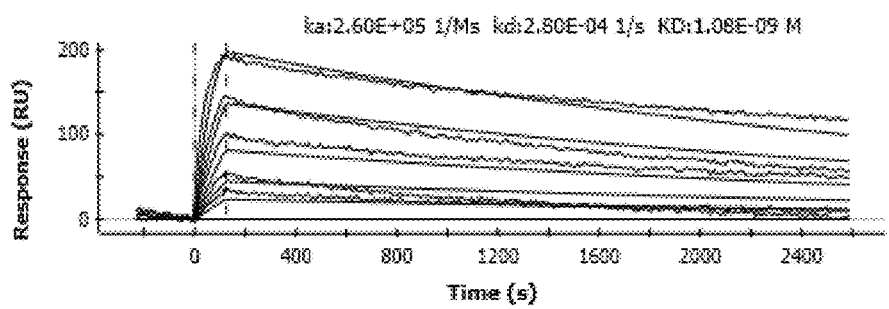
Figure 6D:
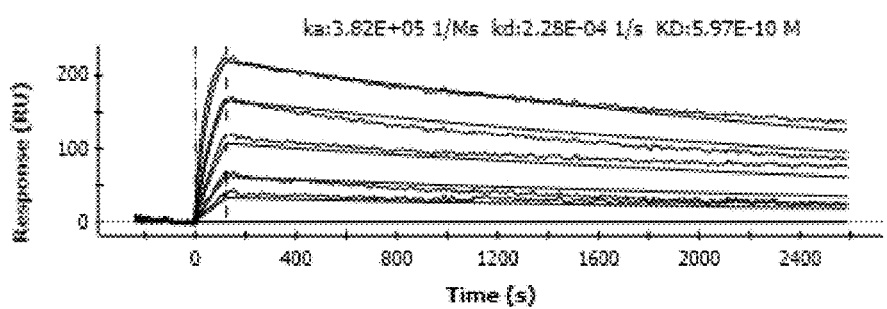
Figures 6E, 6F:
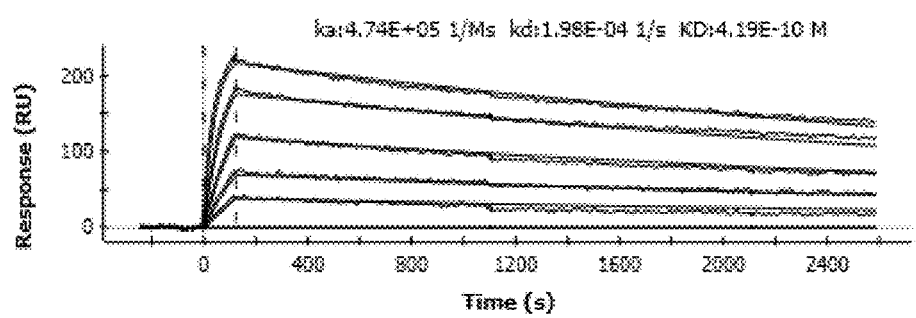
Figure 6G:
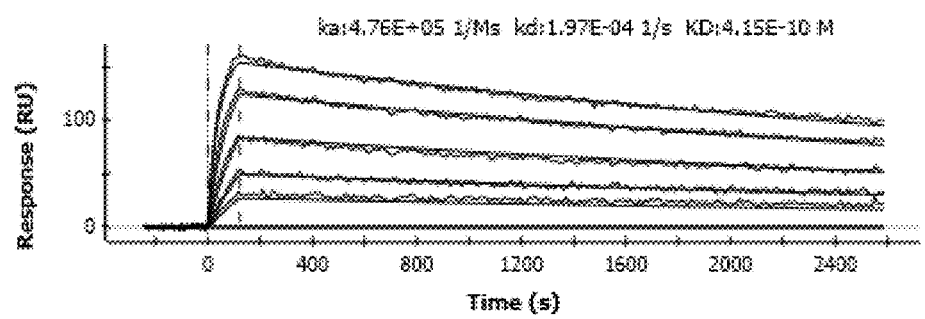
Figure 6H:
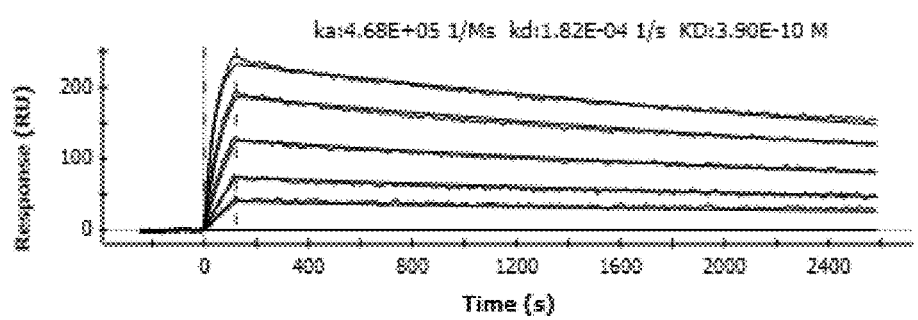
Figure 6I:
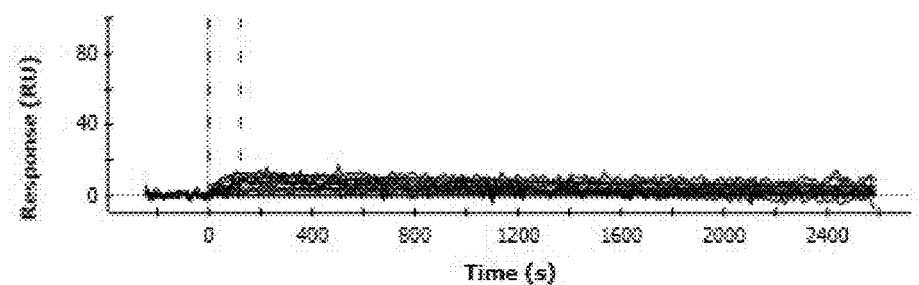
Figure 6J:
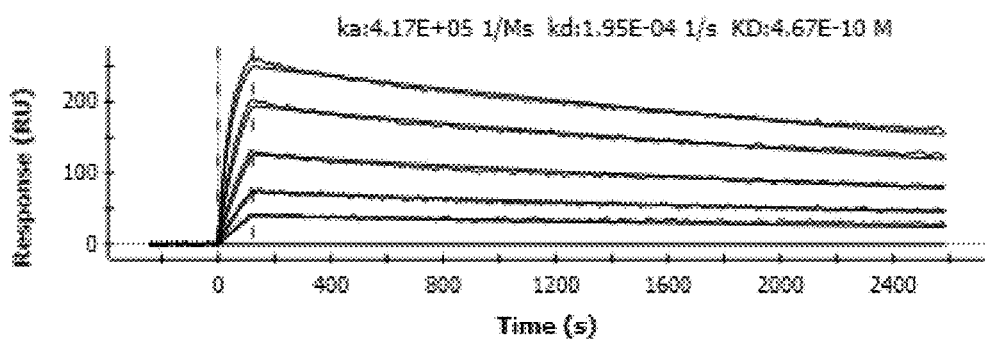
Figure 6K:
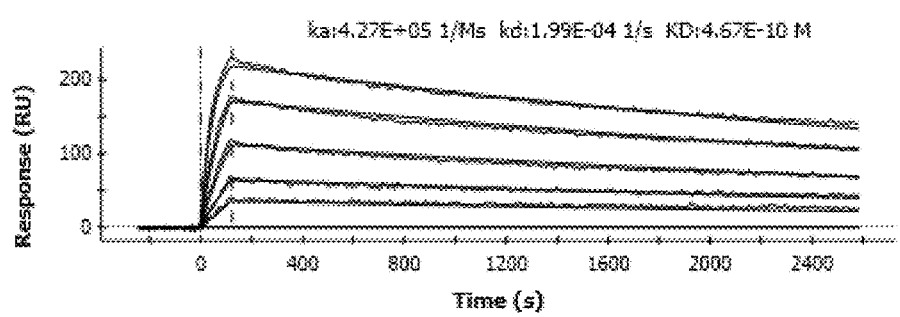
Figure 6L:
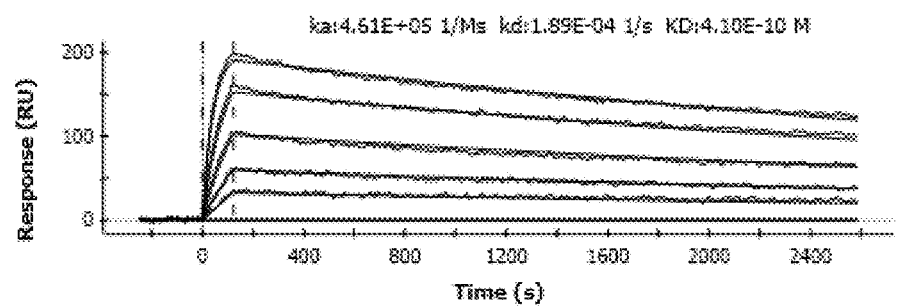

Due to the complex association of the FynomAb constructs with the recombinant IL-17A homodimer, a simple binding ELISA was performed to study the specificity and relative affinities of COVA804 and COVA806 for human IL-17A. Briefly, 1 µg/mL of recombinant human IL-17A in PBS was coated on an ELISA plate, followed by blocking with BSA and incubation with 0-10 µg/mL test antibody or FynomAb. A goat-anti-human antibody conjugated to horseradish peroxidase was used to detect binding using TMB. The results of concentration-response binding to IL-17A were highly reproducible over four studies, with a representative study shown in FIG. 5. Binding to human IL-17A was assessed by ELISA for COVA804 (804), COVA806 (806) and secukinumab (sec). Actemra was used as a negative control for IL-17A binding. The EC50 values for the different constructs were as follows: secukinumab=0.36±0.12 nM; COVA804=1.02±0.24 nM; COVA806=0.98±0.23 nM. Thus, these data support the SPR data which demonstrates that FynomAbs COVA804 and COVA806 have a similar affinity for IL-17A as secukinumab.

IL-6R Binding

Representative sensorgrams for IL-6R binding by the COVA801-808 FynomAbs as well as for tocilizumab and Actemra (positive controls and reference) and secukinumab (negative control) are shown in FIG. 6. Assessment of the FynomAb/IL6R interaction by SPR is very reproducible, and the interaction can easily be modeled with a classical Langmuir fit as shown in FIG. 6. Sensorgrams shown are for COVA801-808, separate lots of tocilizumab (toc), commercial Actemra, and secukinumab (sec). A summary of the kinetic binding data from multiple studies for multiple lots of each FynomAb and tocilizumab is summarized in Table 5. These data show that the presence of the Fynomers on the C-termini of either the light or heavy chain does not affect binding of IL-6R to the parental antibody. All FynomAbs show very similar binding kinetics to one another and to the parent antibody tocilizumab.

TABLE 5

Summary of SPR data for FynomAb binding to human IL-6R

| FynomAb | Avg. $k_a$ (1/Ms) | Avg. $k_d$ (1/s) | Avg. KD (nM) | St. dev. of KD (M) | No. of experiments |
|---|---|---|---|---|---|
| COVA801 | 4.99E+05 | 1.50E−04 | 2.97E−10 | ±0.29E−10 | 4 |
| COVA802 | 4.72E+05 | 1.68E−04 | 3.95E−10 | ±1.45E−10 | 6 |
| COVA803 | 3.63E+05 | 2.19E−04 | 6.04E−10 | ±3.31E−10 | 6 |
| COVA804 | 4.08E+05 | 2.01E−04 | 6.32E−10 | ±3.71E−10 | 9 |
| COVA805 | 6.13E+05 | 1.78E−04 | 3.14E−10 | ±1.49E−10 | 2 |
| COVA806 | 4.34E+05 | 1.72E−04 | 5.14E−10 | ±3.20E−10 | 5 |
| COVA807 | 6.92E+05 | 1.89E−04 | 3.07E−10 | ±1.53E−10 | 2 |
| COVA808 | 4.25E+05 | 1.70E−04 | 5.46E−10 | ±3.04E−10 | 4 |
| tocilizumab | 4.73E+05 | 1.86E−04 | 4.17E−10 | ±1.06E−10 | 4 |
| Actemra | 4.13E+05 | 1.91E−04 | 4.99E−10 | ±1.42E−10 | 6 |

Example 6

HT-29 IL-17a Inhibition Assay

To assess the bioactivity of the COVA801-808 FynomAbs against human IL-17A, HT-29 cells (ATCC, #HTB-38) were stimulated with IL-17A (1.9 nM) in the presence of various concentrations of each FynomAb, ranging from 100 nM to 6 pM. Secukinumab was used as a positive control for blockade of IL-17A function. For each condition, 20,000 viable cells were added and incubated for 48 hours in a flat bottom 96-well plate at 37° C. and 5% CO2. Each condition was tested in duplicate.

Stimulation of HT29 cells with IL17A resulted in the production and release of Groα into cell supernatant. Groα concentrations in the supernatants were then measured by ELISA, using the DuoSet ELISA kit from R&D Systems (DY275). The ELISA was performed according to the manufacturer's manual (except all antibodies were used at 1:200).

The means of duplicate results were plotted with standard deviations, and IC50 values were calculated using a four-parameter dose-response inhibition function in GraphPad Prism®. Representative data from multiple studies using three different lots of the COVA801-808 FynomAbs are shown in FIGS. 7-9. IC50 values calculated from the representative data are shown in Table 6. All FynomAbs showed similar activity against IL-17A as the reference secukinumab, and all FynomAbs were able to achieve complete blockade at higher concentrations. COVA806 consistently showed the most potent activity against IL-17A and was consistently more potent than secukinumab.

TABLE 6

Figure 7A:
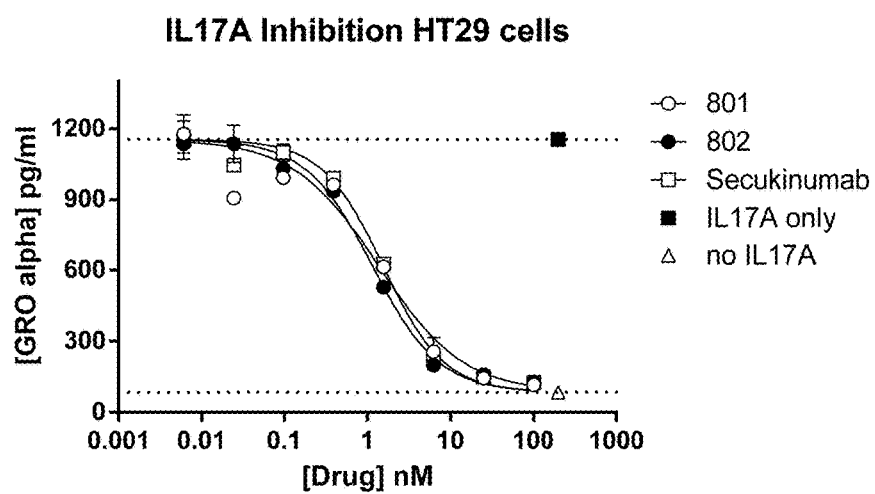
FIG. 7A-7D shows HT-29 IL-17A assay with transient CHO FynomAb material.
Figure 7B:
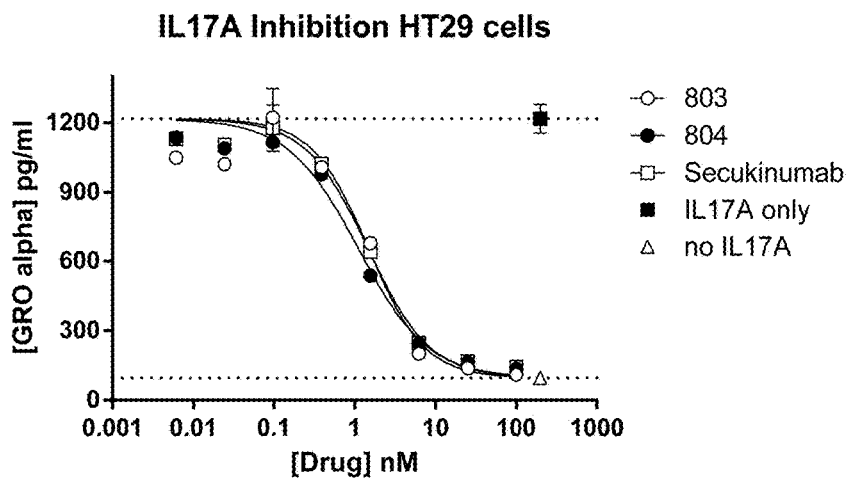
Figure 7C:
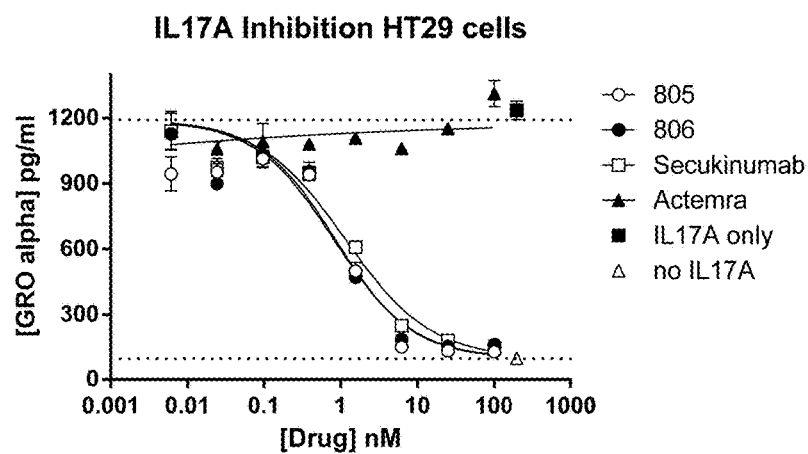
Figure 7D:
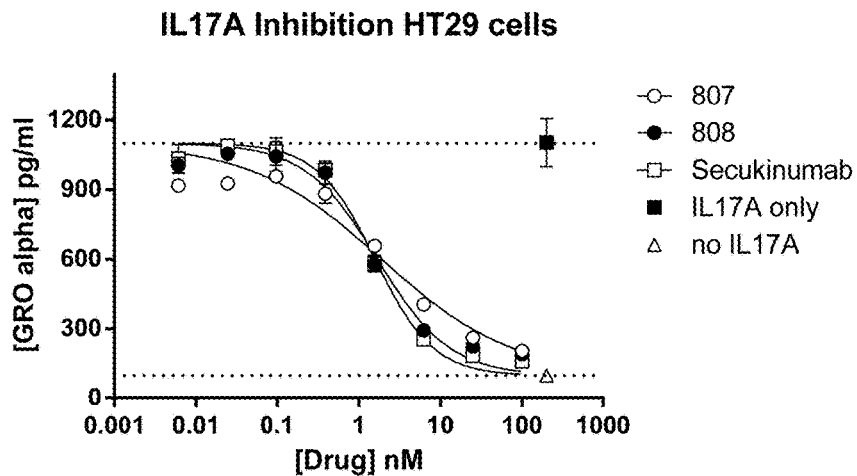

| FIG. 7A | 801 | 802 | Secukinumab |
|---|---|---|---|
| IC50 | 1.362 | 1.148 | 1.542 |
| FIG. 7B | 803 | 804 | Secukinumab |
| IC50 | 1.476 | 1.104 | 1.457 |
| FIG. 7C | 805 | 806 | Secukinumab |
| IC50 | 0.8135 | 0.8537 | 1.155 |
| FIG. 7D | 807 | 808 | Secukinumab |
| IC50 | 1.929 | 1.702 | 1.597 |
| FIG. 8A | 801 in-house | 802 in-House | Secukinumab |
| IC50 | 1.599 | 1.783 | 2.395 |
| FIG. 8B | 803 in-house | 804 in-House | Secukinumab |
| IC50 | 2.625 | 2.317 | 2.560 |
| FIG. 8C | 805 in-house | 806 in-House | Secukinumab |
| LogIC50 | 0.2796 | 0.07429 | 0.2138 |
| FIG. 8D | 807 in-house | 808 in-House | Secukinumab |
| LogIC50 | 0.6443 | 0.4065 | 0.3166 |
| FIG. 9A | 801 | 802 | Secukinumab |
| IC50 | 1.520 | 0.9410 | 1.259 |
| FIG. 9B | 803 | 804 | Secukinumab |
| IC50 | 12.118 | 1.507 | 1.960 |
| FIG. 9C | 806 | 808 | Secukinumab |
| IC50 | 1.132 | 2.036 | 2.070 |

Example 7

HEK-Blue™ IL-6R Inhibition Assay

To assess the bioactivity of the anti-IL-6R part in COVA801-808 constructs, HEK Blue IL-6 cells (Invivogen, hkb-il6) were stimulated with IL-6 (15 pM) in the presence of various concentrations of FynomAb, ranging from 500 nM to 0.2 nM. The inhibitors were pre-incubated with the cells for 30 minutes before addition of IL-6. As controls, medium only, or medium containing IL-6 (15 pM) were used. Also, tocilizumab or Actemra was used as a positive control for IL-6R blockade. For each sample, 50,000 viable cells were added and incubated for 20-24 hours in a well of a 96-well plate at 37° C., 5% CO2. Each condition was tested in triplicate.

Addition of IL-6 to the cells resulted in stimulation of the IL-6R signaling pathway, which activated the STAT3-inducible SEAP reporter gene. SEAP in the supernatants was measured using the HEK-Blue™ detection reagent (Invivogen, hb-det2), used according to the manufacturer's manual.

The means of triplicate results were plotted, with standard deviation. IC50-values were calculated using a four-parameter dose-response inhibition function in GraphPad Prism®. Representative data from multiple studies using three different lots of the COVA801-808 FynomAbs are shown in FIGS. 10-12 below. IC50 values calculated from the representative data are shown in Table 7. All FynomAbs from all three lots showed similar blockade of IL-6R to commercial grade Actemra and tocilizumab. These data are similar to other data and indicate that the presence of the IL-17A binding fynomers on the tocilizumab backbone Ab does not affect the IL-6R blocking activity of these FynomAbs.

TABLE 7

Figure 10A:
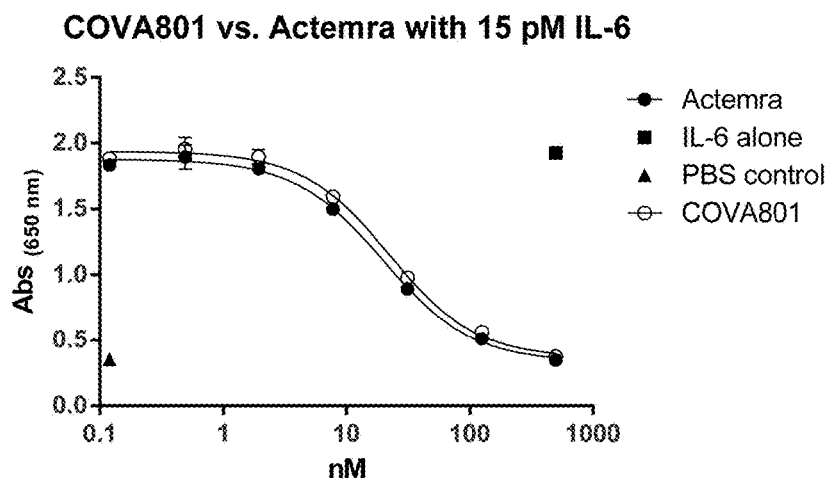
FIG. 10A-10I shows HEK-Blue IL-6R inhibition assay with transient CHO FynomAb material.
Figure 10B:
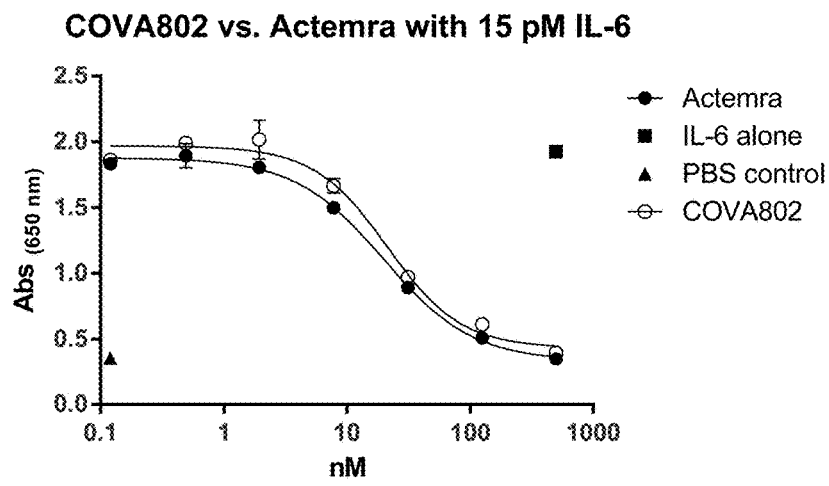
Figure 10C:
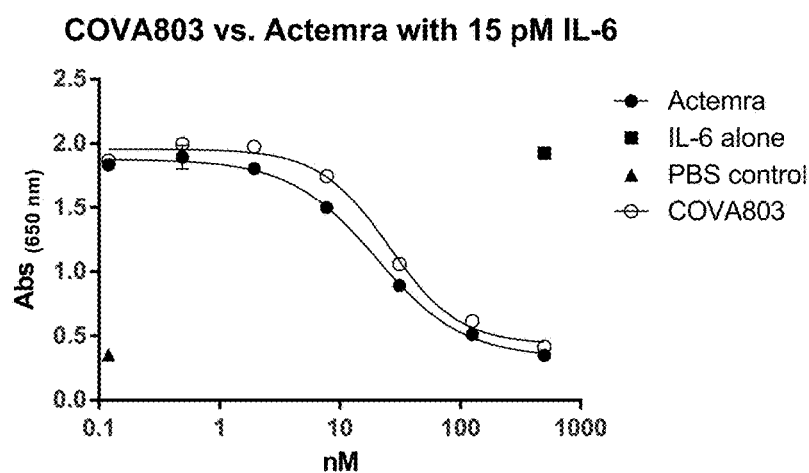
Figure 10D:
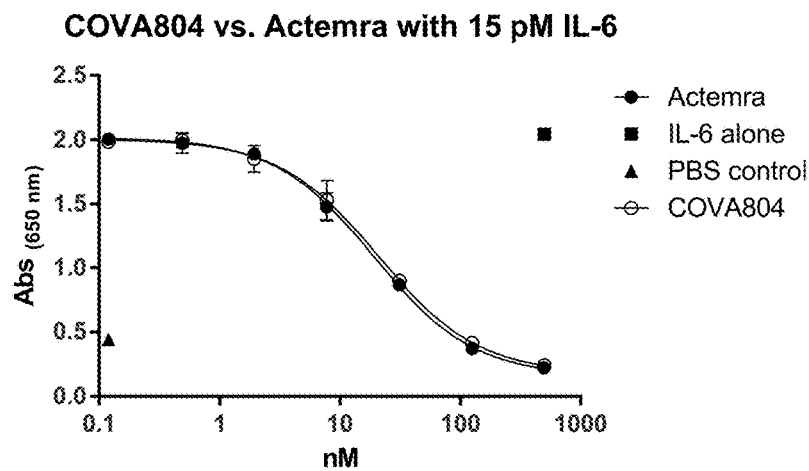
Figure 10E:
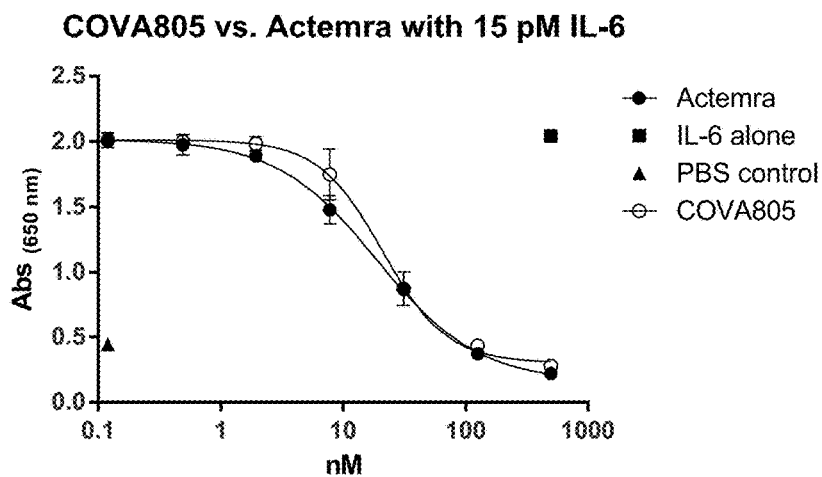
Figure 10F:
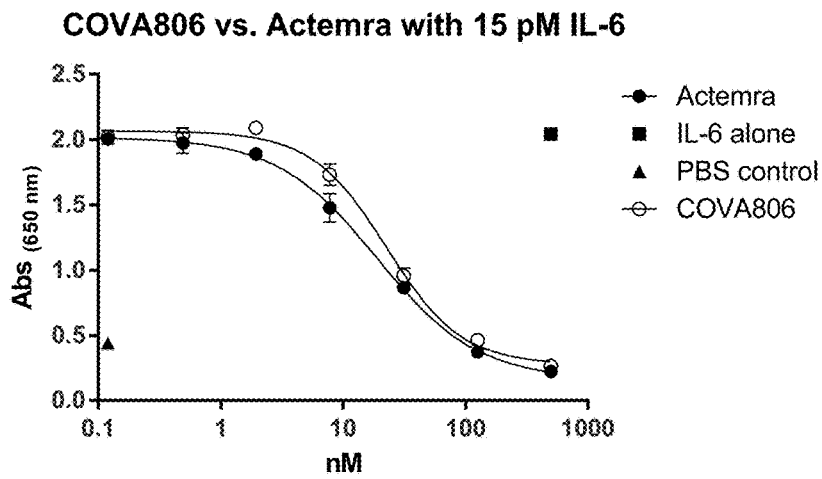
Figure 10G:
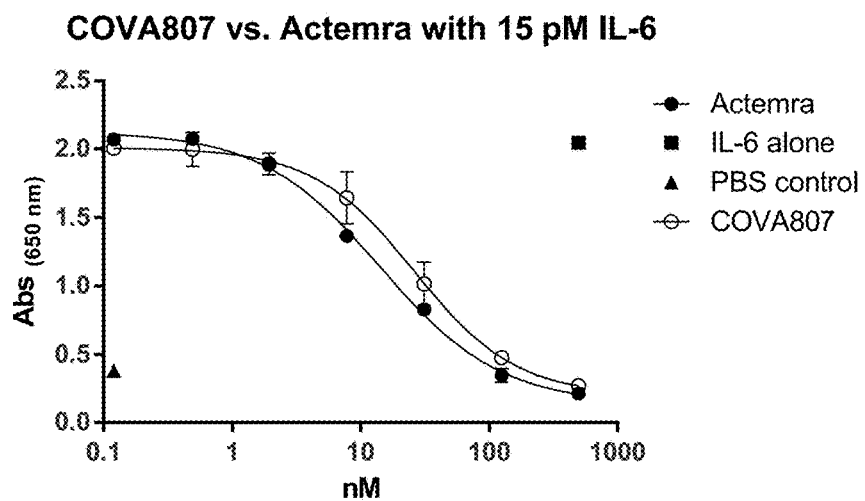
Figure 10H:
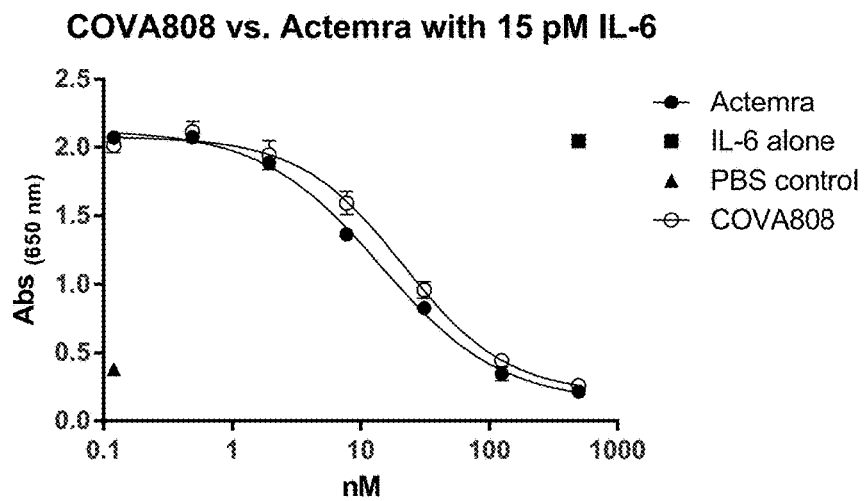
Figure 10I:
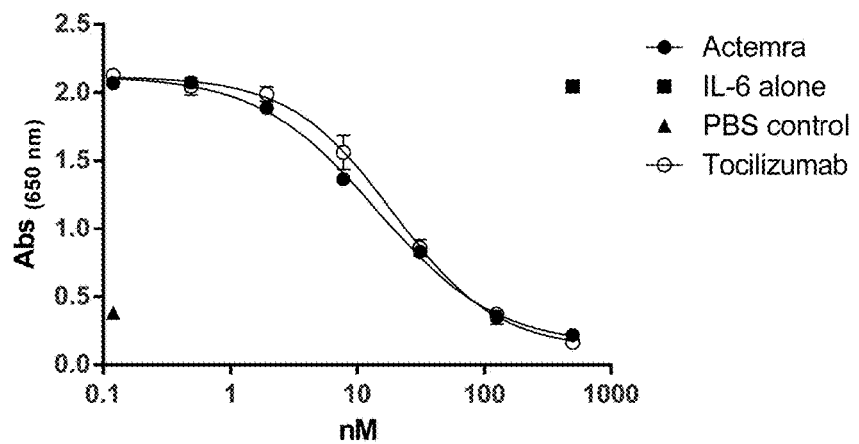
Figure 11A:
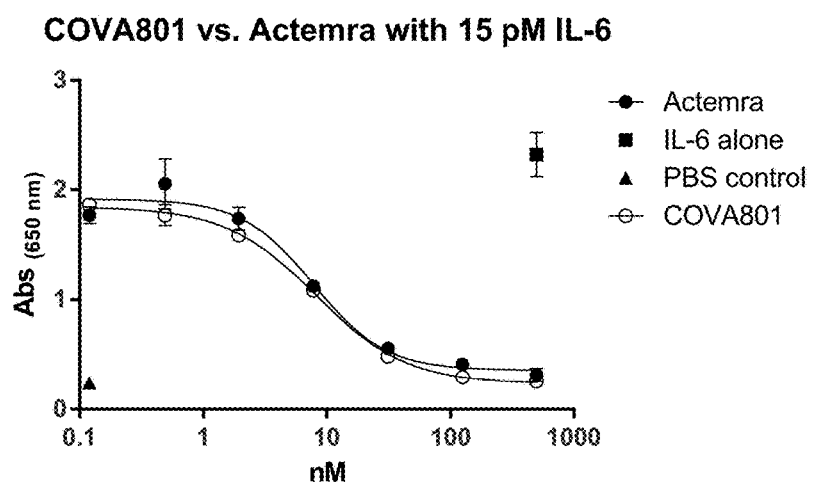
FIG. 11A-11I shows HEK-Blue IL-6R inhibition assay with stable CHO pool FynomAb material produced for mouse PK study.
Figure 11B:
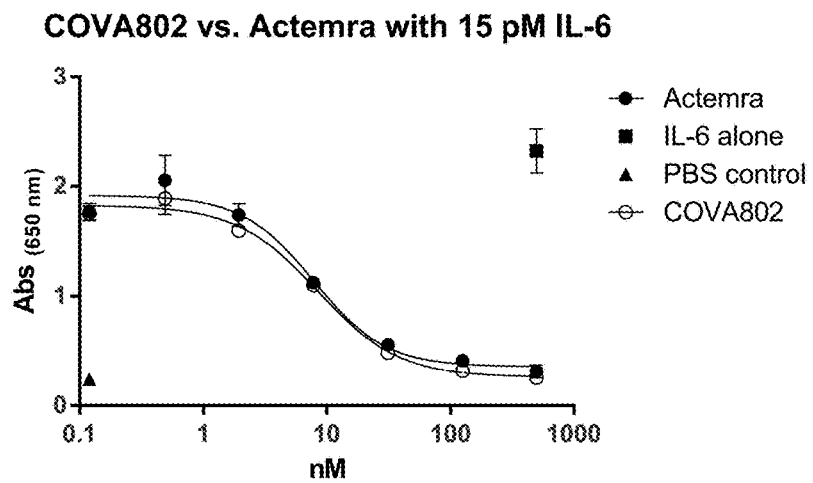
Figure 11C:
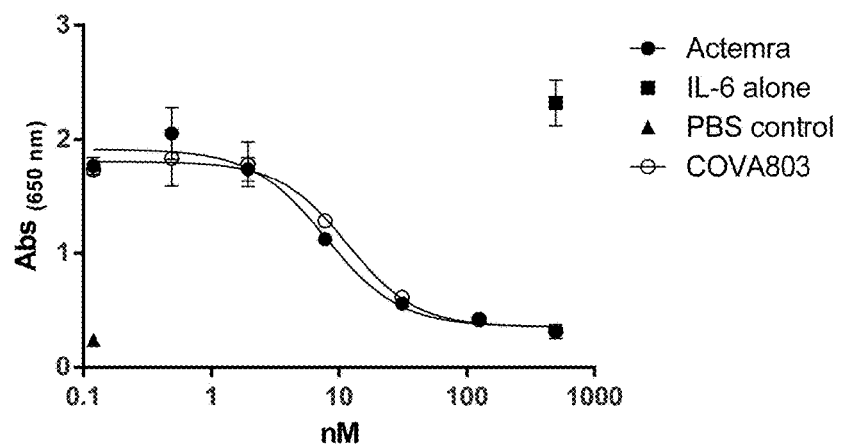
Figure 11D:
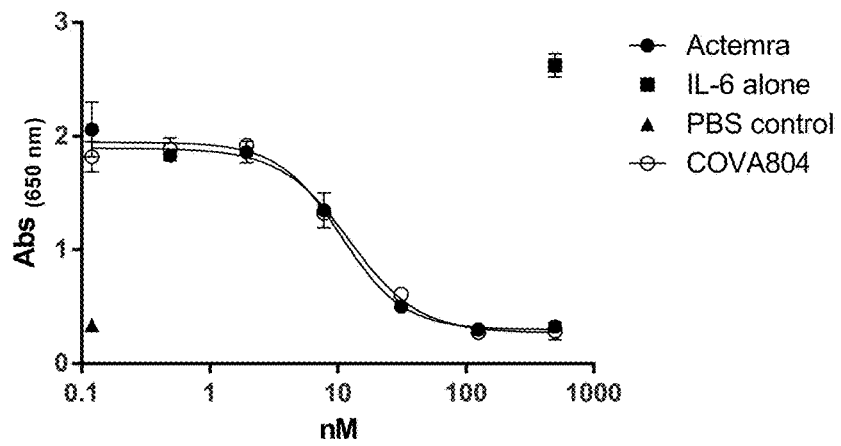
Figure 11E:
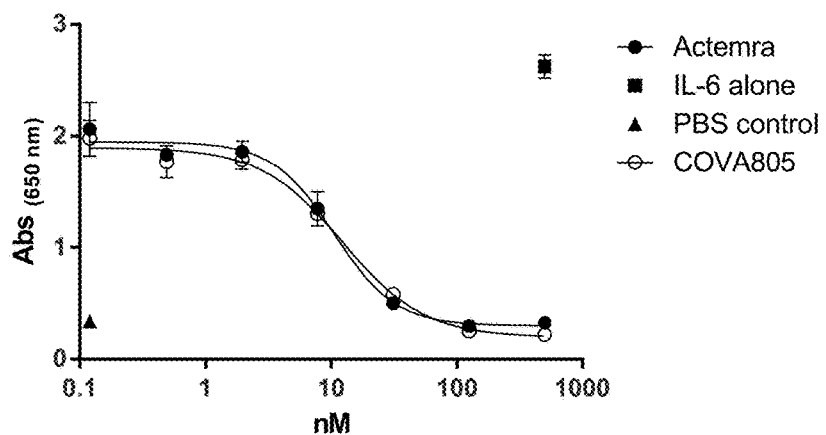
Figure 11F:
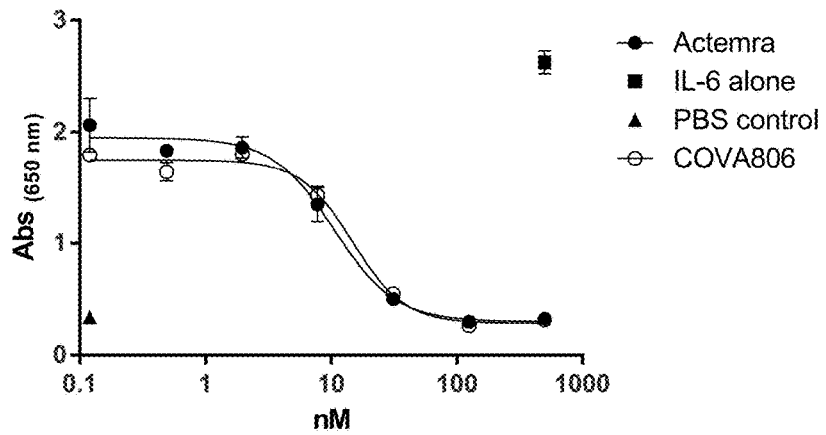
Figure 11G:
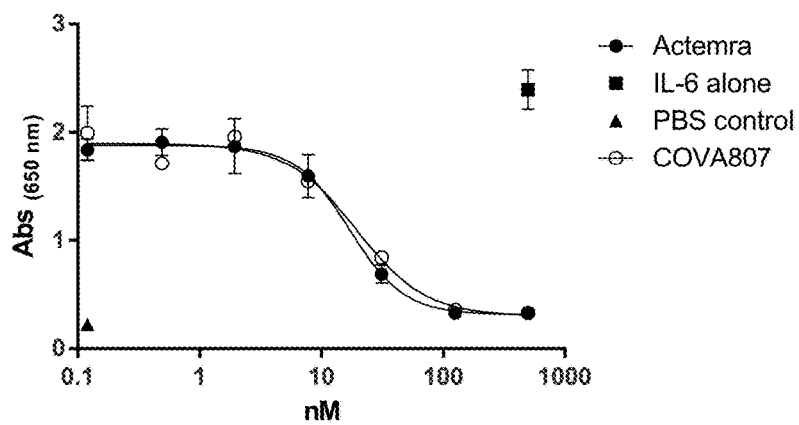
Figure 11H:
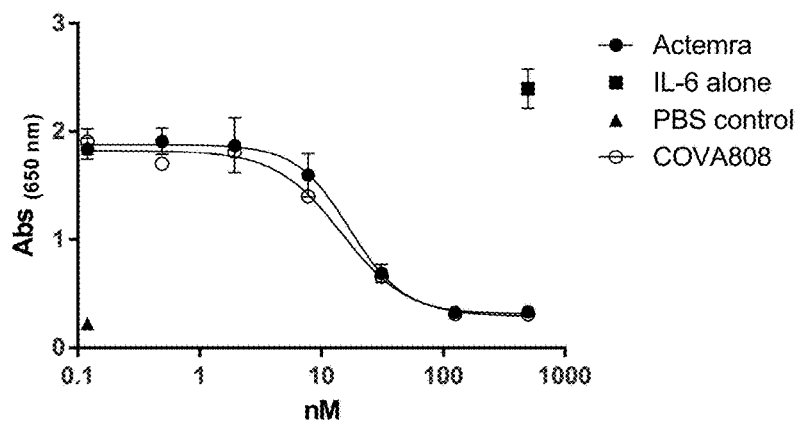
Figure 11I:
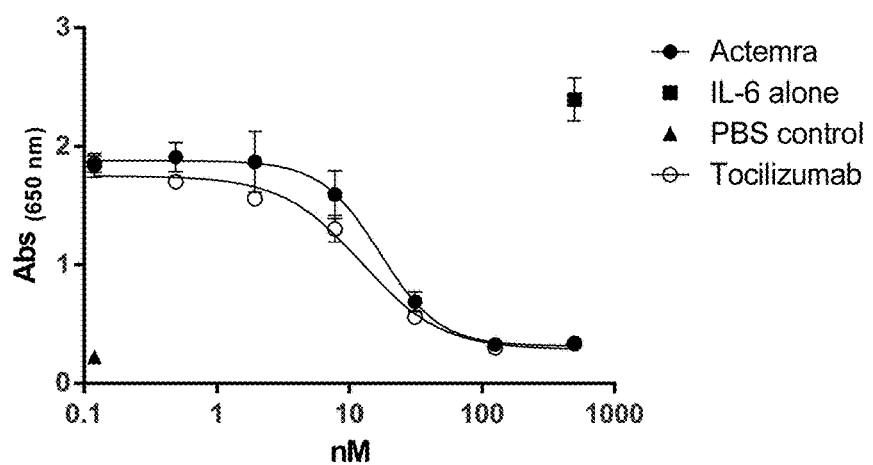
Figure 12A:
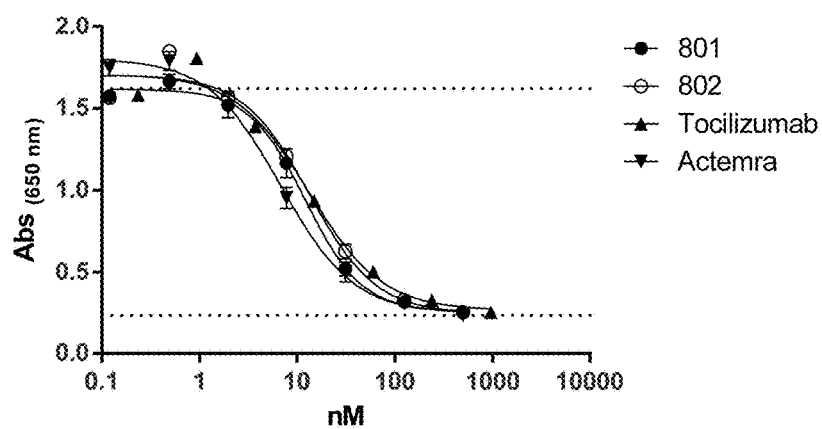
FIG. 12A-12C shows HEK-Blue IL-6R inhibition assay with stable CHO pool FynomAb material produced for cynomolgus (cyno) PK study.
Figure 12B:
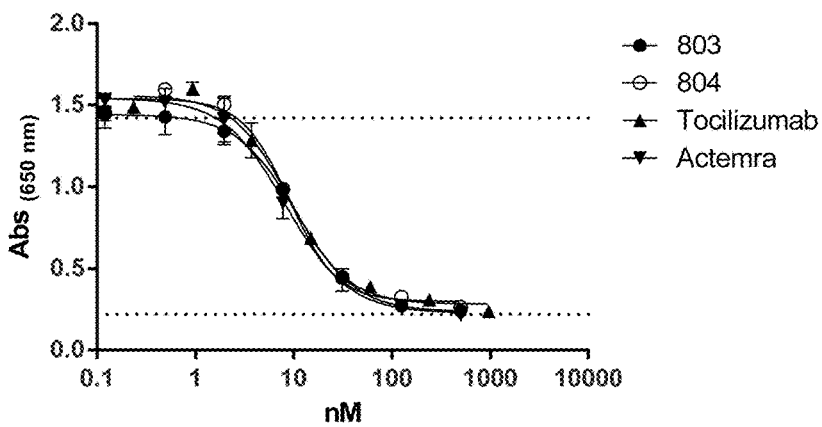
Figure 12C:
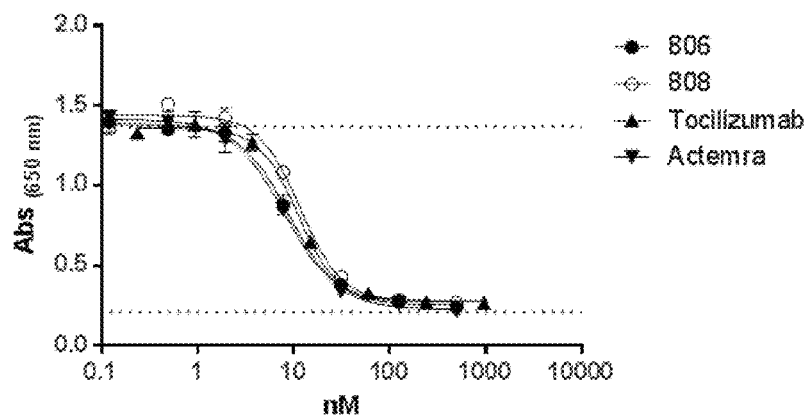

| | | | | |
|---|---|---|---|---|
| FIG. 10A | | Actemra | | COVA801 |
| IC50 | | 19.96 | | 22.28 |
| FIG. 10B | | Actemra | | COVA802 |
| IC50 | | 19.96 | | 21.29 |
| FIG. 10C | | Actemra | | COVA803 |
| IC50 | | 19.96 | | 25.52 |
| FIG. 10D | | Actemra | | COVA804 |
| IC50 | | 19.09 | | 20.84 |
| FIG. 10E | | Actemra | | COVA805 |
| IC50 | | 19.09 | | 21.14 |
| FIG. 10F | | Actemra | | COVA806 |
| IC50 | | 19.09 | | 22.80 |
| FIG. 10G | | Actemra | | COVA807 |
| IC50 | | 14.37 | | 26.18 |
| FIG. 10H | | Actemra | | COVA808 |
| IC50 | | 14.37 | | 21.45 |
| FIG. 10I | | Actemra | | Tocilizumab |
| IC50 | | 14.37 | | 19.23 |
| FIG. 11A | | Actemra | | COVA801 |
| IC50 | | 7.869 | | 8.214 |
| FIG. 11B | | Actemra | | COVA802 |
| IC50 | | 7.869 | | 8.526 |
| FIG. 11C | | Actemra | | COVA803 |
| IC50 | | 7.869 | | 11.63 |
| FIG. 11D | | Actemra | | COVA804 |
| IC50 | | 10.55 | | 12.29 |
| FIG. 11E | | Actemra | | COVA805 |
| IC50 | | 10.55 | | 12.38 |
| FIG. 11F | | Actemra | | COVA806 |
| IC50 | | 10.55 | | 14.76 |
| FIG. 11G | | Actemra | | COVA807 |
| IC50 | | 17.05 | | 19.32 |
| FIG. 11H | | Actemra | | COVA808 |
| IC50 | | 17.05 | | 14.69 |
| FIG. 11I | | Actemra | | Tocilizumab |
| IC50 | | 17.05 | | 12.35 |
| FIG. 12A | 801 | 802 | Tocilizumab | Actemra |
| IC50 | 12.26 | 13.40 | 13.29 | 6.903 |
| FIG. 12B | 803 | 804 | Tocilizumab | Actemra |
| IC50 | 10.75 | 9.108 | 9.176 | 8.406 |
| FIG. 12C | 806 | 808 | Tocilizumab | Actemra |
| IC50 | 8.957 | 11.79 | 11.15 | 8.142 |

Example 8

Serum Stability Assay

Figure 13:
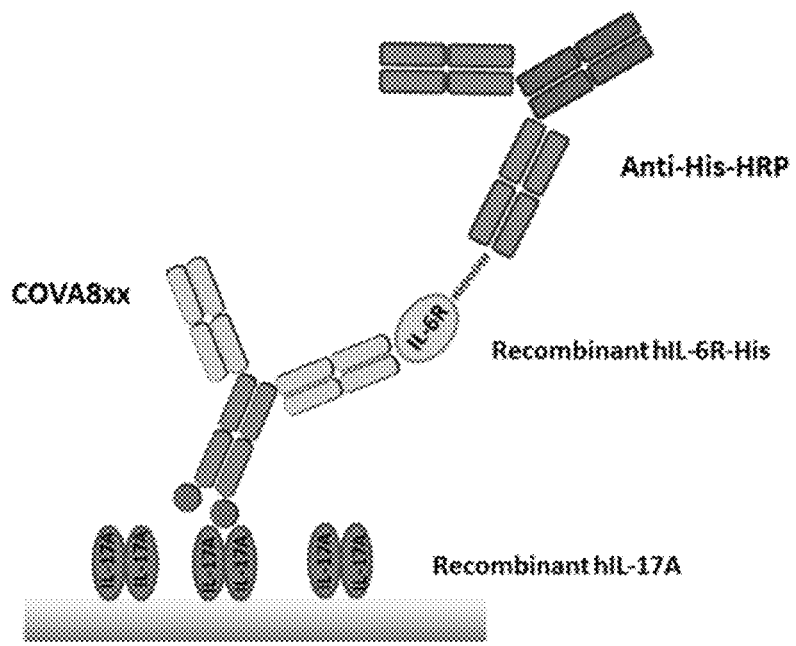
FIG. 13 shows serum stability dual binding ELISA setup.
Figure 14A:
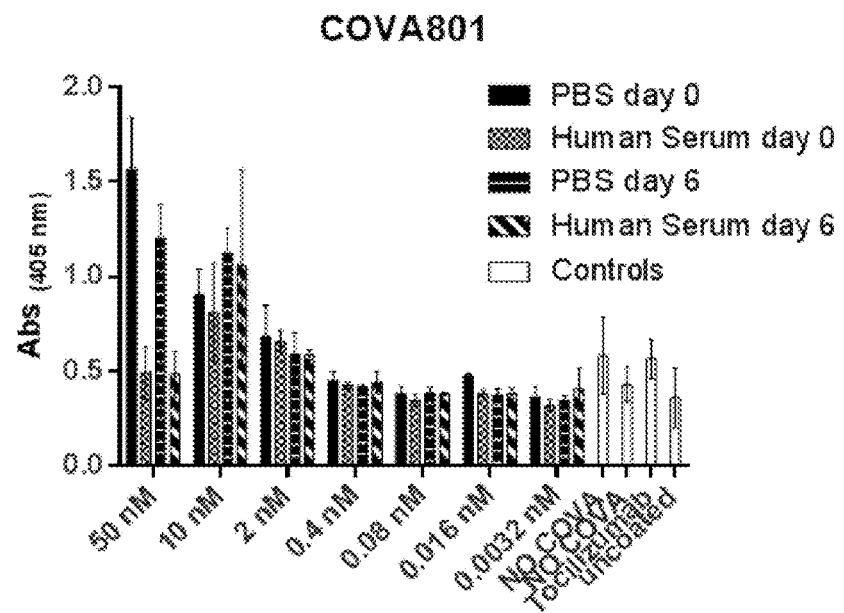
FIG. 14A-14H shows serum stability assessment of FynomAbs denoted COVA801-808.
Figure 14B:
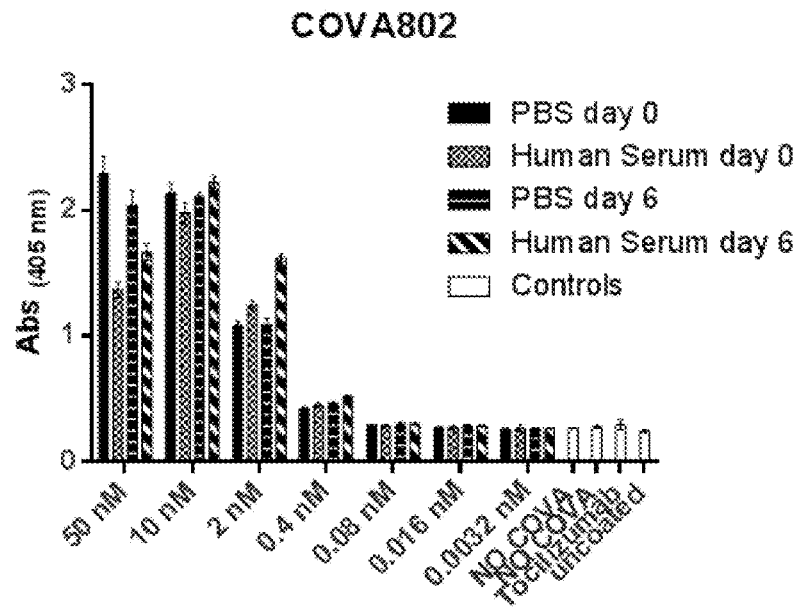
Figure 14C:
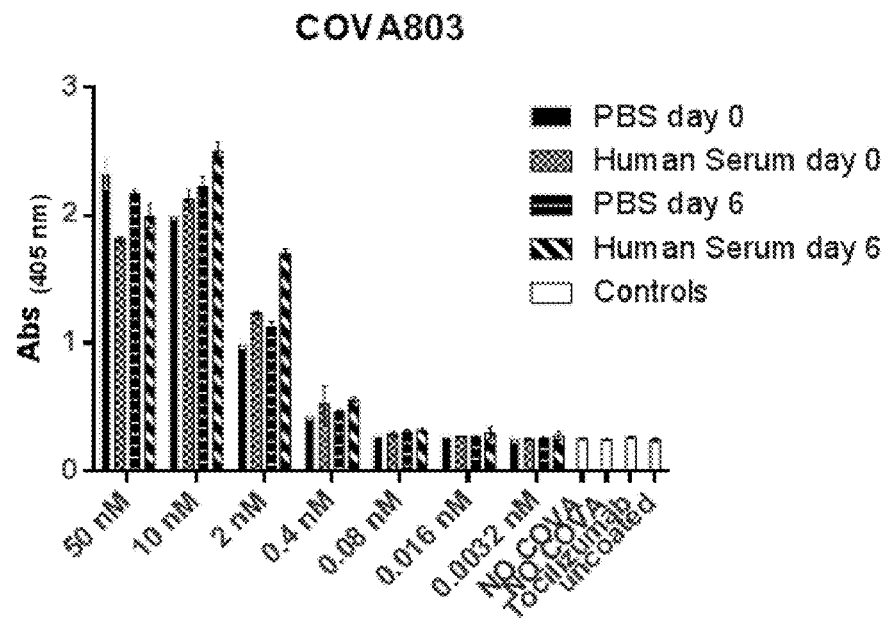
Figure 14D:
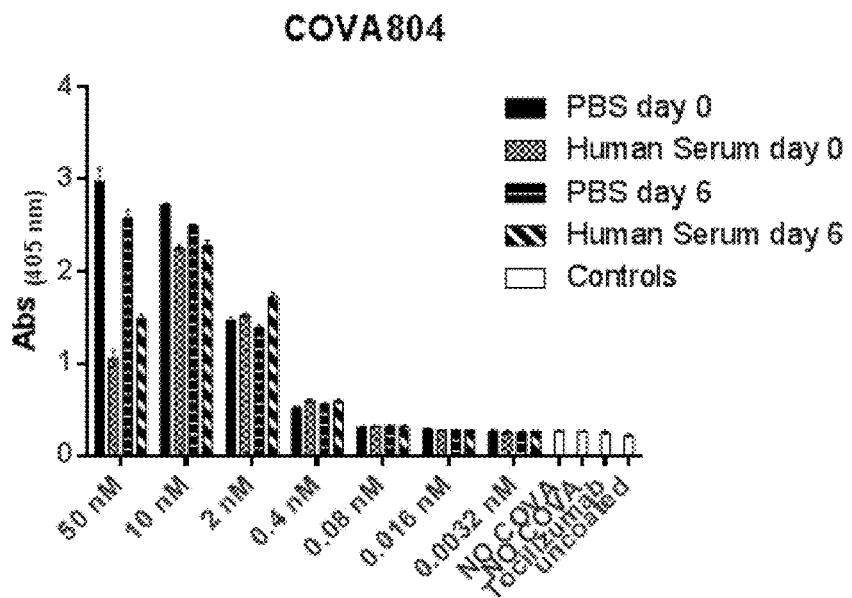
Figure 14E:
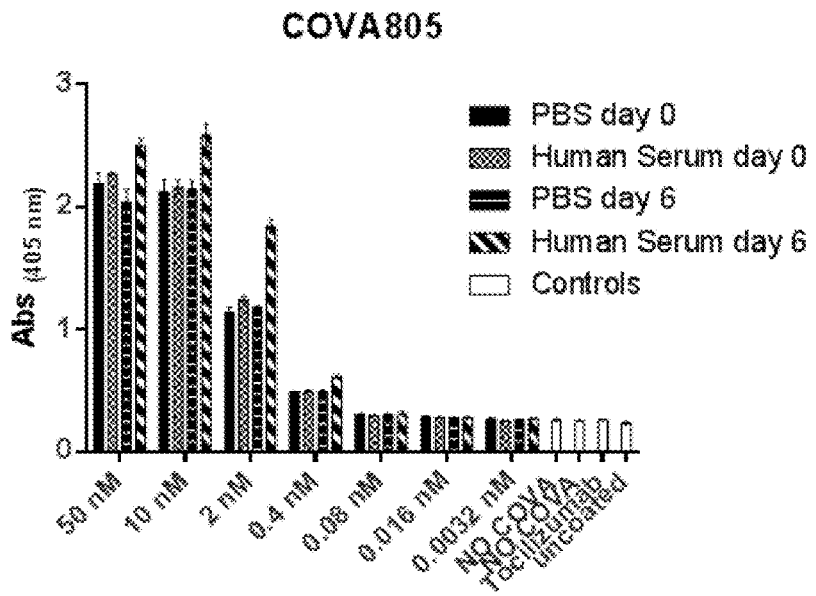
Figure 14F:
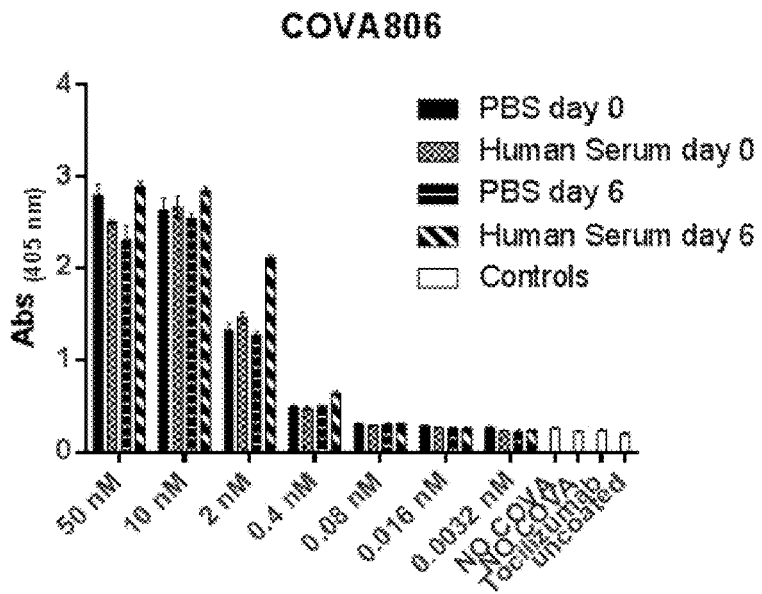
Figure 14G:
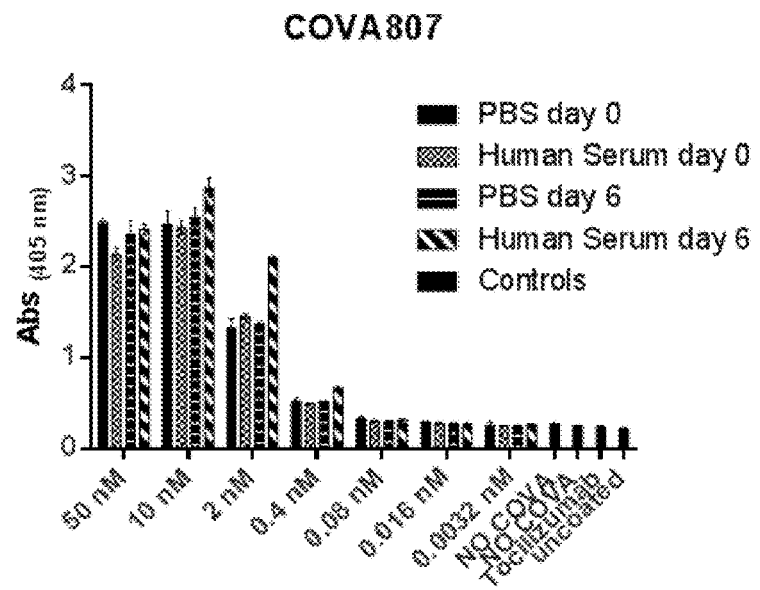
Figure 14H:
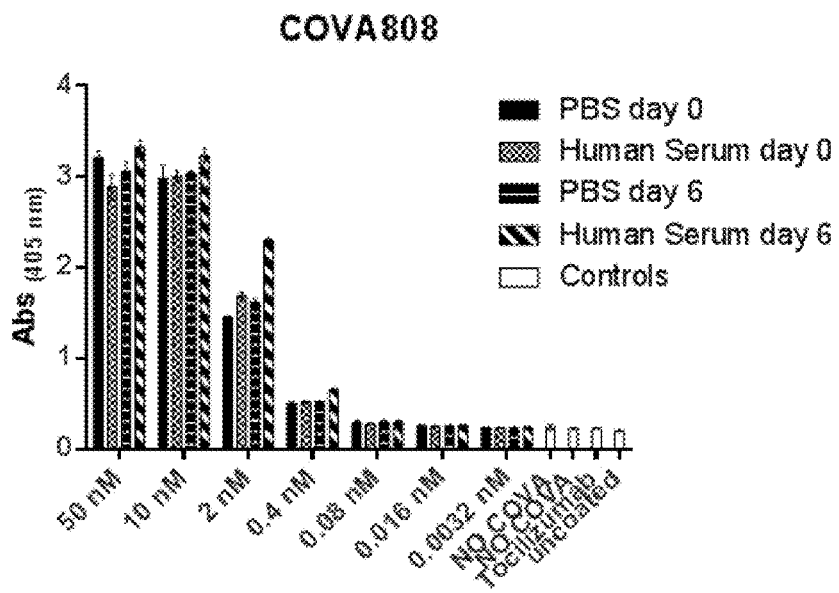

To assess the stability of each FynomAb in human serum, COVA801-808 FynomAbs were each incubated in 90% human serum (Sigma #H4522) for 6 days at 37° C. at a concentration of 10 µg/ml, and then tested in a sandwich ELISA to assess whether the FynomAbs retained their ability to bind both IL-17A and IL-6R. A sandwich ELISA was used to assess simultaneous binding of FynomAbs after incubation in PBS or human serum. The setup of the sandwich ELISA is shown in FIG. 13.

Briefly, human IL17A was coated on a Maxisorp 96 well plate at 5 µg/ml in PBS, and the FynomAb samples were diluted 5 fold in 1% BSA/PBST from 50 nM to 0.003 nM and added to the plates. His-tagged human IL-6R was then added to each well containing the FynomAbs and developed with an anti-His-HRP mAb. The plate was then washed and developed using TMB substrate (Sigma #T0440) and stopped with acid. The means of the triplicates were plotted along with standard deviations (see FIG. 14).

In more detail, COVA801-808 FynomAbs were incubated under the following conditions (a-d), and then assessed for retention of dual binding activity in the ELISA outlined in FIG. 10: a) dilution in PBS and immediately assayed (PBS day 0), b) dilution in PBS and stored for 6 days at 4° C. (PBS day 6), c) dilution in 90% human serum and immediately assayed (human serum day 0), d) dilution in 90% human serum and incubated for 6 days at 37° C. (human serum day 6).

Figure 15A:
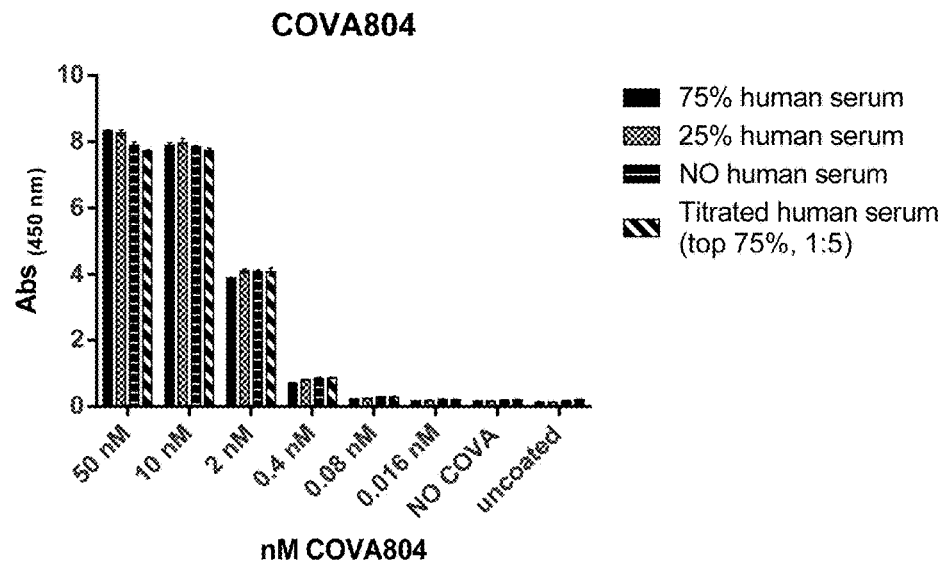
FIG. 15A-15B shows assessment of dual binding of FynomAbs denoted COVA804 and 806 in presence of human serum.
Figure 15B:
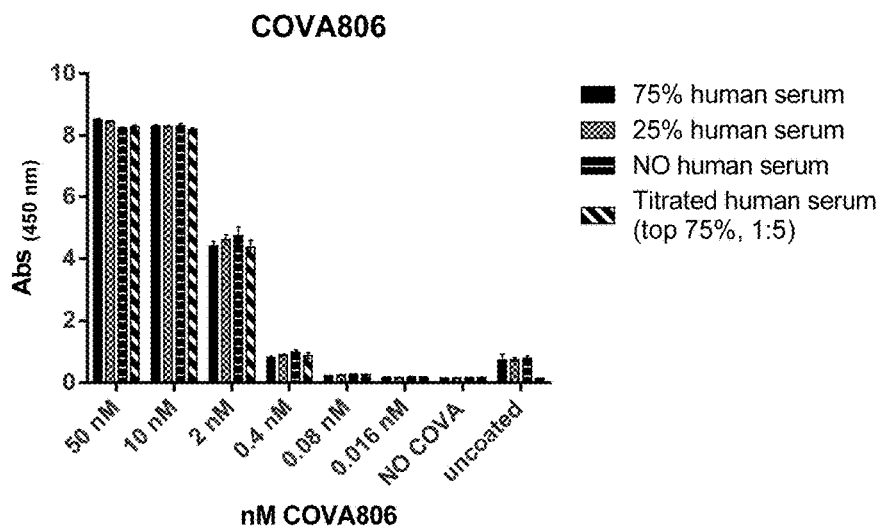

A separate set of control samples was incubated for 6 days at 4° C. in PBS (PBS day 6). Another set of control samples was diluted in human serum and immediately used in the assay (Human serum day 0). The purpose of the human serum day 0 samples was to assess whether the presence of human serum would affect the ability of the FynomAbs to bind both of its targets simultaneously. As shown in FIG. 14, the storage of the FynomAbs in human serum for 6 days did not decrease their binding activity (compare with human serum day 0) suggesting that all 8 FynomAbs are stable in human serum. As shown in FIG. 15, the dual binding activity of COVA804 and COVA806 was not affected in the presence of human serum.

Example 9

Simultaneous Binding of IL-6R and IL-17a

Data indicated that COVA801-808 FynomAbs were all able to simultaneously bind to human IL-17A and human IL-6R.

A cell-based flow cytometric assay was performed to demonstrate that the COVA801-808 FynomAbs could bind simultaneously to IL-6R on the cell surface and to soluble IL-17A. In this assay, HEK Blue IL-6 cells expressing human IL-6R on the surface (Invivogen hkb-il6) were used. Briefly, the COVA801-808 FynomAbs (or controls) were each incubated for 60 minutes with HEK-Blue IL-6 cells (or HEK-293 cells as a negative control) at various concentrations ranging from 300 nM to 5 pM. Following this primary incubation, binding of the constructs to IL-6R was detected using an anti-human-IgG antibody conjugated to the Alexa488 fluorophore (Invitrogen A11013).

Results are shown in FIG. 16. HEK-Blue-IL6 cells (IL6R+) or HEK-293 cells (IL6R−) were incubated with indicated FynomAbs followed by incubation with either anti-human IgG-Alexa488 to detect FynomAbs bound to cell surface or biotinylated IL-17A plus streptavidin APC to assess simultaneous binding. Tocilizumab was used as a positive control for IL-6R binding and as a negative control for IL-17A binding.

The data in FIGS. 16 A, C, E, G, I, K, M and O show that all 8 FynomAbs constructs as well as tocilizumab bind to HEK-Blue IL-6 cells expressing human IL-6R on the cell surface, but none of the constructs bind to control HEK-293 cells which do not express human IL-6R on the cell surface. In order to detect simultaneous binding to cell surface IL-6R and soluble human IL-17A, a separate study was performed in which the primary incubation with each construct was followed by a secondary incubation with biotinylated IL-17A (R&D 317-ILB) followed by incubation with streptavidin-allophycocyanin (APC; eBioscience 17-4317). As shown in FIGS. 16 B, D, F, H, J, L and P all 8 FynomAbs showed simultaneous binding to cell surface IL-6R and soluble IL-17A. As expected, tocilizumab was able to bind IL-6R expressed on the surface of the HEK Blue IL-6 cells but did not bind soluble IL-17A.

Example 10

Functional Activity of Bi-Specific FynomAbs in the Presence of Both IL-17A and IL-6R The data in FIGS. 15 and 16 show that the FynomAbs can simultaneously bind human IL-17A and human IL-6R. However, it is not clear whether binding of IL-6R by the mAb portion of the FynomAb influences the ability of the fynomer to bind and inhibit its ligand IL-17A. To address this issue, we performed the HT-29 IL-17A functional assay in the presence of soluble IL-6R to see if binding of IL-6R by the FynomAbs would reduce their binding and functional activity against IL-17A. The HT-29 IL-17A assay was performed exactly as described above, except that it was done both in the presence and in the absence of an excess of soluble IL-6R. Briefly, titrated amounts of COVA804 or COVA806 were mixed with IL-17A (1.9 nM) in the presence or absence of excess soluble IL-6R (20 nM), and then these mixtures were added to the IL-17A responsive cell line HT-29. The release of GROα was then measured after 48 hours by ELISA as described above. Secukinumab was used as a positive control for IL-17A blockade.

The results are shown in FIG. 17. HT-29 cells were stimulated with recombinant human IL-17A alone (top panel) or human IL-17A and soluble human IL-6R (bottom panel) in the presence of titrated amounts of COVA804 or COVA806, and GROα production was assessed by ELISA. Secukinumab was used as a positive control for IL-17A blockade.

As shown in FIG. 17 and Table 8, COVA804 and COVA806 both showed blockade of IL-17A-induced GROα production in the presence of excess soluble IL-6R, and similar IC50 values were observed in the presence and absence of IL-6R. These data suggest that binding of IL-6R does not affect the ability of the fynomer portion of the FynomAbs to bind and inhibit IL-17A.

TABLE 8

Figure 17A:
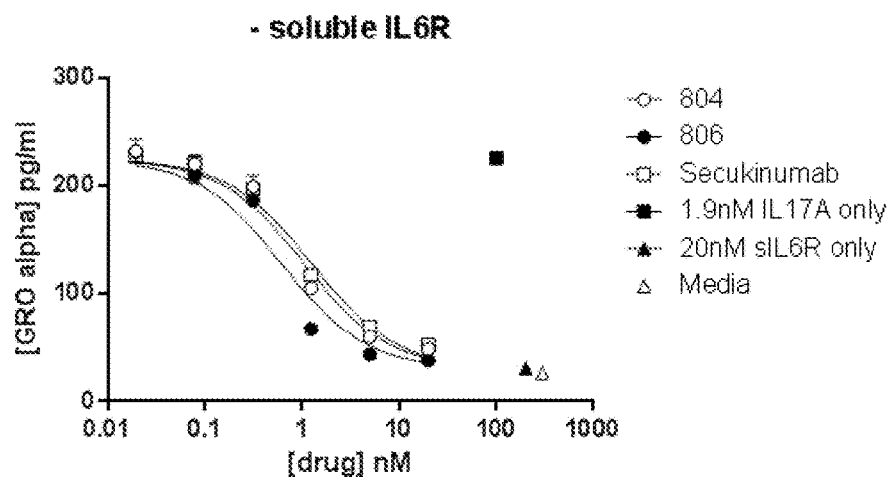
FIG. 17A-17B shows HT-29 IL-17A functional assay in the presence of soluble IL-6R.
Figure 17B:
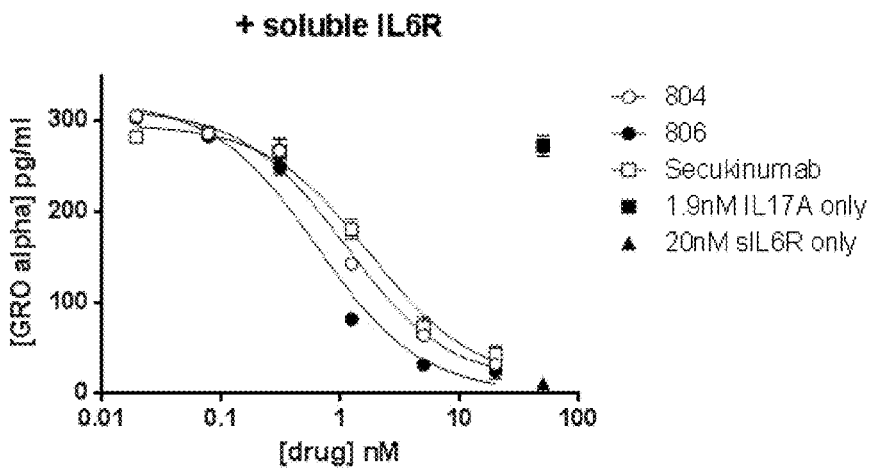

| FIG. 17A | 804 | 806 | Secukinumab |
|---|---|---|---|
| IC50 | 1.077 | 0.6264 | 1.283 |
| FIG. 17B | 804 | 806 | Secukinumab |
| IC50 | 1.112 | 0.6472 | 1.766 |

A similar study was performed to assess IL-6R blockade by the FynomAbs in the presence of IL-17A (see FIG. 18). The HEK-Blue IL-6R inhibition assay was performed exactly as described above, except that it was done in both the presence and in the absence of 20 nM recombinant human IL-17A. The 20 nM concentration was used because higher concentrations of IL-17A led to strong activation of the STAT3-inducible SEAP reporter gene, possibly through IL-17A induction of IL-6 in this cell line. Briefly, HEK Blue IL-6 cells were stimulated with IL-6 (15 pM) in the presence of various concentrations of FynomAbs COVA803 or COVA804. The inhibitors were pre-incubated with the cells in the presence or absence of 20 nM IL-17A for 30 minutes before addition of IL-6. COVA803 and COVA804 were used because these FynomAbs contain the same fynomer fused either to the heavy or light chain. COVA803 and COVA804 were compared with tocilizumab (produced in house) for their ability to block IL-6 signaling in the presence or absence of IL-17A.

As shown in FIG. 18 and Table 9, the ability of the FynomAbs and tocilizumab to block signaling through IL-6R was not affected by the presence of IL-17A. Similar IC50 values were obtained in both the presence and in the absence of IL-17A. These data suggest that binding of IL-17A by the fynomer portion of the FynomAb (attached at either the heavy or the light chain of the parental Ab) does not affect the ability of the FynomAbs to bind and inhibit IL-6R.

TABLE 9

Figure 18A:
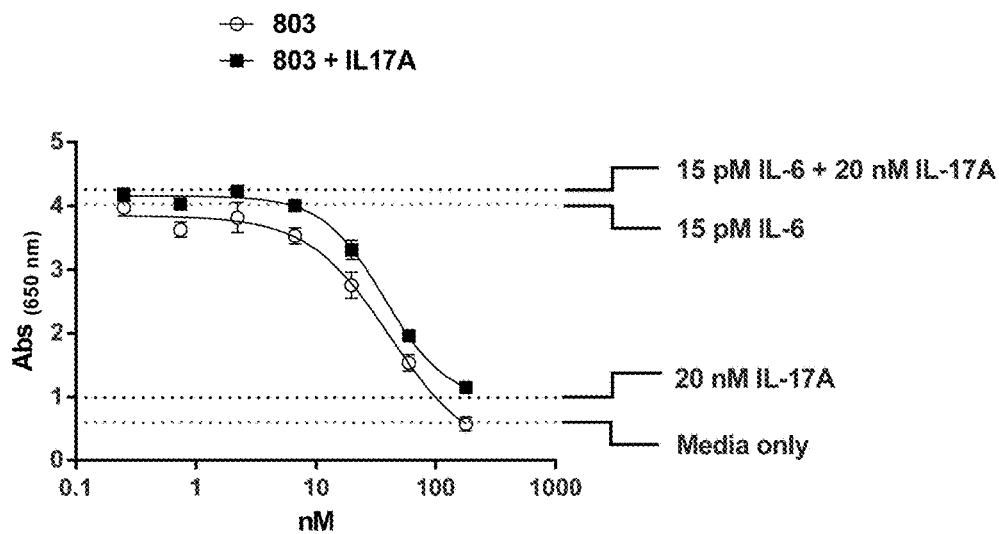
FIG. 18A-18C shows IL-6R inhibition in the presence of IL-17A.
Figure 18B:
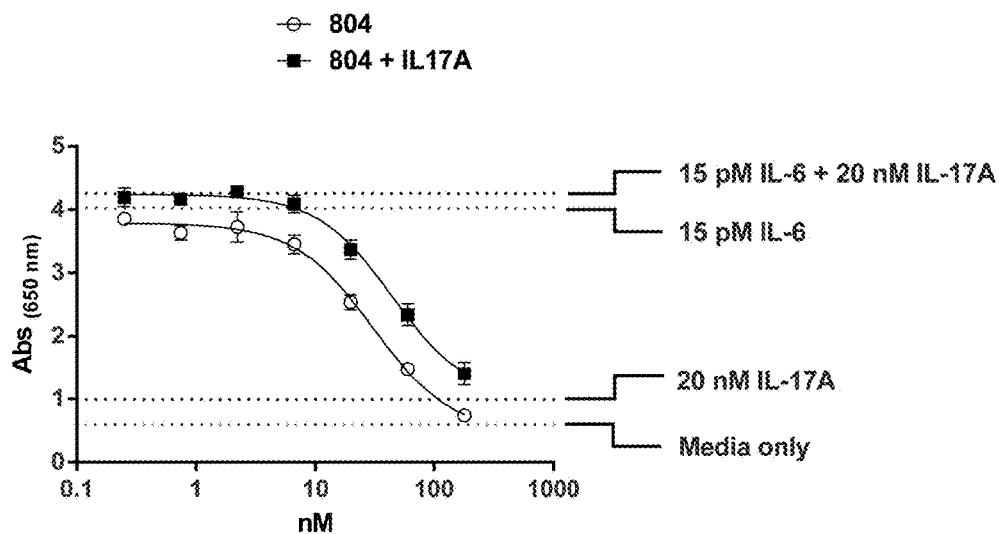
Figure 18C:
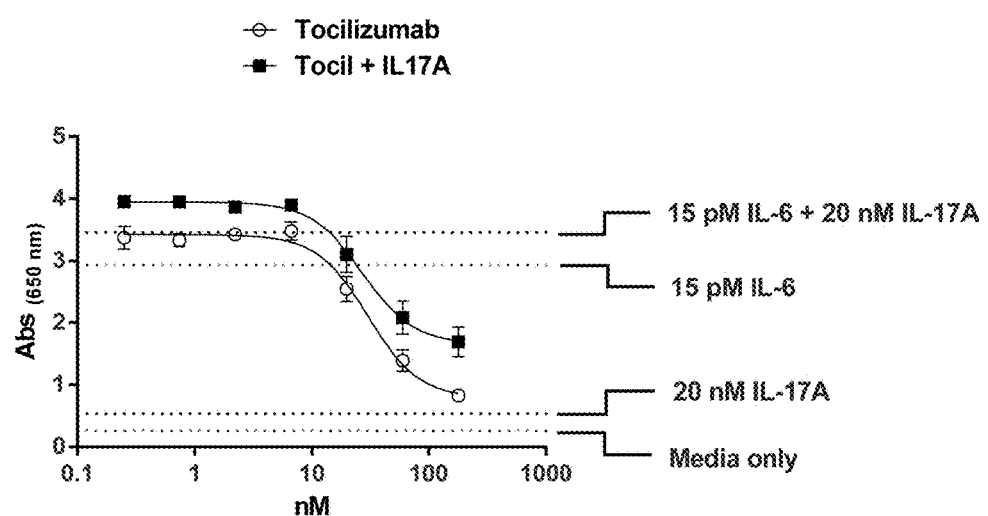
Figure 19A:
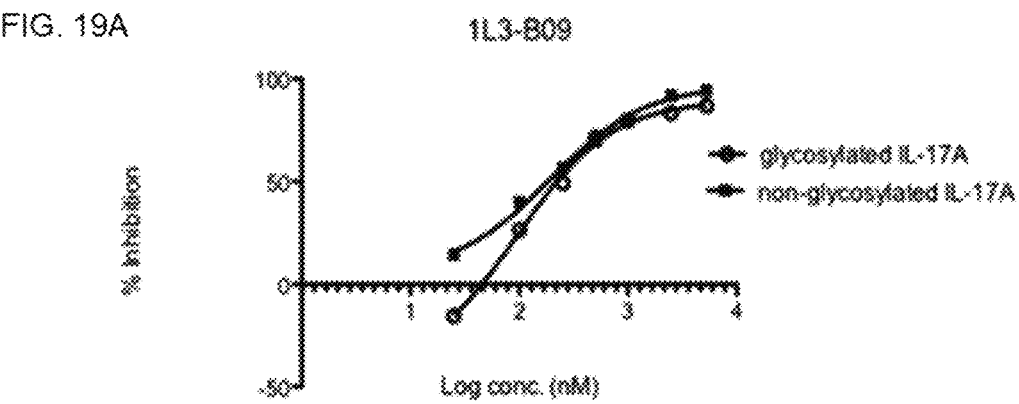
FIG. 19A-19F shows the dose-dependent in vitro inhibition of glycosylated and non-glycosylated IL-17A by the indicated fynomer polypeptides. A) 1L3-B09, (B) 11L0-C6, (C) 11L5-806, (D) 11L6-F03, (E) 11L9-009, (F) 11L10-A05.
Figure 19B:
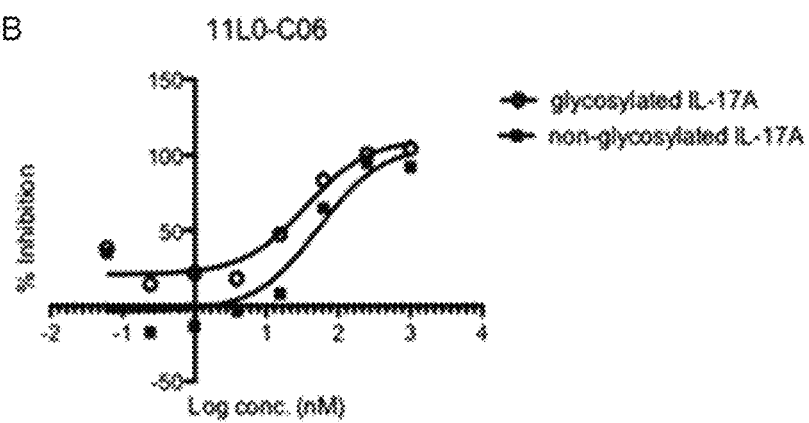
Figure 19C:
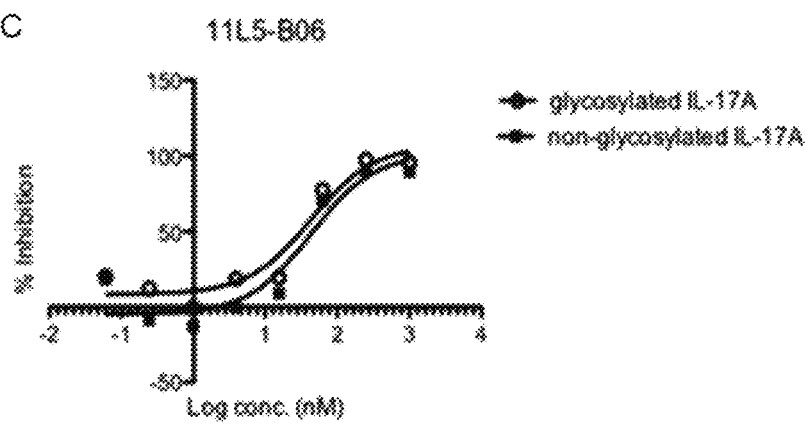
Figure 19D:
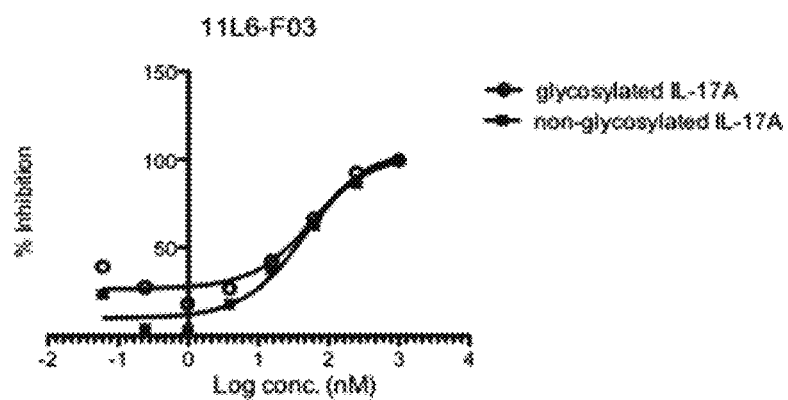
Figure 19E:
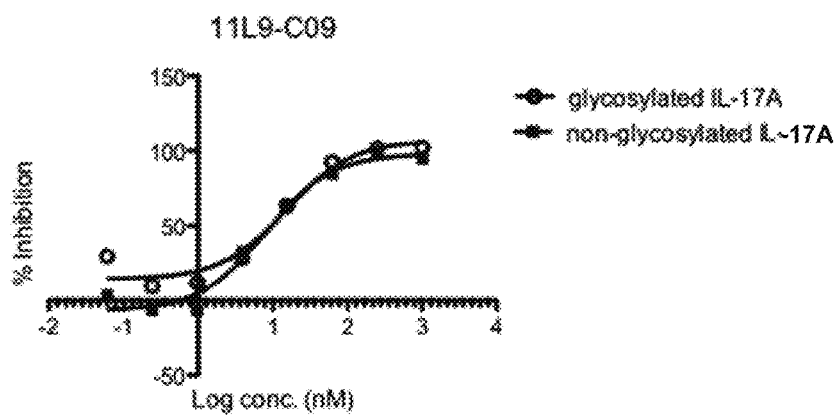
Figure 19F:
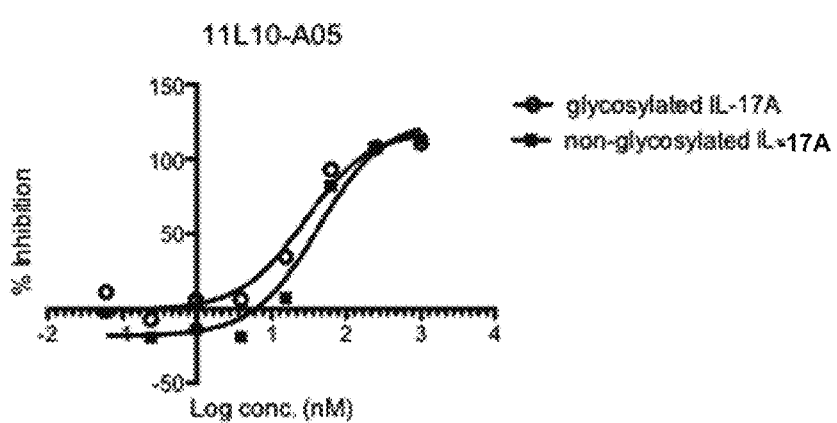

| FIG. 18A | 803 | 803 + IL-17A |
|---|---|---|
| IC50 | 41.73 | 37.67 |
| FIG. 18B | 804 | 804 + IL-17A |
| IC50 | 31.19 | 44.84 |
| FIG. 18C | Tocilizumab | Tocil + IL-17A |
| IC50 | 30.38 | 27.18 |

Example 11

Fynomer Polypeptides Bind to Glycosylated Human IL-17A with High Affinity

This example shows the expression yields of IL-17A-binding fynomer polypeptides and the characterization of these polypeptides by size exclusion chromatography and surface plasmon resonance studies.

Affinity Measurements

Affinity measurements were performed using a BIAcore T200 instrument (GE. Healthcare). For the interaction analysis between glycosylated IL-17A (produced in-house in HEK EBNA cells) and monomeric IL-17A-binding fynomer polypeptides, a Series S CM5 chip (GE Healthcare) was used with 2000 RU IL-17A immobilized using the Amine coupling kit (GE healthcare). The running buffer was PBS containing 0.05% Tween 20. The interactions were measured at a flow of 30 μl/min and injection of different concentrations of the IL-17A-binding fynomer polypeptides. All kinetic data of the interaction were evaluated using BIAcore T200 evaluation software.

Binding Properties

The binding properties were analyzed by real-time interaction analysis on a BIAcore chip revealing the following dissociation constants (KD) for selected IL-17A-binding fynomer polypeptides:

TABLE 10

Kinetics constants of the binding of fynomer IL-17A-binding polypeptides to recombinant human glycosylated IL-17A (produced in HEK EBNA cells).

| FYNOMER | SEQ ID NO. | $K_D$ (nM) |
|---|---|---|
| 1L3-B09 | 1 | 245 |
| 11L0-C06 | 2 | 7 |
| 11L5-B06 | 3 | 12 |
| 11L6-F03 | 4 | 11 |
| 11L9-C09 | 5 | 11 |

TABLE 10-continued

Kinetics constants of the binding of fynomer IL-
17A-binding polypeptides to recombinant human glycosylated
IL-17A (produced in HEK EBNA cells).

| FYNOMER | SEQ ID NO. | $K_D$ (nM) |
|---|---|---|
| 11L10-A05 | 6 | 7 |
| 11L11-A09 | 7 | 24 |

Data in Example 11 was disclosed in WO2014/044758 (PCT/EP2013/069481).

Example 12

Fynomer Polypeptides Inhibit Glycosylated IL-17A

Clone 1L3-B09 (SEQ ID NO:1) and five fynomer polypeptides with the highest binding affinity to IL-17A (11L0-006, 11L5-B06, 11L6-F03, 11L9-009, 11L10-A05, SEQ ID NOs:2-6) have been tested for their ability to inhibit IL-17A. The inhibitory activities of the indicated IL-17A-binding fynomer polypeptides were tested by stimulating human dermal fibroblasts with recombinant glycosylated IL-17A (produced in-house in HEK EBNA cells) and recombinant TNFα (Thermo Fisher Scientific) in the absence or presence of various concentrations of the IL-17A binding fynomer polypeptides. Cell culture supernatants were taken after 24 h of stimulation and IL-6 concentration in the supernatant was determined by ELISA. The results show that the IL-17A binding fynomer polypeptides were able to specifically inhibit glycosylated IL-17A.

Methods

For endotoxin removal, the protein solutions were filtered three times with the Acrodisc Mustang E membrane (VWR). After filtration the endotoxin levels of the protein solutions containing inhibitory IL-17A-binding fynomer polypeptides were less than 0.1 EU/ml, as determined by the Limulus amebocyte lysate (LAL) test (PYROGENT Single test Gel Clot LAL Assay (Lonza)). 100 µl of a cell suspension containing about 3900 Normal Human Dermal Fibroblasts (PromoCell, NHDF-c, C12300) were distributed per well (96 well plate, TPP or Corning) and cultured for 24 hours at 37° C. (medium: Fibroblast Growth Medium C-23010, PromoCell). The supernatant was aspirated and after mixing different concentrations of IL-17A-binding fynomer polypeptides with IL-17A and TNFα containing medium (final concentrations 1 ng/ml and 50 pg/ml respectively), 100 µl of the corresponding solution were added per well. As controls PBS was mixed with the IL-17A/TNFα containing medium (pos. control="no inhibitor") and medium with the single cytokines IL-17A or TNFα only (latter being the "TNFα control" well). As a negative control PBS was mixed with medium only. For comparison, the assay has also been performed using non-glycosylated IL-17A (R&D Systems) using the same conditions. After 24 hours incubation at 37° C. the supernatant was in an ELISA to determine the IL-6 concentration using an IL-6 ELISA kit following the manufacturer's instructions (IL-6 ELISA kit, R&D Systems). The percentages of inhibition were plotted and IC50 values were calculated using the software Prism 5. The percentage of IL-17A inhibition was determined with the following formula:

$$\text{inhibition (\%)} = \frac{(A450 - 650 \text{ nm (sample)} - A450 - 650 \text{ nm } (TNF\alpha \text{ control})) \times 100}{A450 - 650 \text{ nm (pos. control)} - A450 - 650 \text{ nm } (TNF\alpha \text{ control})}$$

Results

Normal Human Dermal Fibroblasts were incubated with IL-17A/TNFα and different concentrations of indicated IL-17A-binding fynomer polypeptides. It was observed that the fynomer polypeptides inhibited glycosylated IL-17A. The IC50 values are shown in Table 11.

TABLE 11

IC50 values for inhibition of glycosylated IL-17A obtained for IL-17A-binding fynomer polypeptides.

| FYNOMER | SEQ ID NO. | $IC_{50}$ value (nM) |
|---|---|---|
| 1L3-B09 | 1 | 300 |
| 11L0-C06 | 2 | 35 |
| 11L5-B06 | 3 | 43 |
| 11L6-F03 | 4 | 63 |
| 11L9-C09 | 5 | 32 |
| 11L10-A05 | 6 | 28 |

Dose-dependent inhibition curves of the indicated IL-17A-binding fynomer polypeptides inhibiting both glycosylated and non-glycosylated IL-17A are shown in FIG. 19.

It was found that the IL-17A-binding fynomer polypeptides are able to completely inhibit glycosylated IL-17A with similar potencies as compared to non-glycosylated IL-17A. This is an advantageous property as compared to the Fyn SH3-derived IL-17A-binding polypeptides previously described in WO2011/023685.

Figure 20A:
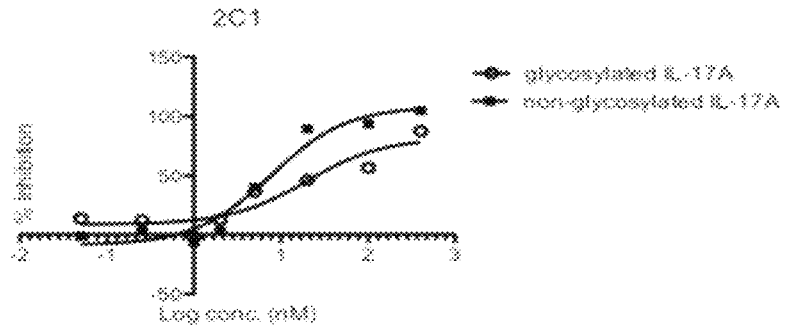
FIG. 20A-20C shows dose-dependent in vitro inhibition of glycosylated and non-glycosylated IL-17A by Fyn SH3 derived polypeptides described in WO2011/023685: (A) Fyn SH3 derived IL-17 binder 2C1 (SEQ ID NO: 30)(SEQ ID NO: 107 in WO2011/023685). (B) Fyn SH3 derived IL-17 binder A1_2 ("A1") (SEQ ID: 31) (SEQ ID NO: 53 in WO2011/023685). (C) Fyn SH3 derived IL-17 binder B1_2 ("B1") (SEQ ID: 32) (SEQ ID NO: 39 in WO2011/023685).
Figure 20B:
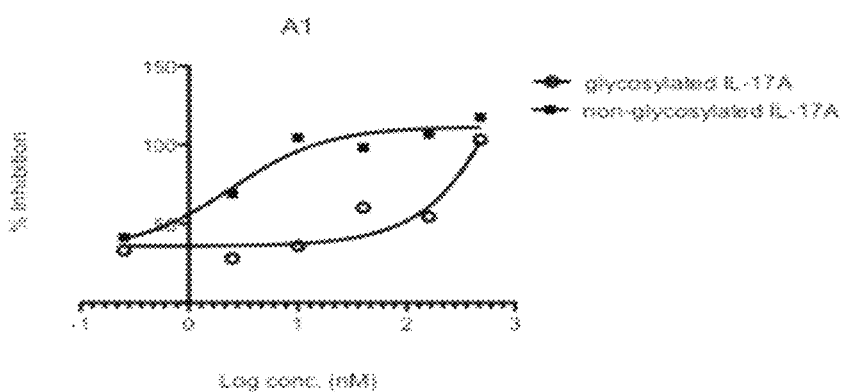
Figure 20C:
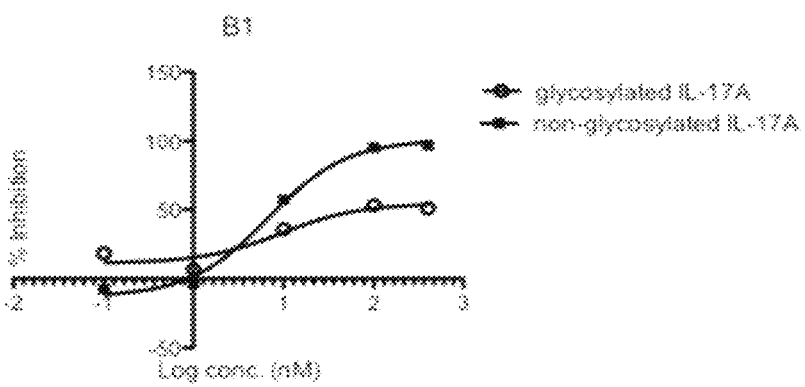

FIG. 20 shows three examples of Fyn SH3-derived IL-17A-binding polypeptides described in WO2011/023685.

Fyn SH3 derived IL-17 binder 2C1 (SEQ ID NO:107 in WO2011/023685), Fyn SH3 derived IL-17 binder A1_2 (SEQ ID NO:53 in WO2011/023685) and Fyn SH3 derived IL-17 binder B1_2 ("B1") (SEQ ID NO:39 in WO2011/023685) either do not inhibit glycosylated IL-17A completely even at high concentrations and/or show large differences in inhibition potency (IC50 values) between glycosylated and non-glycosylated IL-17A.

Example 13

Data in Example 13 was disclosed in WO2014/044758 (PCT/EP2013/069481).

Fynomer Polypeptide 11L11-A09 Inhibits Glycosylated IL-17A

Methods

Fynomer 11L11-A09 has been tested for its ability to inhibit IL-17A. The study conditions were the same as described above for the other fynomer polypeptides.

Results

Normal Human Dermal Fibroblasts were incubated with IL-17A/TNFα and different concentrations of the fynomer polypeptide 11L11-A09. It was observed that 11L11-A09 inhibited glycosylated IL-17A with an IC50 value of 66 nM (Table 12).

TABLE 12

IC50 value for inhibition of glycosylated IL-17A obtained for the IL-17A-binding fynomer polypeptide 11L11-A09.

| FYNOMER | SEQ ID NO. | $IC_{50}$ value (nM) |
|---|---|---|
| 11L11-A09 | 7 | 66 |

Figure 21:
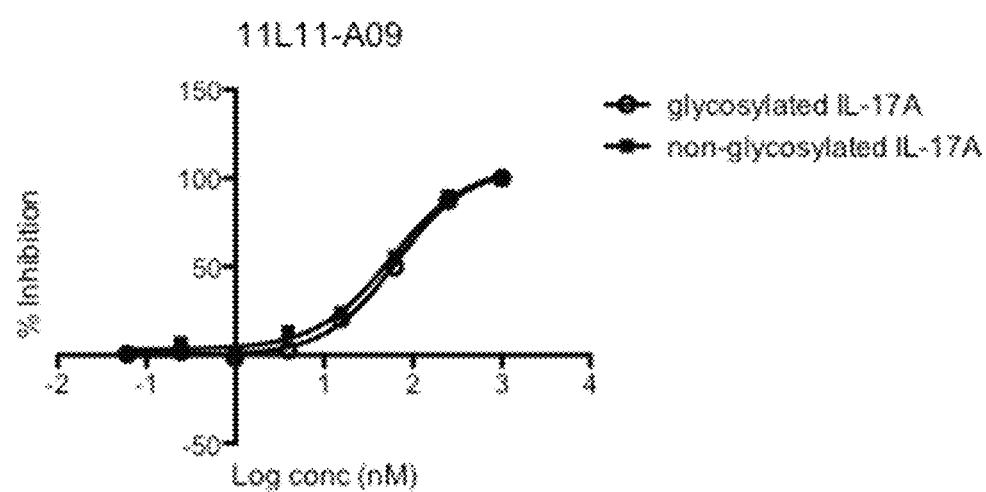
FIG. 21 shows the results of the dose-dependent in vitro inhibition of glycosylated and non-glycosylated IL-17A by fynomer polypeptide 11L11-A09.

FIG. 21 shows dose-dependent inhibition curves of fynomer polypeptide 11L11-A09. 11L11-A09 inhibited both glycosylated and non-glycosylated IL-17A with a comparable potency and efficacy.

Example 14

Pharmacokinetic Study in C57BL/6 Mice

In order to help rank the COVA801-808 FynomAbs, pharmacokinetic profile of all 8 FynomAbs was assessed in C57BL/6 mice.

Dosing and Blood Sampling

The determination of the pharmacokinetic properties of FynomAbs denoted COVA801 COVA802, COVA803, COVA804, COVA805, COVA806, COVA807, COVA808, and Tocilizumab were performed by measuring the concentrations by ELISA in mouse serum taken at different time points after a single retro-orbital injection. Six to 8 week old female C56BL/6 mice (Charles River, USA) were intravenously injected with 10 mg/kg dose based on individual weight. Each group consisted of 5 mice. Blood was withdrawn from the caudal vein (tail vein) 30 minutes, 6, 24, 48, 96, 144, 192, 240, and 288 hours after retro-orbital injection. Blood was collected in blood tube clotting activator microvettes (CB300, Sarstedt) and serum was prepared by centrifugation for 10 min at 10,000 rpm. The serum was stored at −20° C. until analysis.

IL-6R and IL-17A ELISA

The serum concentrations of tested FynomAbs and tocilizumab were determined by ELISA using immobilized human IL-17 alpha (Cell Signaling Technologies, 8928BF) and recombinant human IL-6R alpha (R&D Systems, Inc. 227-SR/CF) on high binding Nunc ELISA plates (Thermo Scientific, 456537), respectively. Both were coated at 5 mg/ml at 4° C. in PBS overnight. Plates were washed in PBS+0.05% Tween (PBST) and blocked for 2 hours with BSA (Fischer Scientific, 37525) diluted to 1% in PBST. For each mouse and time point, 800, 4,000 and 20,000-fold dilutions of serum were prepared in blocker diluent. The corresponding standard for each FynomAb was prepared making serial dilutions in blocker diluent starting at 4 nM with 2 fold titrations (4 nM-0.03125 nM). Fifty µl of standards (in duplicate) and serum dilutions (in triplicate) were added to plates and incubated for 1 hour at RT. The plates were washed 3 times with PBST and incubated with 50 µl of Peroxidase-AffiniPure Goat Anti-Human IgG (H+L) (Jackson ImmunoResearch, 109-035-003) diluted at 1:5,000 for 1 hour at RT. The plates were washed 3 times with PBST. 50 µl of TMB liquid substrate (Sigma-Aldrich Inc., T0440-1L) were added to all wells. Plates were incubated for 3 min and stopped with 50 µl stop solution. Absorbance values were recorded at 405 nM (PHERAstar Plus).

Data Analysis

Serum concentrations for each mouse were calculated using the standard curve and 4 parameter fit analysis (X value logarithmic, Y value linear). For every time-point and mouse, the average nM serum concentration of triplicates were multiplied by the corresponding dilution factor and then converted to ug/ml concentration. The STDEV and % CV was calculated for each time point and for the 3 dilution factors. One value with lowest % CV and best represented the linear portion of the standard curve was chosen as the value for each time point. These values were subjected to pharmacokinetic parameter analysis (Phoenix 64, WinNonlin 6.3). Half-life (h), area under the curve (AUC; h*ug/ml), volume of distribution (Vz; ml) and clearance (Cl; ml/h) were calculated using Non-compartmental PK analysis, Model Type: Plasma (200-202), Calculation Method: Linear Trapezoidal Linear Interpolation. Standard curves for each mouse were based on uniform weighting and best fit lambda Z calculation, required at least 3 data points in the regression, and did not include the Cmax.

Results

The serum concentrations and pharmacokinetic parameters of each FynomAb and tocilizumab are shown in Tables 13-21. Although both the IL-6R and IL-17A ELISAs were used to calculate the serum concentrations and PK parameters, only the IL-6R data is shown here. However, similar serum concentrations and PK parameters were determined from the IL-17A ELISA data. Thus the serum concentration versus time curves for the two different ELISA methods look very similar for each FynomAb (see FIGS. 22-25). This data indicates that the FynomAbs are stable in vivo, and their capacity to bind both IL-6R and IL-17A is retained. In general, the results from this pharmacokinetic study are in agreement with prior data in the same mouse strain.

Tables 13A and 13B: Serum Concentrations and PK Parameters of Tocilizumab.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A.

TABLE 13A

| Tocilizumab (IL-6R) | | | | | | | |
|---|---|---|---|---|---|---|---|
| | Concentration (ug/ml) | | | | | | |
| Time (hr) | Mouse 1 | Mouse 2 | Mouse 3 | Mouse 4 | Mouse 5 | Average (ug/ml) | STDEV |
| 0.5 | 319.00 | 299.66 | 270.66 | 261.00 | 309.33 | 291.93 | 25.02 |
| 6 | 435.00 | 222.33 | 251.33 | 328.66 | 270.66 | 301.60 | 84.10 |
| 24 | 232.00 | 232.00 | 222.33 | 261.00 | 174.00 | 224.27 | 31.62 |
| 48 | 251.33 | 183.67 | 164.33 | 232.00 | 145.00 | 195.27 | 45.03 |
| 96 | 174.00 | 133.40 | 116.00 | 174.00 | 87.00 | 136.88 | 37.72 |
| 144 | 143.07 | 116.00 | 106.33 | 222.33 | 106.33 | 138.81 | 49.05 |
| 192 | 116.00 | 87.00 | 104.40 | 145.00 | 75.40 | 105.56 | 27.02 |
| 240 | 58.00 | 63.80 | 58.00 | 87.00 | 50.27 | 63.41 | 14.03 |

TABLE 13B

| | | Pharmacokinetic Parameters | | | |
|---|---|---|---|---|---|
| Tocilizumab (IL-6R) | Mouse ID | Half Life (h) | Vz (ml) | Cl (ml/h) | AUC (h*ug/ml) |
| | 1 | 99.67 | 0.028 | 0.00020 | 42167.16 |
| | 2 | 111.30 | 0.037 | 0.00023 | 32673.59 |
| | 3 | 126.63 | 0.043 | 0.00024 | 31425.15 |
| | 4 | 70.92 | 0.018 | 0.00018 | 46549.51 |
| | 5 | 88.81 | 0.038 | 0.00030 | 27087.75 |
| Average | | 99.47 | 0.033 | 0.00023 | 35980.63 |
| STDEV | | 21.25 | 0.010 | 0.00005 | 8073.83 |

Tables 14A and 14B: Serum Concentrations and PK Parameters of COVA801.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 14A

COVA801 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 355.56 | 355.56 | 204.72 | 422.36 | 430.98 | 353.83 | 90.68 |
| 6 | 258.59 | 409.43 | 196.10 | 275.83 | 284.45 | 284.88 | 77.73 |
| 24 | 159.46 | 209.02 | 135.76 | 161.62 | 183.17 | 169.81 | 27.61 |
| 48 | 96.97 | 144.38 | 96.97 | 129.29 | 118.52 | 117.23 | 20.65 |
| 96 | 64.65 | 96.97 | 75.42 | 96.97 | 84.04 | 83.61 | 14.00 |
| 144 | 38.79 | 103.43 | 114.21 | 90.51 | 120.67 | 93.52 | 32.67 |
| 192 | 51.72 | 64.65 | 58.18 | 45.25 | 58.18 | 55.60 | 7.37 |
| 240 | 38.79 | 38.79 | 43.10 | 38.79 | 45.25 | 40.94 | 3.05 |

TABLE 14B

Pharmacokinetic Parameters

| COVA 801 (IL-6R) | Mouse ID | Half Life (h) | Vz (ml) | Cl (ml/h) | AUC (h*ug/ml) |
|---|---|---|---|---|---|
| | 1 | 94.41 | 0.055 | 0.00041 | 19322.94 |
| | 2 | 67.84 | 0.030 | 0.00030 | 29118.09 |
| | 3 | 68.28 | 0.037 | 0.00038 | 22189.49 |
| | 4 | 104.49 | 0.049 | 0.00033 | 24658.46 |
| | 5 | 67.84 | 0.032 | 0.00032 | 26453.49 |
| Average | | 80.57 | 0.041 | 0.00035 | 24348.49 |
| STDEV | | 17.60 | 0.011 | 0.00004 | 3781.32 |

Tables 15A and 15B: Serum Concentrations and PK Parameters of COVA802.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 15A

COVA802 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 193.94 | 258.59 | 340.47 | 297.38 | 269.36 | 271.95 | 53.88 |
| 6 | 131.45 | 247.81 | 226.26 | 258.59 | 193.94 | 211.61 | 51.16 |
| 24 | 129.29 | 161.62 | 129.29 | 161.62 | 122.83 | 140.93 | 19.07 |
| 48 | 96.97 | 140.07 | 88.35 | 129.29 | 120.67 | 115.07 | 21.80 |
| 96 | 64.65 | 88.35 | 62.49 | 109.90 | 84.04 | 81.89 | 19.39 |
| 144 | 45.25 | 77.58 | 56.03 | 99.13 | 25.86 | 60.77 | 28.44 |
| 192 | 30.17 | 53.87 | 43.10 | 64.65 | 30.60 | 44.48 | 14.95 |
| 240 | 16.81 | 45.25 | 32.32 | 23.27 | 20.26 | 27.58 | 11.44 |

TABLE 15B

Pharmacokinetic Parameters

| COVA 802 (IL-6R) | Mouse ID | Half Life (h) | Vz (ml) | Cl (ml/h) | AUC (h*ug/ml) |
|---|---|---|---|---|---|
| | 1 | 77.02 | 0.064 | 0.00058 | 15459.11 |
| | 2 | 116.06 | 0.053 | 0.00032 | 23760.41 |
| | 3 | 120.98 | 0.073 | 0.00042 | 18109.20 |
| | 4 | 45.92 | 0.024 | 0.00037 | 25673.85 |
| | 5 | 71.45 | 0.053 | 0.00052 | 17240.67 |
| Average | | 86.28 | 0.054 | 0.00044 | 20048.64 |
| STDEV | | 31.72 | 0.018 | 0.00011 | 4419.56 |

Tables 16A and 16B: Serum Concentrations and PK Parameters of COVA803.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 16A

COVA803 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 355.21 | 430.56 | 441.32 | 402.57 | 376.74 | 401.28 | 36.01 |
| 6 | 236.81 | 236.81 | 230.35 | 236.81 | 245.42 | 237.24 | 5.36 |
| 24 | 129.17 | 129.17 | 135.63 | 122.71 | 157.15 | 134.76 | 13.32 |
| 48 | 90.42 | 81.81 | 127.01 | 129.17 | 114.10 | 108.50 | 21.45 |
| 96 | 71.04 | 64.58 | 83.96 | 81.81 | 79.65 | 76.21 | 8.14 |
| 144 | 64.58 | 58.13 | 73.19 | 68.89 | 73.19 | 67.60 | 6.39 |
| 192 | 47.36 | 31.43 | 49.51 | 49.51 | 45.21 | 44.61 | 7.58 |
| 240 | 38.75 | 25.83 | 30.14 | 36.60 | 38.75 | 34.01 | 5.78 |

TABLE 16B

Pharmacokinetic Parameters

| COVA803 (IL-6R) | Mouse ID | Half Life (h) | Vz (ml) | Cl (ml/h) | AUC (h*ug/ml) |
|---|---|---|---|---|---|
| | 1 | 158.43 | 0.081 | 0.00035 | 19528.98 |
| | 2 | 99.28 | 0.067 | 0.00047 | 17750.35 |
| | 3 | 74.99 | 0.043 | 0.00039 | 22094.56 |
| | 4 | 105.20 | 0.056 | 0.00037 | 21705.44 |
| | 5 | 110.88 | 0.057 | 0.00036 | 21858.29 |
| Average | | 109.76 | 0.061 | 0.00039 | 20587.53 |
| STDEV | | 30.45 | 0.014 | 0.00005 | 1891.15 |

Tables 17A and 17B: Serum Concentrations and PK Parameters of COVA804.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 17A

COVA804 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 441.32 | 419.79 | 387.50 | 376.74 | 398.27 | 404.72 | 25.92 |
| 6 | 419.79 | 312.15 | 292.78 | 262.64 | 226.04 | 302.68 | 73.11 |
| 24 | 215.28 | 202.36 | 167.92 | 144.24 | 161.46 | 178.25 | 29.57 |
| 48 | 178.68 | 176.53 | 142.08 | 129.17 | 129.17 | 151.13 | 24.75 |
| 96 | 129.17 | 142.08 | 129.17 | 92.57 | 122.71 | 123.14 | 18.48 |
| 144 | 96.88 | 124.86 | 131.32 | 103.33 | 116.25 | 114.53 | 14.39 |
| 192 | 66.74 | 101.18 | 94.72 | 96.88 | 73.19 | 86.54 | 15.48 |
| 240 | 24.54 | 75.35 | 75.35 | 53.82 | 64.58 | 58.73 | 21.09 |

TABLE 17B

| | | Pharmacokinetic Parameters | | | |
|---|---|---|---|---|---|
| COVA 804 (IL-6R) | Mouse ID | Half Life (h) | Vz (ml) | Cl (ml/h) | AUC (h*ug/ml) |
| | 1 | 69.55 | 0.029 | 0.00029 | 31852.27 |
| | 2 | 160.73 | 0.044 | 0.00019 | 35010.19 |
| | 3 | 119.78 | 0.038 | 0.00022 | 32102.31 |
| | 4 | 190.81 | 0.065 | 0.00024 | 27240.23 |
| | 5 | 171.03 | 0.056 | 0.00023 | 28424.82 |
| Average | | 142.38 | 0.047 | 0.00023 | 30925.96 |
| STDEV | | 48.26 | 0.014 | 0.00004 | 3113.00 |

Tables 18A and 18B: Serum Concentrations and PK Parameters of COVA805.

(A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 18A

COVA805 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 336.10 | 323.17 | 463.21 | 264.78 | 290.85 | 335.62 | 76.58 |
| 6 | 185.28 | 165.89 | 193.90 | 172.36 | 159.43 | 175.37 | 14.09 |
| 24 | 99.11 | 86.18 | 96.95 | 95.87 | 92.64 | 94.15 | 5.03 |
| 48 | 84.02 | 73.25 | 66.79 | 58.82 | 73.25 | 71.23 | 9.30 |
| 96 | 64.63 | 45.24 | 48.69 | 43.95 | 58.17 | 52.14 | 8.93 |
| 144 | 51.71 | 40.50 | 0.00 | 43.74 | 45.24 | 36.24 | 20.66 |
| 192 | 25.42 | 32.32 | 32.32 | 32.32 | 32.32 | 30.94 | 3.08 |
| 240 | 19.82 | 25.85 | 26.28 | 19.35 | 23.70 | 23.00 | 3.27 |

TABLE 18B

| | | Pharmacokinetic Parameters | | | |
|---|---|---|---|---|---|
| COVA 805 (IL-6R) | Mouse ID | Half Life (h) | Vz (ml) | Cl (ml/h) | AUC (h*ug/ml) |
| | 1 | 90.72 | 0.072 | 0.00055 | 15571.82 |
| | 2 | 148.22 | 0.111 | 0.00052 | 13653.16 |
| | 3 | 161.96 | 0.113 | 0.00048 | 14571.72 |

TABLE 18B-continued

| | | Pharmacokinetic Parameters | | | |
|---|---|---|---|---|---|
| COVA 805 (IL-6R) | Mouse ID | Half Life (h) | Vz (ml) | Cl (ml/h) | AUC (h*ug/ml) |
| | 4 | 81.58 | 0.076 | 0.00065 | 13174.81 |
| | 5 | 102.91 | 0.083 | 0.00056 | 14412.29 |
| Average | | 117.08 | 0.091 | 0.00055 | 14276.76 |
| STDEV | | 35.84 | 0.020 | 0.00006 | 920.02 |

Tables 19A and 19B: Serum Concentrations and PK Parameters of COVA806.

(A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 19A

COVA806 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 258.54 | 321.02 | 312.40 | 355.49 | 333.94 | 316.28 | 36.13 |
| 6 | 183.13 | 215.45 | 185.28 | 226.22 | 226.22 | 207.26 | 21.51 |
| 24 | 96.95 | 129.27 | 129.27 | 109.88 | 124.96 | 118.06 | 14.24 |
| 48 | 68.94 | 105.57 | 105.57 | 88.33 | 94.80 | 92.64 | 15.16 |
| 96 | 62.48 | 79.72 | 77.56 | 66.79 | 86.18 | 74.54 | 9.71 |
| 144 | 51.71 | 71.10 | 68.94 | 73.25 | 58.17 | 64.63 | 9.27 |
| 192 | 43.09 | 51.71 | 58.17 | 51.71 | 40.93 | 49.12 | 7.05 |
| 240 | 38.78 | 38.78 | 38.78 | 45.24 | 21.54 | 36.63 | 8.88 |

TABLE 19B

| | | Pharmacokinetic Parameters | | | |
|---|---|---|---|---|---|
| COVA 806 (IL-6R) | Mouse ID | Half Life (h) | Vz (ml) | Cl (ml/h) | AUC (h*ug/ml) |
| | 1 | 218.56 | 0.112 | 0.00036 | 15925.26 |
| | 2 | 109.78 | 0.059 | 0.00037 | 20661.31 |
| | 3 | 137.35 | 0.071 | 0.00036 | 20384.46 |
| | 4 | 184.33 | 0.084 | 0.00032 | 19501.67 |
| | 5 | 73.77 | 0.050 | 0.00047 | 19107.40 |
| Average | | 144.76 | 0.075 | 0.00037 | 19116.02 |
| STDEV | | 57.73 | 0.024 | 0.00006 | 1892.53 |

Tables 20A and 20B: Serum Concentrations and PK Parameters of COVA807.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 20A

COVA807 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 505.82 | 404.66 | 441.25 | 368.07 | 374.52 | 418.86 | 56.59 |
| 6 | 320.71 | 355.15 | 245.38 | 226.01 | 192.43 | 267.94 | 67.75 |
| 24 | 222.78 | 234.62 | 154.98 | 129.15 | 127.21 | 173.74 | 51.52 |
| 48 | 204.48 | 139.91 | 137.76 | 187.26 | 106.76 | 155.23 | 39.82 |
| 96 | 161.43 | 161.43 | 120.54 | 94.71 | 92.34 | 126.09 | 34.11 |
| 144 | 129.15 | 152.82 | 109.77 | 109.77 | 70.17 | 114.34 | 30.38 |
| 192 | 71.03 | 103.32 | 75.34 | 79.64 | 72.32 | 80.33 | 13.27 |
| 240 | 66.73 | 55.96 | 71.03 | 64.57 | 53.17 | 62.29 | 7.49 |

TABLE 20B

| COVA 807 (IL-6R) | Mouse ID | Pharmacokinetic Parameters | | | |
|---|---|---|---|---|---|
| | | Half Life (h) | Vz (ml) | Cl (ml/h) | AUC (h*ug/ml) |
| | 1 | 106.59 | 0.033 | 0.00021 | 36284.17 |
| | 2 | 66.24 | 0.023 | 0.00024 | 36737.27 |
| | 3 | 186.18 | 0.056 | 0.00021 | 28796.38 |
| | 4 | 125.40 | 0.045 | 0.00025 | 28400.87 |
| | 5 | 187.97 | 0.074 | 0.00027 | 22447.23 |
| Average | | 134.48 | 0.046 | 0.00024 | 30533.18 |
| STDEV | | 52.56 | 0.020 | 0.00003 | 6010.62 |

Tables 21A and 21B: Serum Concentrations and PK Parameters of COVA808.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 21A

COVA808 (IL-6R)

Concentration (ug/ml)

| Time (hr) | Mouse 1 | Mouse 2 | Mouse 3 | Mouse 4 | Mouse 5 | Average (ug/ml) | STDEV |
|---|---|---|---|---|---|---|---|
| 0.5 | 226.01 | 256.14 | 290.58 | 408.96 | 279.82 | 292.30 | 69.77 |
| 6 | 172.20 | 191.57 | 163.59 | 288.43 | 204.48 | 204.05 | 49.82 |
| 24 | 129.15 | 161.43 | 96.86 | 129.15 | 126.99 | 128.72 | 22.85 |
| 48 | 90.40 | 124.84 | 77.49 | 126.99 | 161.43 | 116.23 | 33.17 |
| 96 | 77.49 | 90.40 | 66.73 | 96.86 | 109.77 | 88.25 | 16.74 |
| 144 | 77.49 | 96.86 | 64.57 | 105.47 | 96.86 | 88.25 | 16.74 |
| 192 | 51.66 | 58.12 | 49.51 | 73.18 | 75.34 | 61.56 | 12.04 |
| 240 | 45.20 | 21.09 | 40.90 | 66.73 | 27.98 | 40.38 | 17.63 |

TABLE 21B

| COVA 808 (IL-6R) | Mouse ID | Pharmacokinetic Parameters | | | |
|---|---|---|---|---|---|
| | | Half Life (h) | Vz (ml) | Cl (ml/h) | AUC (h*ug/ml) |
| | 1 | 158.86 | 0.076 | 0.00033 | 19671.12 |
| | 2 | 43.65 | 0.026 | 0.00041 | 23188.10 |
| | 3 | 145.68 | 0.081 | 0.00039 | 17277.61 |

TABLE 21B-continued

| COVA 808 (IL-6R) | Mouse ID | Pharmacokinetic Parameters | | | |
|---|---|---|---|---|---|
| | | Half Life (h) | Vz (ml) | Cl (ml/h) | AUC (h*ug/ml) |
| | 4 | 220.91 | 0.066 | 0.00021 | 26725.74 |
| | 5 | 85.72 | 0.042 | 0.00034 | 25926.65 |
| Average | | 130.96 | 0.058 | 0.00034 | 22557.84 |
| STDEV | | 68.48 | 0.024 | 0.00008 | 4041.39 |

Figure 22:
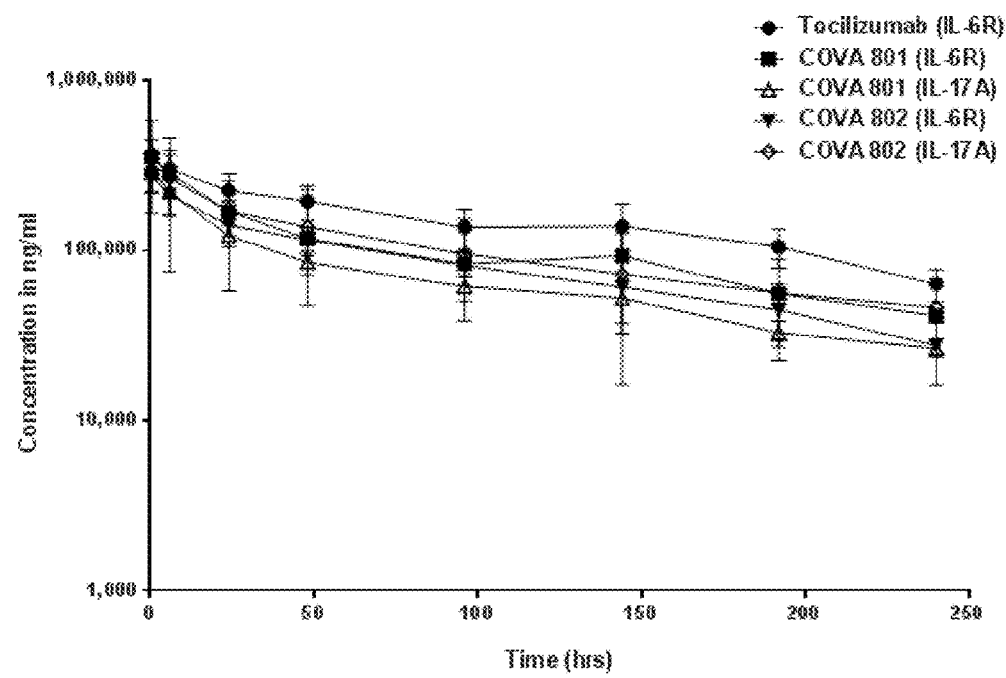
FIG. 22 shows mean serum concentrations plotted versus time for FynomAbs denoted COVA801 and COVA802.

FIG. 22 shows mean serum concentrations plotted versus time for COVA801 and COVA802.

The mean serum concentrations+/− standard deviation (STDEV) as determined by either IL6R or IL-17A ELISAs are shown for COVA801 and COVA802 with tocilizumab (IL-6R ELISA) as a comparator.

Figure 23:
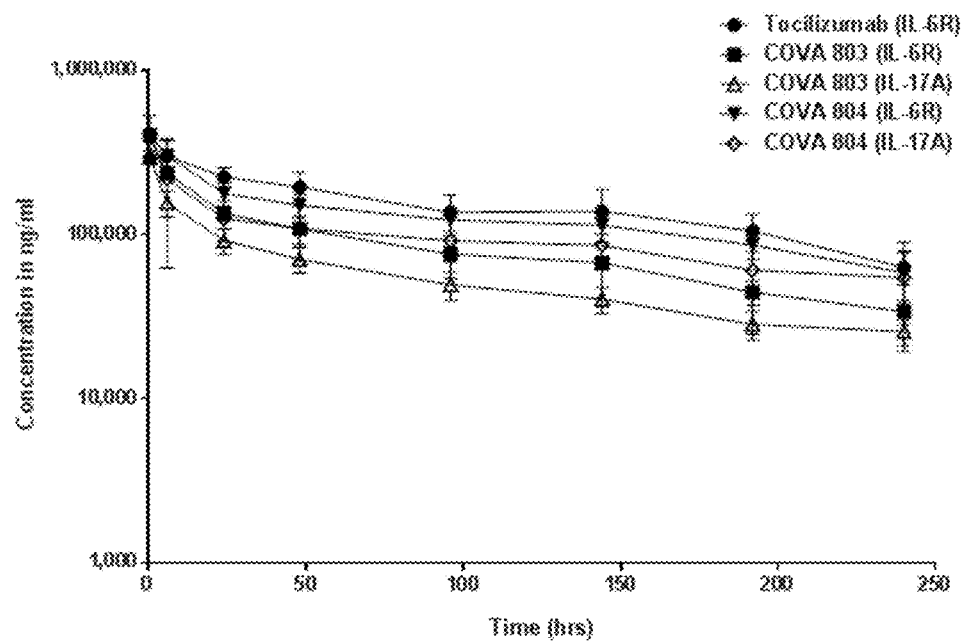
FIG. 23 shows mean serum concentrations plotted versus time for FynomAbs denoted COVA803 and COVA804.

FIG. 23 shows mean serum concentrations plotted versus time for COVA803 and COVA804.

The mean serum concentrations+/− standard deviation (STDEV) as determined by either IL6R or IL-17A ELISAs are shown for COVA803 and COVA804 with tocilizumab (IL-6R ELISA) as a comparator.

Figure 24:
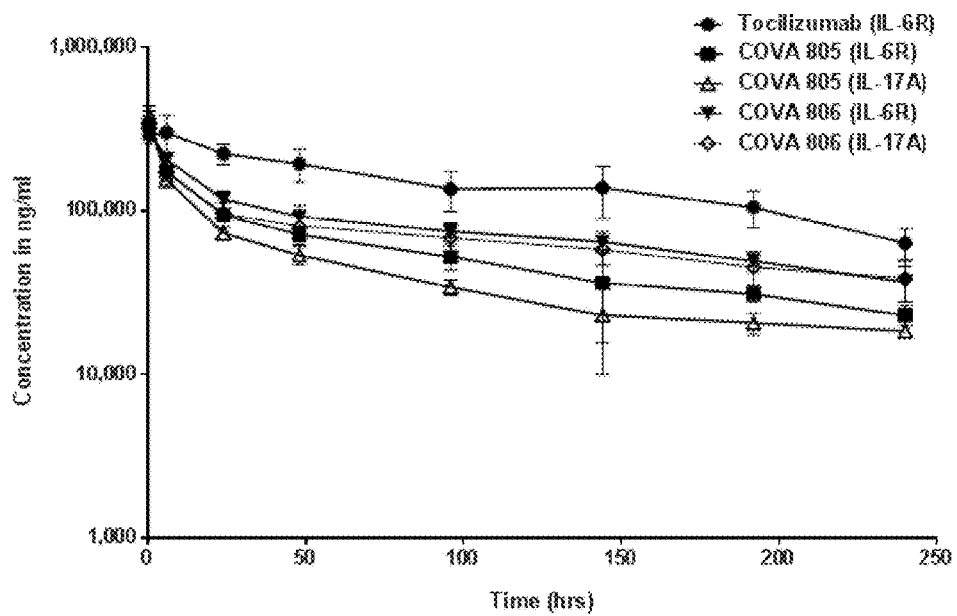
FIG. 24 shows mean serum concentrations plotted versus time for FynomAbs denoted COVA805 and COVA806.

FIG. 24 shows mean serum concentrations plotted versus time for COVA805 and COVA806.

The mean serum concentrations+/− standard deviation (STDEV) as determined by either IL6R or IL-17A ELISAs are shown for COVA805 and COVA806 with tocilizumab (IL-6R ELISA) as a comparator.

Figure 25:
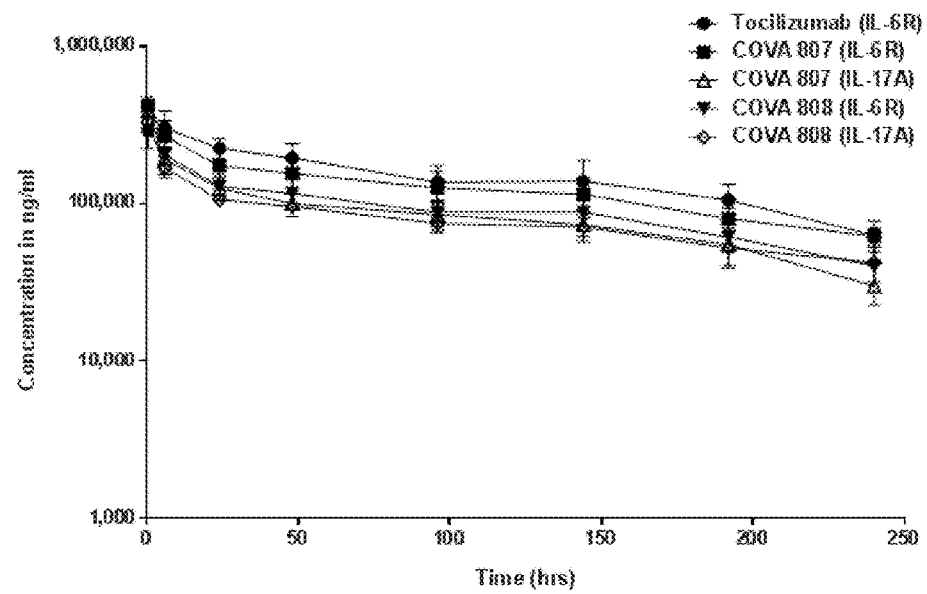
FIG. 25 shows mean serum concentrations plotted versus time for FynomAbs denoted COVA807 and COVA808.

FIG. 25 shows mean serum concentrations plotted versus time for COVA807 and COVA808.

The mean serum concentrations+/− standard deviation (STDEV) as determined by either IL6R or IL-17A ELISAs are shown for COVA807 and COVA808 with tocilizumab (IL-6R ELISA) as a comparator.

Example 15

Pharmacokinetic Study in Cynomolgus Monkeys
Dosing, Blood Sampling

The determination of the pharmacokinetic properties of FynomAbs denoted as COVA801, COVA802, COVA803, COVA804, COVA806, COVA808, and Tocilizumab were performed by measuring the concentrations by ELISA in cynomolgus monkey serum taken at different time points after a single i.v. injection. Male and female monkeys were intravenously injected with 5 mg/kg dose based on individual weight. Each group consisted of 4 monkeys. Blood was withdrawn at 5 min, 30 min, 2 hr, 6 hr, 24 hr, day 3, day 4, day 5, day 7, day 10, day 13, day 17, day 22, and day 27 after i.v. injection. Blood was collected in tubes without any anti-coagulants and serum was prepared by centrifugation for 1-2 min at 10,000 rpm. The serum was stored at −80° C. until analysis.

IL-6R and IL-17A ELISA

The serum concentration of tested FynomAbs and Tocilizumab were determined by ELISA according to the same protocol outlined above for the mouse PK study.

Data Analysis

Serum concentrations for each monkey were calculated using the standard curve and 4 parameter fit analysis (X value logarithmic, Y value linear). For every time-point and monkey, the average nM serum concentration of duplicate was multiplied by the corresponding dilution factor and then converted to ug/ml STDEV and % CV were calculated for each time point and for the 3 dilution factors. One value with lowest % CV that best represented the linear portion of the standard curve was chosen as the value for each time point. These values were subjected to pharmacokinetic parameter analysis (Phoenix 64, WinNonlin 6.3). Half-life (h), area under the curve (AUC; h*ug/ml), volume of distribution (Vz; ml) and clearance (Cl; ml/h) were calculated using Non-compartmental PK analysis, Model Type: Plasma (200-202), Calculation Method: Linear Trapezoidal Linear Interpolation. Standard curves for each monkey were based on uniform weighting and best fit lambda Z calculation, required at least 3 data points in the regression, and did not include the Cmax.

Results

The serum concentrations and pharmacokinetic parameters of each FynomAb and tocilizumab are shown in Tables 22-28. Although both the IL-6R and IL-17A ELISAs were used to calculate the serum concentrations and PK parameters, only the IL-6R data is shown here. However, similar serum concentrations and PK parameters were determined from the IL-17A ELISA data. Thus the serum concentration versus time curves for the two different ELISA methods look very similar for each FynomAb (see FIGS. 26-29). This again suggests that the FynomAbs are stable in vivo, and their capacity to bind both IL-6R and IL-17A is retained.

In general, all of the FynomAbs showed favorable PK profiles as none of the FynomAbs were cleared rapidly from circulation. COVA804 appeared to have the most favorable PK profile with the best AUC that was very similar to tocilizumab.

Tables 22A-22B: Serum Concentrations and PK Parameters of Tocilizumab in Cynomolgus Monkeys.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A.

TABLE 22A

Tocilizumab (IL-6R)

| Time (hr) | Monkey 1 | Monkey 2 | Monkey 3 | Monkey 4 | Average (ug/ml) | STDEV |
|---|---|---|---|---|---|---|
| 0.083 | 141.52 | 168.20 | 121.51 | 129.05 | 140.07 | 20.49 |
| 0.5 | 139.20 | 131.37 | 91.35 | 116.29 | 119.55 | 21.07 |
| 6 | 95.70 | 118.90 | 88.45 | 109.04 | 103.02 | 13.59 |
| 24 | 76.85 | 88.45 | 76.85 | 100.05 | 85.55 | 11.11 |
| 72 | 62.35 | 65.83 | 46.40 | 92.80 | 66.84 | 19.26 |
| 120 | 40.60 | 40.89 | 37.70 | 69.60 | 47.20 | 15.00 |
| 168 | 27.84 | 33.06 | 25.81 | 63.80 | 37.63 | 17.71 |
| 240 | 22.62 | 22.91 | 21.17 | 32.19 | 24.72 | 5.04 |
| 312 | 11.54 | 14.67 | 7.02 | 21.46 | 13.67 | 6.07 |
| 408 | 5.10 | 3.31 |  | 8.64 | 5.68 | 2.71 |
| 528 |  |  |  | 2.44 | 2.44 |  |

TABLE 22B

| Tocilizumab (IL-6R) | Monkey ID | Half Life (h) | Vz (ml) | Cl (ml/h) | AUC (h*ug/ml) |
|---|---|---|---|---|---|
|  | 1 | 68.09 | 0.035 | 0.00036 | 13880.12 |
|  | 2 | 86.91 | 0.041 | 0.00033 | 14893.51 |
|  | 3 | 92.55 | 0.055 | 0.00041 | 11238.18 |
|  | 4 | 68.68 | 0.022 | 0.00023 | 21782.04 |
| Average |  | 79.05 | 0.038 | 0.00033 | 15448.47 |
| STDEV |  | 12.54 | 0.013 | 0.00008 | 4494.75 |

Tables 23A-23B: Serum Concentrations and PK Parameters of COVA801 in Cynomolgus Monkeys.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 23A

COVA801 (IL-6R)

Concentration (ug/ml)

| Time (hr) | Monkey 1 | Monkey 2 | Monkey 3 | Monkey 4 | Average (ug/ml) | STDEV |
|---|---|---|---|---|---|---|
| 0.083 | 177.78 | 119.60 | 161.62 | 174.55 | 158.38 | 26.78 |
| 0.5 | 189.09 | 112.16 | 132.53 | 126.06 | 139.96 | 33.84 |
| 6 | 136.08 | 84.04 | 109.90 | 106.67 | 109.17 | 21.31 |
| 24 | 83.72 | 66.59 | 74.34 | 67.88 | 73.13 | 7.83 |
| 72 | 48.81 | 52.04 | 58.18 | 58.18 | 54.30 | 4.67 |
| 120 | 36.53 | 27.54 | 32.32 | 38.79 | 33.79 | 4.96 |
| 168 | 21.66 | 19.59 | 25.86 | 19.39 | 21.62 | 3.00 |
| 240 | 10.67 | 9.37 | 12.93 | 8.40 | 10.34 | 1.96 |
| 312 | 4.27 | 2.91 | 0.16 |  |  |  |
| 408 |  |  |  |  |  |  |
| 528 |  |  |  |  |  |  |

TABLE 23B

| COVA 801 (IL-6R) | Monkey ID | Half Life (h) | Vz (ml) | Cl (ml/h) | AUC (h*ug/ml) |
|---|---|---|---|---|---|
|  | 1 | 62.71 | 0.039 | 0.00043 | 11282.55 |
|  | 2 | 64.86 | 0.049 | 0.00052 | 9321.33 |
|  | 3 | 84.64 | 0.050 | 0.00041 | 10538.40 |
|  | 4 | 54.77 | 0.037 | 0.00047 | 10030.71 |
| Average |  | 66.74 | 0.044 | 0.00046 | 10293.25 |
| STDEV |  | 12.70 | 0.007 | 0.00005 | 827.12 |

Tables 24A-24B: Serum Concentrations and PK Parameters of COVA802 in Cynomolgus Monkeys.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 24A

COVA802 (IL-6R)

| Time (hr) | Monkey 1 | Monkey 2 | Monkey 3 | Monkey 4 | Average (ug/ml) | STDEV |
|---|---|---|---|---|---|---|
| 0.083 | 131.88 | 118.63 | 103.43 | 129.29 | 120.81 | 12.93 |
| 0.5 | 110.22 | 115.07 | 96.97 | 109.90 | 108.04 | 7.75 |
| 6 | 91.48 | 74.34 | 54.95 | 96.97 | 79.43 | 18.96 |
| 24 | 56.57 | 53.98 | 51.72 | 77.58 | 59.96 | 11.91 |
| 72 | 40.73 | 43.31 | 42.02 | 51.72 | 44.44 | 4.96 |
| 120 | 22.30 | 21.92 | 32.32 | 38.79 | 28.83 | 8.20 |
| 168 | 11.64 | 15.84 | 19.39 | 21.98 | 17.21 | 4.49 |
| 240 | 6.53 | 10.54 | 12.93 | 14.87 | 11.22 | 3.59 |
| 312 |  | 2.72 |  | 5.82 |  |  |
| 408 |  |  |  |  |  |  |
| 528 |  |  |  |  |  |  |

TABLE 24B

| COVA 802 (IL-6R) | Monkey ID | Pharmacokinetic Parameters Half Life (h) | Vz (ml) | Cl (ml/h) | AUC (h*ug/ml) |
|---|---|---|---|---|---|
|  | 1 | 66.00 | 0.060 | 0.00063 | 7259.29 |
|  | 2 | 70.05 | 0.061 | 0.00061 | 7962.71 |
|  | 3 | 103.17 | 0.076 | 0.00051 | 7862.69 |
|  | 4 | 78.34 | 0.048 | 0.00043 | 10999.95 |
| Average |  | 79.39 | 0.062 | 0.00055 | 8521.16 |
| STDEV |  | 16.66 | 0.011 | 0.00009 | 1681.48 |

Tables 25A-25B: Serum Concentrations and PK Parameters of COVA803 in Cynomolgus Monkeys.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 25A

COVA803 (IL-6R)

| Time (hr) | Monkey 1 | Monkey 2 | Monkey 3 | Monkey 4 | Average (ug/ml) | STDEV |
|---|---|---|---|---|---|---|
| 0.083 | 125.94 | 129.29 | 129.29 | 142.22 | 131.69 | 7.20 |
| 0.5 | 132.40 | 117.98 | 106.67 | 135.76 | 123.20 | 13.45 |
| 6 | 119.48 | 83.07 | 67.88 | 119.60 | 97.51 | 26.18 |
| 24 | 83.96 | 59.48 | 58.18 | 84.04 | 71.41 | 14.54 |
| 72 | 54.90 | 44.61 | 45.25 | 54.95 | 49.93 | 5.78 |
| 120 | 32.29 | 25.86 | 32.32 | 38.79 | 32.32 | 5.28 |
| 168 | 9.69 | 19.07 | 20.04 | 25.86 | 18.66 | 6.69 |
| 240 |  | 10.86 | 11.64 | 12.93 | 11.81 | 1.05 |
| 312 |  | 2.91 | 3.23 | 6.46 |  |  |
| 408 |  |  |  |  |  |  |
| 528 |  |  |  |  |  |  |

TABLE 25B

| COVA 803 (IL-6R) | Monkey ID | Pharmacokinetic Parameters Half Life (h) | Vz (ml) | Cl (ml/h) | AUC (h*ug/ml) |
|---|---|---|---|---|---|
|  | 1 | 48.48 | 0.036 | 0.00052 | 9015.21 |
|  | 2 | 51.32 | 0.032 | 0.00043 | 11191.67 |
|  | 3 | 67.61 | 0.037 | 0.00038 | 12088.07 |
|  | 4 | 45.28 | 0.055 | 0.00084 | 5844.74 |
| Average |  | 53.17 | 0.040 | 0.00054 | 9534.92 |
| STDEV |  | 9.93 | 0.010 | 0.00021 | 2777.94 |

Tables 26A-26B: Serum Concentrations and PK Parameters of COVA804 in Cynomolgus Monkeys.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 26A

COVA804 (IL-6R)

| Time (hr) | Monkey 1 | Monkey 2 | Monkey 3 | Monkey 4 | Average (ug/ml) | STDEV |
|---|---|---|---|---|---|---|
| 0.083 | 226.04 | 309.36 | 238.96 | 263.50 | 259.46 | 36.71 |
| 0.5 | 203.44 | 269.64 | 227.66 | 201.82 | 225.64 | 31.62 |
| 6 | 177.60 | 140.47 | 157.91 | 205.70 | 170.42 | 27.99 |
| 24 | 116.25 | 158.23 | 115.28 | 125.61 | 128.84 | 20.14 |
| 72 | 83.96 | 77.50 | 96.23 | 82.99 | 85.17 | 7.90 |
| 120 | 61.35 | 50.38 | 54.90 | 49.73 | 54.09 | 5.36 |
| 168 | 38.75 | 31.65 | 29.06 | 26.80 | 31.57 | 5.18 |
| 240 | 23.90 |  | 19.83 | 17.05 | 20.26 | 3.44 |
| 312 | 12.92 |  |  | 2.52 |  |  |
| 408 | 4.52 |  |  |  |  |  |
| 528 |  |  |  |  |  |  |

TABLE 26B

| COVA 804 (IL-6R) | Monkey ID | Pharmacokinetic Parameters Half Life (h) | Vz (ml) | Cl (ml/h) | AUC (h*ug/ml) |
|---|---|---|---|---|---|
|  | 1 | 69.55 | 0.026 | 0.00026 | 18904.03 |
|  | 2 | 74.29 | 0.030 | 0.00028 | 14644.67 |
|  | 3 | 76.60 | 0.030 | 0.00027 | 16104.51 |
|  | 4 | 54.49 | 0.024 | 0.00030 | 16522.15 |
| Average |  | 68.73 | 0.027 | 0.00028 | 16543.84 |
| STDEV |  | 9.94 | 0.003 | 0.00002 | 1767.38 |

Tables 27A-27B: Serum Concentrations and PK Parameters of COVA806 in Cynomolgus Monkeys.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 27A

COVA806 (IL-6R)

| | | Concentration (ug/ml) | | | | |
|---|---|---|---|---|---|---|
| Time (hr) | Monkey 1 | Monkey 2 | Monkey 3 | Monkey 4 | Average (ug/ml) | STDEV |
| 0.083 | 182.27 | 156.74 | 193.90 | 185.82 | 179.68 | 16.05 |
| 0.5 | 166.11 | 141.23 | 190.67 | 168.05 | 166.51 | 20.21 |
| 6 | 124.42 | 121.19 | 161.58 | 118.60 | 131.45 | 20.23 |
| 24 | 70.45 | 74.33 | 96.95 | 53.65 | 73.84 | 17.83 |
| 72 | 52.03 | 63.02 | 64.63 | 42.01 | 55.42 | 10.55 |
| 120 | 33.29 | 34.26 | 38.78 | 24.24 | 32.64 | 6.09 |
| 168 | 25.85 | 29.09 | 32.32 | 14.87 | 25.53 | 7.58 |
| 240 | 10.73 | 16.80 | 13.57 | | 13.70 | 3.04 |
| 312 | | 6.92 | | | | |
| 408 | | | | | | |
| 528 | | | | | | |

TABLE 27B

| | | Pharmacokinetic Parameters | | | |
|---|---|---|---|---|---|
| COVA 806 (IL-6R) | Monkey ID | Half Life (h) | Vz (ml) | Cl (ml/h) | AUC (h*ug/ml) |
| | 1 | 81.01 | 0.050 | 0.00043 | 10356.49 |
| | 2 | 81.60 | 0.045 | 0.00038 | 12207.01 |
| | 3 | 78.52 | 0.039 | 0.00034 | 13102.11 |
| | 4 | 64.05 | 0.054 | 0.00058 | 7244.31 |
| Average | | 76.29 | 0.047 | 0.00043 | 10727.48 |
| STDEV | | 8.27 | 0.007 | 0.00010 | 2588.31 |

Tables 28A-28B: Serum Concentrations and PK Parameters of COVA808 in Cynomolgus Monkeys.

A) Serum concentrations for each time point as determined by ELISA (IL-6R) are shown. The average values and standard deviation (STDEV) are also depicted. (B) Summary of important pharmacokinetic parameters such as half-life, volume of distribution (Vz), clearance (Cl) and area under the curve (AUC). The parameters were calculated using the serum concentrations presented in A. Similar serum concentrations and PK parameters were determined from IL-17A ELISA.

TABLE 28A

COVA808 (IL-6R)

| | | Concentration (ug/ml) | | | | |
|---|---|---|---|---|---|---|
| Time (hr) | Monkey 1 | Monkey 2 | Monkey 3 | Monkey 4 | Average (ug/ml) | STDEV |
| 0.083 | 200.18 | 175.96 | 129.15 | 163.05 | 167.08 | 29.61 |
| 0.5 | 217.61 | 172.41 | 109.77 | 164.02 | 165.95 | 44.23 |
| 6 | 151.75 | 109.77 | 96.86 | 106.55 | 116.23 | 24.30 |
| 24 | 79.10 | 80.39 | 61.34 | 71.03 | 72.97 | 8.79 |
| 72 | 77.49 | 65.54 | 45.20 | 54.56 | 60.70 | 13.94 |
| 120 | 36.16 | 37.13 | 32.29 | 31.32 | 34.22 | 2.85 |
| 168 | 22.02 | 36.81 | 32.29 | 17.37 | 27.12 | 8.97 |
| 240 | 14.53 | 20.34 | 12.91 | 5.29 | 13.27 | 6.20 |
| 312 | | | | | | |
| 408 | | | | | | |
| 528 | | | | | | |

TABLE 28B

| | | Pharmacokinetic Parameters | | | |
|---|---|---|---|---|---|
| COVA 808 (IL-6R) | Monkey ID | Half Life (h) | Vz (ml) | Cl (ml/h) | AUC (h*ug/ml) |
| | 1 | 92.98 | 0.047 | 0.00035 | 12386.59 |
| | 2 | 102.19 | 0.048 | 0.00033 | 12365.78 |
| | 3 | 87.98 | 0.056 | 0.00044 | 9641.05 |
| | 4 | 46.38 | 0.034 | 0.00051 | 9477.10 |
| Average | | 82.38 | 0.046 | 0.00041 | 10967.63 |
| STDEV | | 24.71 | 0.009 | 0.00008 | 1627.86 |

Figure 26:
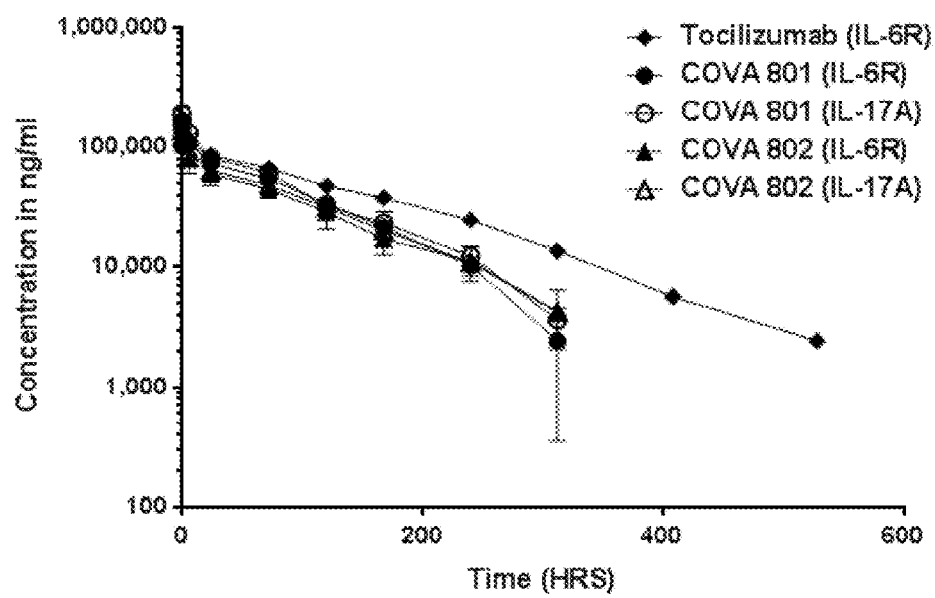
FIG. 26 shows mean serum concentrations plotted versus time for FynomAbs denoted COVA801 and COVA802 in cynomolgus monkeys.

FIG. 26 shows mean serum concentrations plotted versus time for COVA801 and COVA802 in cynomolgus monkeys. In FIG. 26, the mean serum concentrations+/− standard deviation (STDEV) as determined by either IL6R or IL-17A ELISAs are shown for COVA801 and COVA802 with tocilizumab (IL-6R ELISA) as a comparator.

Figure 27:
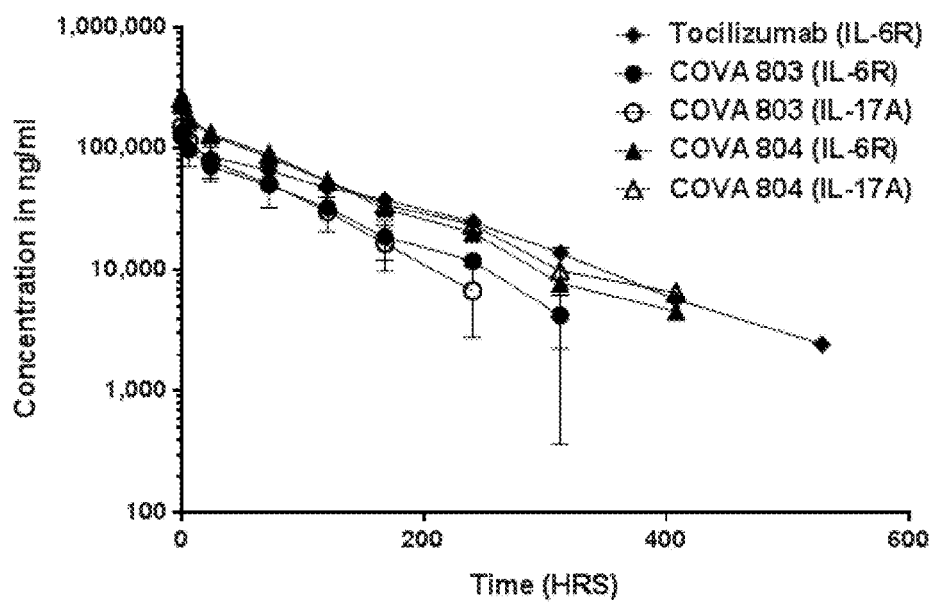
FIG. 27 shows mean serum concentrations plotted versus time for FynomAbs denoted COVA803 and COVA804 in cynomolgus monkeys.

FIG. 27 shows mean serum concentrations plotted versus time for COVA803 and COVA804 in cynomolgus monkeys. In FIG. 27, the mean serum concentrations+/− standard deviation (STDEV) as determined by either IL6R or IL-17A ELISAs are shown for COVA803 and COVA804 with tocilizumab (IL-6R ELISA) as a comparator.

Figure 28:
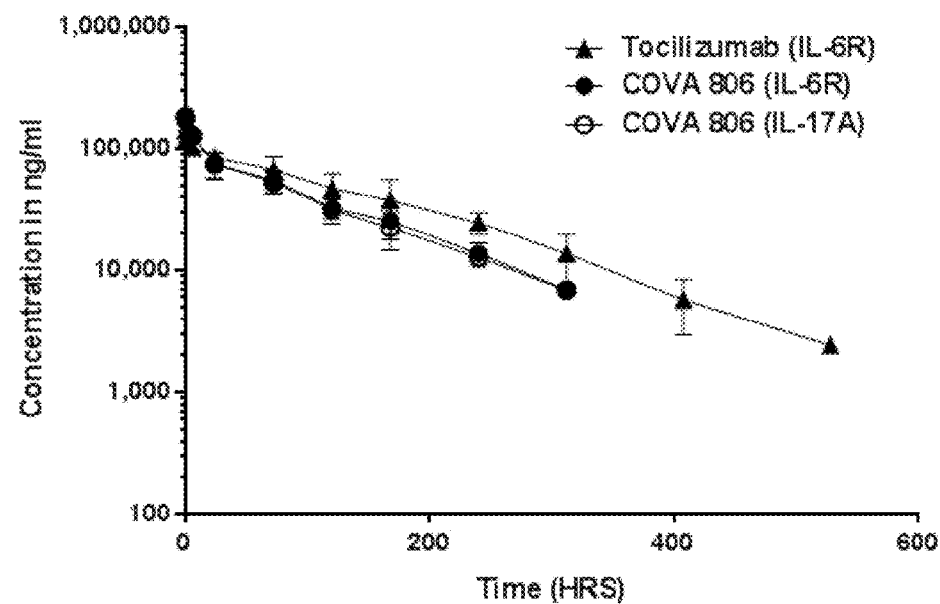
FIG. 28 shows mean serum concentrations plotted versus time for FynomAb denoted COVA806 in cynomolgus monkeys.

FIG. 28 shows mean serum concentrations plotted versus time for COVA806 in cynomolgus monkeys. In FIG. 28, the mean serum concentrations+/− standard deviation (STDEV) as determined by either IL6R or IL-17A ELISAs are shown for COVA806 with tocilizumab (IL-6R ELISA) as a comparator.

Figure 29:
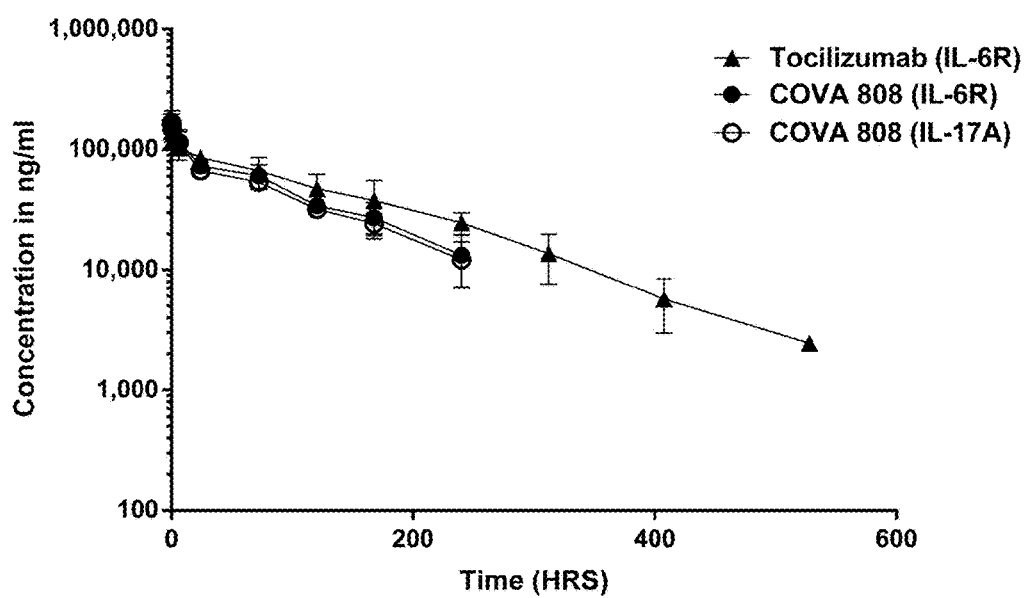
FIG. 29 shows mean serum concentrations plotted versus time for FynomAb denoted COVA808 in cynomolgus monkeys.

FIG. 29 shows mean serum concentrations plotted versus time for COVA808 in cynomolgus monkeys. In FIG. 29, the mean serum concentrations+/− standard deviation (STDEV) as determined by either IL6R or IL-17A ELISAs are shown for COVA808 with tocilizumab (IL-6R ELISA) as a comparator.

SUMMARY OF THE EXAMPLES

The data disclosed herein show that all 8 FynomAbs can bind and functionally block both IL-17A and IL-6R. All 8 constructs had very similar affinities for IL-17A and IL-6R and had similar functional activity in cell based assays, and the light chain fynomer fusions (FynomAbs denoted COVA802, COVA804, COVA806 and COVA808) had better SEC profiles and were less prone to aggregation.

The invention claimed is:

1. A bi-specific fusion polypeptide comprising:
   (a) a fynomer sequence comprising an amino acid sequence at least 90% identical to an amino acid sequence selected from: SEQ ID NO: 2, SEQ ID NO: 3, SEQ ID NO: 5, SEQ ID NO: 6, SEQ ID NO: 1, SEQ ID NO: 4 and SEQ ID NO: 7, wherein the amino acid sequences at positions 12-17 and 31-36 of the selected fynomer sequence is maintained and the fynomer sequence binds to interleukin-17a (IL-17a); and
   (b) an antibody or a subsequence thereof that binds to interleukin-6 receptor (IL-6R), wherein the fynomer sequence is conjugated to the antibody, or subsequence thereof, and the fusion polypeptide binds to both IL-17a and IL-6R and inhibits both IL-17a and IL-6R activities.

2. The fusion polypeptide of claim 1, wherein the fynomer sequence is conjugated to a heavy or light chain sequence of the antibody or subsequence thereof.

3. The fusion polypeptide of claim 1, wherein the fynomer sequence is conjugated to the amino terminus or the carboxyl terminus of a heavy chain sequence of the antibody or subsequence thereof.

4. The fusion polypeptide of claim 1, wherein the fynomer sequence is conjugated to an amino terminus or a carboxyl terminus of a light chain sequence of the antibody or subsequence thereof.

5. The fusion polypeptide of claim 1, wherein the fynomer sequence comprises an amino acid sequence at least 95% identical to an amino acid sequence selected from SEQ ID NO: 1, SEQ ID NO: 2, SEQ ID NO: 3, SEQ ID NO: 4, SEQ ID NO: 5, SEQ ID NO: 6 and SEQ ID NO: 7.

6. The fusion polypeptide of claim 1, wherein the fynomer sequence comprises an amino acid sequence selected from SEQ ID NO: 1, SEQ ID NO: 2, SEQ ID NO: 3, SEQ ID NO: 4, SEQ ID NO: 5, SEQ ID NO: 6 and SEQ ID NO: 7.

7. The fusion polypeptide of claim 1, wherein the fynomer sequence comprises the amino acid sequence of SEQ ID NO: 42.

8. The fusion polypeptide of claim 1, wherein the fynomer sequence binds to glycosylated IL-17a and thereby inhibits IL-17 receptor function or signaling.

9. The fusion polypeptide of claim 1, wherein the fynomer sequence has a binding affinity ($K_d$) for binding to glycosylated IL-17a of about 1 to about 200 nM.

10. The fusion polypeptide of claim 1, wherein the fynomer sequence has a greater binding affinity ($K_d$ or KD) for glycosylated IL-17a than the binding affinity of the fynomer sequence as set forth in SEQ ID NO:1 for glycosylated IL-17a.

11. The fusion polypeptide of claim 1, wherein the fusion polypeptide binds to IL-17a and binds to IL-6R simultaneously.

12. The fusion polypeptide of claim 1, wherein the fusion polypeptide binds to human IL-17a or IL-6R.

13. The fusion polypeptide of claim 1, wherein the fynomer sequence is conjugated to a heavy or light chain sequence of the antibody or subsequence thereof via a linker.

14. The fusion polypeptide of claim 1, wherein the fusion polypeptide is isolated or purified.

15. A pharmaceutical composition comprising the fusion polypeptide of claim 1.

16. The fusion polypeptide of claim 1, wherein the antibody or subsequence thereof comprises a heavy chain having the following CDR1-3: SEQ ID NO: 47, SEQ ID NO: 48, and SEQ ID NO: 49, and a light chain having the following CDR1-3: SEQ ID NO: 50, SEQ ID NO: 51, and SEQ ID NO: 52.

17. The fusion polypeptide of claim 16, wherein the antibody or subsequence thereof comprises a sequence at least 90% identical to the following heavy chain (HC) and light chain (LC) sequences: (HC) SEQ ID NO: 12 and (LC) SEQ ID NO: 13.

18. The fusion polypeptide of claim 17, wherein the antibody or subsequence thereof comprises the following heavy chain (HC) and light chain (LC) sequences:
(HC) SEQ ID NO: 12 and (LC) SEQ ID NO: 13.

19. The fusion polypeptide of claim 16, wherein the antibody or subsequence thereof comprises a pair of heavy chain (HC) and light chain (LC) sequences selected from the following:
   (HC) a heavy chain sequence at least 90% identical to SEQ ID NO: 14 and (LC) a light chain sequence at least 90% identical to SEQ ID NO: 15;
   (HC) a heavy chain sequence at least 90% identical to SEQ ID NO: 16 and (LC) a light chain sequence at least 90% identical to SEQ ID NO: 17;
   (HC) a heavy chain sequence at least 90% identical to SEQ ID NO: 18 and (LC) a light chain sequence at least 90% identical to SEQ ID NO: 19;
   (HC) a heavy chain sequence at least 90% identical to SEQ ID NO: 20 and (LC) a light chain sequence at least 90% identical to SEQ ID NO: 21;
   (HC) a heavy chain sequence at least 90% identical to SEQ ID NO: 22 and (LC) a light chain sequence at least 90% identical to SEQ ID NO: 23;
   (HC) a heavy chain sequence at least 90% identical to SEQ ID NO: 24 and (LC) a light chain sequence at least 90% identical to SEQ ID NO: 25;
   (HC) a heavy chain sequence at least 90% identical to SEQ ID NO: 26 and (LC) a light chain sequence at least 90% identical to SEQ ID NO: 27; and
   (HC) a heavy chain sequence at least 90% identical to SEQ ID NO: 28 and (LC) a light chain sequence at least 90% identical to SEQ ID NO: 29.

20. The fusion polypeptide of claim 19, wherein the antibody or subsequence thereof comprises a pair of heavy chain (HC) and light chain (LC) sequences selected from the following: SEQ ID NO: 14 and 15; SEQ ID NO: 16 and 17; SEQ ID NO: 18 and 19; SEQ ID NO: 20 and 21; SEQ ID NO: 22 and 23; SEQ ID NO: 24 and 25; SEQ ID NO: 26 and 27; and SEQ ID NO: 28 and 29.

* * * * *

SEQUENCE LISTING

<160> NUMBER OF SEQ ID NOS: 52

<210> SEQ ID NO 1
<211> LENGTH: 64
<212> TYPE: PRT
<213> ORGANISM: Artificial Sequence

```
<220> FEATURE:
<223> OTHER INFORMATION: Description of Artificial Sequence: IL-17a
      binding fynomer sequence

<400> SEQUENCE: 1

Gly Val Thr Leu Phe Val Ala Leu Tyr Asp Tyr Ala Asn His Gly Asn
1               5                   10                  15

Arg Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 2
<211> LENGTH: 64
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 2

Gly Val Thr Leu Phe Val Ala Leu Tyr Asp Tyr Lys Gln Lys Gly His
1               5                   10                  15

Leu Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 3
<211> LENGTH: 64
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 3

Gly Val Thr Leu Phe Val Ala Leu Tyr Asp Tyr Ser Ala Arg Gly Gln
1               5                   10                  15

Leu Asp Leu Ser Phe His Lys Gly Glu Lys Phe Gln Ile Leu Ser Thr
            20                  25                  30

His Glu Tyr Glu Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 4
<211> LENGTH: 64
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 4

Gly Val Thr Leu Phe Val Ala Leu Tyr Asp Tyr Asp Lys Leu Ser Ala
1               5                   10                  15

Leu Asp Leu Ser Phe His Lys Gly Glu Lys Phe Gln Ile Leu Ser Thr
```

```
                20                  25                  30

His Glu Tyr Glu Asp Trp Trp Glu Ala Arg Ser Leu Thr Thr Gly Glu
             35                  40                  45

Thr Gly Tyr Ile Pro Ser Asn Tyr Val Ala Pro Val Asp Ser Ile Gln
         50                  55                  60

<210> SEQ ID NO 5
<211> LENGTH: 64
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 5

Gly Val Thr Leu Phe Val Ala Leu Tyr Asp Tyr Glu Ser Val Ser Trp
1               5                   10                  15

Ser Asp Leu Ser Phe His Lys Gly Glu Lys Phe Gln Ile Leu Ser Thr
                20                  25                  30

His Glu Tyr Glu Asp Trp Trp Glu Ala Arg Ser Leu Thr Thr Gly Glu
             35                  40                  45

Thr Gly Tyr Ile Pro Ser Asn Tyr Val Ala Pro Val Asp Ser Ile Gln
         50                  55                  60

<210> SEQ ID NO 6
<211> LENGTH: 64
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 6

Gly Val Thr Leu Phe Val Ala Leu Tyr Asp Tyr Ser Ser Arg Gly Val
1               5                   10                  15

Leu Asp Leu Ser Phe His Lys Gly Glu Lys Phe Gln Ile Leu Ser Thr
                20                  25                  30

His Glu Tyr Glu Asp Trp Trp Glu Ala Arg Ser Leu Thr Thr Gly Glu
             35                  40                  45

Thr Gly Tyr Ile Pro Ser Asn Tyr Val Ala Pro Val Asp Ser Ile Gln
         50                  55                  60

<210> SEQ ID NO 7
<211> LENGTH: 64
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 7

Gly Val Thr Leu Phe Val Ala Leu Tyr Asp Tyr Ser Arg Lys Ser Asn
1               5                   10                  15

Leu Asp Leu Ser Phe His Lys Gly Glu Lys Phe Gln Ile Leu Ser Thr
                20                  25                  30

His Glu Tyr Glu Asp Trp Trp Glu Ala Arg Ser Leu Thr Thr Gly Glu
             35                  40                  45

Thr Gly Tyr Ile Pro Ser Asn Tyr Val Ala Pro Val Asp Ser Ile Gln
         50                  55                  60

<210> SEQ ID NO 8
```

```
<211> LENGTH: 448
<212> TYPE: PRT
<213> ORGANISM: Artificial Sequence
<220> FEATURE:
<223> OTHER INFORMATION: Description of Artificial Sequence: Tocilizumab
      heavy chain

<400> SEQUENCE: 8
```

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu

```
                    370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

<210> SEQ ID NO 9
<211> LENGTH: 214
<212> TYPE: PRT
<213> ORGANISM: Description of Artificial Sequence: Artificial Sequence
<220> FEATURE:
<223> OTHER INFORMATION: Tocilizumab light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 155
<212> TYPE: PRT
<213> ORGANISM: Homo sapiens

<400> SEQUENCE: 10

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30
```

Cys Pro Asn Ser Glu Asp Lys Asn Phe Pro Arg Thr Val Met Val Asn
                35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
                115                 120                 125

Cys Pro Asn Ser Phe Arg Leu Glu Lys Ile Leu Val Ser Val Gly Cys
                130                 135                 140

Thr Cys Val Thr Pro Ile Val His His Val Ala
145                 150                 155

<210> SEQ ID NO 11
<211> LENGTH: 467
<212> TYPE: PRT
<213> ORGANISM: Homo sapiens

<400> SEQUENCE: 11

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
                35                  40                  45

Gly Val Glu Pro Glu Asp Asn Ala Thr Val His Trp Val Leu Arg Lys
50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
                115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
                195                 200                 205

Gln Gly Cys Gly Ile Leu Gln Pro Asp Pro Ala Asn Ile Thr Val
                210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg

```
                    245                 250                 255
Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Leu Thr Thr Asn
                325                 330                 335

Lys Asp Asp Asn Ile Leu Phe Arg Asp Ser Ala Asn Ala Thr Ser
            340                 345                 350

Leu Pro Val Gln Asp Ser Ser Val Pro Leu Pro Thr Phe Leu Val
        355                 360                 365

Ala Gly Gly Ser Leu Ala Phe Gly Thr Leu Leu Cys Ile Ala Ile Val
    370                 375                 380

Leu Arg Phe Lys Lys Thr Trp Lys Leu Arg Ala Leu Lys Glu Gly Lys
385                 390                 395                 400

Thr Ser Met His Pro Pro Tyr Ser Leu Gly Gln Leu Val Pro Glu Arg
                405                 410                 415

Pro Arg Pro Thr Pro Val Leu Val Pro Leu Ile Ser Pro Pro Val Ser
            420                 425                 430

Pro Ser Ser Leu Gly Ser Asp Asn Thr Ser Ser His Asn Arg Pro Asp
        435                 440                 445

Ala Arg Asp Pro Arg Ser Pro Tyr Asp Ile Ser Asn Thr Asp Tyr Phe
    450                 455                 460

Phe Pro Arg
465

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: IL-6R
      binding antibody heavy chain

<400> SEQUENCE: 12

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: IL-6R
      binding antibody light chain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45
```

-continued

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 527
<212> TYPE: PRT
<213> ORGANISM: Artificial Sequence
<220> FEATURE:
<223> OTHER INFORMATION: Description of Artificial Sequence: aka COVA
      801 heavy chain

<400> SEQUENCE: 14

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser 180                 185                 190
Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Gly Ser Gly Gly Gly Gly Ser Gly
    450                 455                 460

Val Thr Leu Phe Val Ala Leu Tyr Asp Tyr Lys Gln Lys Gly His Leu
465                 470                 475                 480

Asp Leu Ser Phe His Lys Gly Glu Lys Phe Gln Ile Leu Ser Thr His
                485                 490                 495

Glu Tyr Glu Asp Trp Trp Glu Ala Arg Ser Leu Thr Thr Gly Glu Thr
            500                 505                 510

Gly Tyr Ile Pro Ser Asn Tyr Val Ala Pro Val Asp Ser Ile Gln
        515                 520                 525

<210> SEQ ID NO 15
<211> LENGTH: 214
<212> TYPE: PRT
<213> ORGANISM: Artificial Sequence
<220> FEATURE:
<223> OTHER INFORMATION: Description of Artificial Sequence: aka COVA
      801 light chain

<400> SEQUENCE: 15

Asp Ile Gln Met Thr Gln Ser Pro Ser Ser Leu Ser Ala Ser Val Gly
1               5                   10                  15

-continued

```
Asp Arg Val Thr Ile Thr Cys Arg Ala Ser Gln Asp Ile Ser Ser Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
             85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 16
<211> LENGTH: 448
<212> TYPE: PRT
<213> ORGANISM: Artificial Sequence
<220> FEATURE:
<223> OTHER INFORMATION: Description of Artificial Sequence: aka COVA
      802 heavy chain

<400> SEQUENCE: 16

```
Gln Val Gln Leu Gln Glu Ser Gly Pro Gly Leu Val Arg Pro Ser Gln
1               5                  10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
             85                  90                  95

Ala Arg Ser Leu Ala Arg Thr Thr Ala Met Asp Tyr Trp Gly Gln Gly
        100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 17
<211> LENGTH: 293
<212> TYPE: PRT
<213> ORGANISM: Artificial Sequence
<220> FEATURE:
<223> OTHER INFORMATION: Description of Artificial Sequence: aka COVA
      802 light chain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
```

```
                65                  70                  75                  80
Glu Asp Ile Ala Thr Tyr Tyr Cys Gln Gln Gly Asn Thr Leu Pro Tyr
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Gly Ser Gly Gly Gly Gly Ser
        210                 215                 220

Gly Gly Gly Gly Ser Gly Val Thr Leu Phe Val Ala Leu Tyr Asp Tyr
225                 230                 235                 240

Lys Gln Lys Gly His Leu Asp Leu Ser Phe His Lys Gly Glu Lys Phe
                245                 250                 255

Gln Ile Leu Ser Thr His Glu Tyr Glu Asp Trp Trp Glu Ala Arg Ser
                260                 265                 270

Leu Thr Thr Gly Glu Thr Gly Tyr Ile Pro Ser Asn Tyr Val Ala Pro
            275                 280                 285

Val Asp Ser Ile Gln
        290

<210> SEQ ID NO 18
<211> LENGTH: 527
<212> TYPE: PRT
<213> ORGANISM: Artificial Sequence
<220> FEATURE:
<223> OTHER INFORMATION: Description of Artificial Sequence: aka COVA
      803 heavy chain

<400> SEQUENCE: 18

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125
```

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Gly Ser Gly Gly Gly Gly Ser Gly
    450                 455                 460

Val Thr Leu Phe Val Ala Leu Tyr Asp Tyr Ser Ala Arg Gly Gln Leu
465                 470                 475                 480

Asp Leu Ser Phe His Lys Gly Glu Lys Phe Gln Ile Leu Ser Thr His
                485                 490                 495

Glu Tyr Glu Asp Trp Trp Glu Ala Arg Ser Leu Thr Thr Gly Glu Thr
            500                 505                 510

Gly Tyr Ile Pro Ser Asn Tyr Val Ala Pro Val Asp Ser Ile Gln
        515                 520                 525

<210> SEQ ID NO 19
<211> LENGTH: 214
<212> TYPE: PRT

```
<213> ORGANISM: Artificial Sequence
<220> FEATURE:
<223> OTHER INFORMATION: Description of Artificial Sequence: aka COVA
      803 light chain

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 448
<212> TYPE: PRT
<213> ORGANISM: Artificial Sequence
<220> FEATURE:
<223> OTHER INFORMATION: Description of Artificial Sequence: aka COVA
      804 heavy chain

<400> SEQUENCE: 20

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
```

```
                100             105                  110
    Ser Leu Val Thr Val Ser Ser Ala Ser Thr Lys Gly Pro Ser Val Phe
                    115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
    145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                    195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
    225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
    305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
    385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                    435                 440                 445

<210> SEQ ID NO 21
<211> LENGTH: 293
<212> TYPE: PRT
<213> ORGANISM: Artificial Sequence
<220> FEATURE:
<223> OTHER INFORMATION: Description of Artificial Sequence: aka COVA
      804 light chain

<400> SEQUENCE: 21

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                      55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Gly Val Thr Leu Phe Val Ala Leu Tyr Asp Tyr
225                 230                 235                 240

Ser Ala Arg Gly Gln Leu Asp Leu Ser Phe His Lys Gly Glu Lys Phe
                245                 250                 255

Gln Ile Leu Ser Thr His Glu Tyr Glu Asp Trp Trp Glu Ala Arg Ser
            260                 265                 270

Leu Thr Thr Gly Glu Thr Gly Tyr Ile Pro Ser Asn Tyr Val Ala Pro
        275                 280                 285

Val Asp Ser Ile Gln
    290

<210> SEQ ID NO 22
<211> LENGTH: 527
<212> TYPE: PRT
<213> ORGANISM: Artificial Sequence
<220> FEATURE:
<223> OTHER INFORMATION: Description of Artificial Sequence: aka COVA
      805 heavy chain

<400> SEQUENCE: 22

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80
```

```
Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Gly Gly Gly Gly Ser Gly Gly Gly Ser Gly Gly Gly Gly Ser Gly
450                 455                 460

Val Thr Leu Phe Val Ala Leu Tyr Asp Tyr Glu Ser Val Ser Trp Ser
465                 470                 475                 480

Asp Leu Ser Phe His Lys Gly Glu Lys Phe Gln Ile Leu Ser Thr His
                485                 490                 495
```

```
Glu Tyr Glu Asp Trp Trp Glu Ala Arg Ser Leu Thr Thr Gly Glu Thr
                500                 505                 510

Gly Tyr Ile Pro Ser Asn Tyr Val Ala Pro Val Asp Ser Ile Gln
        515                 520                 525

<210> SEQ ID NO 23
<211> LENGTH: 214
<212> TYPE: PRT
<213> ORGANISM: Artificial Sequence
<220> FEATURE:
<223> OTHER INFORMATION: Description of Artificial Sequence: aka COVA
      805 light chain

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 448
<212> TYPE: PRT
<213> ORGANISM: Artificial Sequence
<220> FEATURE:
<223> OTHER INFORMATION: Description of Artificial Sequence: aka COVA
      806 heavy chain

<400> SEQUENCE: 24

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45
```

```
Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 25
<211> LENGTH: 293
<212> TYPE: PRT
```

<213> ORGANISM: Artificial Sequence
<220> FEATURE:
<223> OTHER INFORMATION: Description of Artificial Sequence: aka COVA 806 light chain

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Gly Gly Gly Gly Ser Gly Val Thr Leu Phe Val Ala Leu Tyr Asp Tyr
225                 230                 235                 240

Glu Ser Val Ser Trp Ser Asp Leu Ser Phe His Lys Gly Glu Lys Phe
                245                 250                 255

Gln Ile Leu Ser Thr His Glu Tyr Glu Asp Trp Trp Glu Ala Arg Ser
            260                 265                 270

Leu Thr Thr Gly Glu Thr Gly Tyr Ile Pro Ser Asn Tyr Val Ala Pro
        275                 280                 285

Val Asp Ser Ile Gln
    290

<210> SEQ ID NO 26
<211> LENGTH: 527
<212> TYPE: PRT
<213> ORGANISM: Artificial Sequence
<220> FEATURE:
<223> OTHER INFORMATION: Description of Artificial Sequence: aka COVA 807 heavy chain

<400> SEQUENCE: 26

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp

```
                20                  25                  30
His Ala Trp Ser Trp Val Arg Gln Pro Gly Arg Gly Leu Glu Trp
            35                  40                  45
Ile Gly Tyr Ile Ser Tyr Ser Gly Ile Thr Thr Tyr Asn Pro Ser Leu
50                  55                  60
Lys Ser Arg Val Thr Met Leu Arg Asp Thr Ser Lys Asn Gln Phe Ser
65                  70                  75                  80
Leu Arg Leu Ser Ser Val Thr Ala Ala Asp Thr Ala Val Tyr Tyr Cys
            85                  90                  95
Ala Arg Ser Leu Ala Arg Thr Thr Ala Met Asp Tyr Trp Gly Gln Gly
            100                 105                 110
Ser Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

Gly Gly Gly Gly Ser Gly Gly Gly Ser Gly Gly Gly Ser Gly
        450                 455                 460

Val Thr Leu Phe Val Ala Leu Tyr Asp Tyr Ser Arg Gly Val Leu
465                 470                 475                 480

Asp Leu Ser Phe His Lys Gly Glu Lys Phe Gln Ile Leu Ser Thr His
                485                 490                 495

Glu Tyr Glu Asp Trp Trp Glu Ala Arg Ser Leu Thr Thr Gly Glu Thr
                500                 505                 510

Gly Tyr Ile Pro Ser Asn Tyr Val Ala Pro Val Asp Ser Ile Gln
                515                 520                 525

<210> SEQ ID NO 27
<211> LENGTH: 214
<212> TYPE: PRT
<213> ORGANISM: Artificial Sequence
<220> FEATURE:
<223> OTHER INFORMATION: Description of Artificial Sequence: aka COVA
      807 light chain

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 448
<212> TYPE: PRT
<213> ORGANISM: Artificial Sequence
<220> FEATURE:
<223> OTHER INFORMATION: Description of Artificial Sequence: aka COVA
      808 heavy chain

<400> SEQUENCE: 28

-continued

```
Gln Val Gln Leu Gln Glu Ser Gly Pro Gly Leu Val Arg Pro Ser Gln
 1               5                  10                  15

Thr Leu Ser Leu Thr Cys Thr Val Ser Gly Tyr Ser Ile Thr Ser Asp
             20                  25                  30

His Ala Trp Ser Trp Val Arg Gln Pro Pro Gly Arg Gly Leu Glu Trp
             35                  40                  45

Ile Gly Tyr Ile Ser Tyr Ser Gly Ile Thr Thr Tyr Asn Pro Ser Leu
         50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

-continued

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 29
<211> LENGTH: 293
<212> TYPE: PRT
<213> ORGANISM: Artificial Sequence
<220> FEATURE:
<223> OTHER INFORMATION: Description of Artificial Sequence: aka COVA
      808 light chain

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
            210                 215                 220

Gly Gly Gly Gly Ser Gly Val Thr Leu Phe Val Ala Leu Tyr Asp Tyr
225                 230                 235                 240

Ser Ser Arg Gly Val Leu Asp Leu Ser Phe His Lys Gly Glu Lys Phe
                245                 250                 255

Gln Ile Leu Ser Thr His Glu Tyr Glu Asp Trp Trp Glu Ala Arg Ser
            260                 265                 270

Leu Thr Thr Gly Glu Thr Gly Tyr Ile Pro Ser Asn Tyr Val Ala Pro
        275                 280                 285

Val Asp Ser Ile Gln
        290

<210> SEQ ID NO 30
<211> LENGTH: 63
<212> TYPE: PRT
<213> ORGANISM: Artificial Sequence

```
<220> FEATURE:
<223> OTHER INFORMATION: Description of Artificial Sequence: IL-17A
      binder 2C1

<400> SEQUENCE: 30

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 31
<211> LENGTH: 63
<212> TYPE: PRT
<213> ORGANISM: Artificial Sequence
<220> FEATURE:
<223> OTHER INFORMATION: Description of Artificial Sequence: IL-17A
      binder A1_2

<400> SEQUENCE: 31

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Ser
        35                  40                  45

Gly Tyr Ile Pro Ser Asn Tyr Val Ala Pro Val Asp Ser Ile Gln
    50                  55                  60

<210> SEQ ID NO 32
<211> LENGTH: 63
<212> TYPE: PRT
<213> ORGANISM: Artificial Sequence
<220> FEATURE:
<223> OTHER INFORMATION: Description of Artificial Sequence: IL-17A
      binder B1_2

<400> SEQUENCE: 32

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 33
<211> LENGTH: 235
<212> TYPE: PRT
<213> ORGANISM: Artificial Sequence
<220> FEATURE:
<223> OTHER INFORMATION: Description of Artificial Sequence: Secukinumab
      variable light chain

<400> SEQUENCE: 33

Met Ser Val Pro Thr Gln Val Leu Gly Leu Leu Leu Leu Trp Leu Thr
1               5                   10                  15

Asp Ala Arg Cys Glu Ile Val Leu Thr Gln Ser Pro Gly Thr Leu Ser
```

```
              20                  25                  30
Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Cys Thr Phe Gly Gln Gly Thr Arg Leu Glu Ile Lys
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 34
<211> LENGTH: 475
<212> TYPE: PRT
<213> ORGANISM: Artificial Sequence
<220> FEATURE:
<223> OTHER INFORMATION: Description of Artificial Sequence: Seckinumab
      variable heavy chain

<400> SEQUENCE: 34

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Asn Tyr Trp Met Asn Trp Val Arg Gln Ala Pro Gly Lys Gly Leu
    50                  55                  60

Glu Trp Val Ala Ala Ile Asn Gln Asp Gly Ser Glu Lys Tyr Tyr Val
65                  70                  75                  80

Gly Ser Val Lys Gly Arg Phe Thr Ile Ser Arg Asp Asn Ala Lys Asn
                85                  90                  95

Ser Leu Tyr Leu Gln Met Asn Ser Leu Arg Val Glu Asp Thr Ala Val
            100                 105                 110

Tyr Tyr Cys Val Arg Asp Tyr Tyr Asp Ile Leu Thr Asp Tyr Tyr Ile
            115                 120                 125

His Tyr Trp Tyr Phe Asp Leu Trp Gly Arg Gly Thr Leu Val Thr Val
            130                 135                 140
```

-continued

```
Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
            165                 170                 175

Asp Tyr Phe Pro Glu Pro Val Thr Val Ser Trp Asn Ser Gly Ala Leu
        180                 185                 190

Thr Ser Gly Val His Thr Phe Pro Ala Val Leu Gln Ser Ser Gly Leu
    195                 200                 205

Tyr Ser Leu Ser Ser Val Val Thr Val Pro Ser Ser Ser Leu Gly Thr
210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly
465                 470                 475
```

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 35

```
Gly Val Thr Leu Phe Val Ala Leu Tyr Asp Tyr
1               5                   10
```

<210> SEQ ID NO 36

```
<211> LENGTH: 13
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 36

Asp Leu Ser Phe His Lys Gly Glu Lys Phe Gln Ile Leu
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 37

Ser Thr His Glu Tyr Glu
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 38

Ser Thr His Glu Tyr Glu Asp
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 39

Trp Trp Glu Ala Arg
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 40

Asp Trp Trp Glu Ala Arg
1               5

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 41
```

Ser Leu Thr Thr Gly Glu Thr Gly Tyr Ile Pro Ser Asn Tyr Val Ala
1               5                   10                  15

Pro Val Asp Ser Ile Gln
            20

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 42

Gln Ile Leu Ser Thr His Glu Tyr Glu Asp Trp Trp Glu Ala Arg
1               5                   10                  15

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:  Linker
      peptide

<400> SEQUENCE: 43

Gly Gly Gly Gly Ser
1               5

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence:  Linker
      peptide

<400> SEQUENCE: 44

Gly Gly Gly Gly Ser Gly Gly Gly Gly Ser Gly Gly Gly Gly Ser
1               5                   10                  15

<210> SEQ ID NO 45
<211> LENGTH: 63
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 45

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: IL-17a
      binding fynomer sequence

<400> SEQUENCE: 46

Ser Thr His Glu Tyr
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Heavy chain
      variable region CDRs1-3

<400> SEQUENCE: 47

Ser Asp His Ala Trp Ser
1               5

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Heavy chain
      variable region CDRs1-3

<400> SEQUENCE: 48

Tyr Ile Ser Tyr Ser Gly Ile Thr Thr Tyr Asn Pro Ser Leu Lys Ser
1               5                   10                  15

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Heavy chain
      variable region CDRs1-3

<400> SEQUENCE: 49

Ser Leu Ala Arg Thr Thr Ala Met Asp Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Light chain
      variable region CDRs1-3

<400> SEQUENCE: 50

Arg Ala Ser Gln Asp Ile Ser Ser Tyr Leu Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Light chain
      variable region CDRs1-3

<400> SEQUENCE: 51

Tyr Thr Ser Arg Leu His Ser
1               5

<210> SEQ ID NO 52
<211> LENGTH: 9

```
<212> TYPE: PRT
<213> ORGANISM: Artificial Sequence
<220> FEATURE:
<223> OTHER INFORMATION: Description of Artificial Sequence: Light chain
      variable region CDRs1-3

<400> SEQUENCE: 52

Gln Gln Gly Asn Thr Leu Pro Tyr Thr
1               5
```